US008709798B2

(12) United States Patent
Berger

(10) Patent No.: US 8,709,798 B2
(45) Date of Patent: Apr. 29, 2014

(54) NUCLEIC ACIDS FOR CLONING AND EXPRESSING MULTIPROTEIN COMPLEXES

(75) Inventor: Imre Berger, St. Egreve (FR)

(73) Assignee: Europaisches Laboratorium fur Molekularbiologie, Heidelberg (DE)

( * ) Notice: Subject to any disclaimer, the term of this patent is extended or adjusted under 35 U.S.C. 154(b) by 0 days.

(21) Appl. No.: 13/254,831

(22) PCT Filed: Mar. 8, 2010

(86) PCT No.: PCT/EP2010/052892
§ 371 (c)(1),
(2), (4) Date: Sep. 2, 2011

(87) PCT Pub. No.: WO2010/100278
PCT Pub. Date: Sep. 10, 2010

(65) Prior Publication Data
US 2012/0149060 A1    Jun. 14, 2012

(30) Foreign Application Priority Data
Mar. 6, 2009    (EP) .................................... 09154567

(51) Int. Cl.
*C12N 15/00* (2006.01)
*C12N 15/64* (2006.01)
*C12N 5/00* (2006.01)
*C12N 1/20* (2006.01)

(52) U.S. Cl.
USPC ..... 435/320.1; 435/91.4; 435/325; 435/252.3

(58) Field of Classification Search
None
See application file for complete search history.

(56) References Cited

FOREIGN PATENT DOCUMENTS

WO    WO 2005/040336 A2    5/2005
WO    WO 2005/085456 A1    9/2005

OTHER PUBLICATIONS

Chevalier et al. Homing endonucleases: structural and functional insight into the catalysts of intron/intein mobility. 2001. Nucleic Acids Research. vol. 29, No. 18, pp. 3757-3774.*
Asselbergs, F.A.M., "Creation of a Novel, Versatile Multiple Cloning Site Cut by Four Rare-Cutting Homing Endonucleases", BioTechniques, Apr. 1996, pp. 558-562, vol. 20.
Tan, S. et al. "The pST44 polycistronic expression system for producing protein complexes in *Escherichia coli*," Protein Expression & Purification, 2005, pp. 385-395, vol. 40, Elsevier Inc.
Thomson, J. Michael et al., "Artificial gene-clusters engineered into plants using a vector system based on intron- and intein-encoded endonucleases," In Vitro Cell Dev. Biol.-Plant, Nov.-Dec. 2002, pp. 537-542.
Stoddard, B.L., "Homing endonuclease structure and function," Quarterly Reviews of Biophysics, 2006, pp. 49-95, vol. 38, No. 1, Cambridge University Press, United Kingdom.
Bienossek, Christoph, et al., "Automated unrestricted multigene recombineering for multiprotein complex production", Nature Methods, Jun. 2009, pp. 447-450, vol. 6, No. 6, Nature America, Inc.
Rual, J.F. et al., "Towards a proteome-scale map of the human protein-protein interaction network," Nature, Oct. 2005, pp. 1173-1178, vol. 437, No. 20, Nature Publishing Group.
Charbonnier, S. et al. "The social network of a cell: Recent advances in interactome mapping," Biotechnology Annual Review, 2008, pp. 1-28, vol. 14, Elsevier B.V.
Fitzgerald D.J. et al. "Protein complex expression by using multigene baculoviral vectors," Nature Methods, Dec. 2006, pp. 1021-1032, vol. 3, No. 12, Nature Publishing Group.
Tolia, N.H. et al. "Strategies for protein coexpression in *Escherichia coli*," Nature Methods, Jan. 2006, pp. 55-64, vol. 3, No. 1, Cold Spring Harbor Laboratory Press, Cold Spring Harbor, New York.
Chanda P.K. et al. "A set of ligation-independent expression vectors for co-expression of proteins in *Escherichia coli*," Protein Expression & Purification, 2006, pp. 217-224, vol. 47.
Scheich, C. et al. "Vectors for co-expression of an unrestricted number of proteins," Nucleic Acids Research, 2007, pp. 1-7, vol. 35, No. 6.
Bieniossek, C. et al. "The molecular architecture of the metalloprotease FtsH," PNAS, 2006, pp. 3066-3071, vol. 103, No. 9, The National Academy of Sciences of the USA.
Berger, P. et al. "Membrane association of myotubularin-related protein 2 is mediated by a pleckstrin homology-GRAM domain and a coiled-oil dimerization module," PNAS, 2003, pp. 12177-12182, vol. 100, No. 2, National Academy of Sciences of USA.
Li, M. Z. & Elledge, S.J. "Harnessing homologous recombination in vitro to generate recombinant DNA via SLIC," Nature Methods, Mar. 2007, pp. 251-256, vol. 4, No. 3, Nature Publishing Group.

(Continued)

*Primary Examiner* — Anne Gussow
*Assistant Examiner* — Channing S Mahatan
(74) *Attorney, Agent, or Firm* — Cislo & Thomas, LLP

(57) ABSTRACT

The present invention relates to a nucleic acid containing at least one homing endonuclease site (HE) and at least one restriction enzyme site (X) wherein the HE and X sites are selected such that HE and X result in compatible cohesive ends when cut by the homing endonuclease and restriction enzyme, respectively, and the ligation product of HE and X cohesive ends can neither be cleaved by the homing endonuclease nor by the restriction enzyme. Further subject-matter of the present invention relates to a vector comprising the nucleic acid of the present invention, host cells containing the nucleic acid and/or the vector, a kit for cloning and/or expression of multiprotein complexes making use of the vector and the host cells, a method for producing a vector containing multiple expression cassettes, and a method for producing multiprotein complexes. The invention also relates to a methods of assembling multiple single vectors ("vector entities") into fusion vectors and to method of disassembling a fusion vector containing multiple of such vector entities into single vectors. The invention is also directed to fusion vectors containing multiple vector entities.

20 Claims, 45 Drawing Sheets

(56) References Cited

OTHER PUBLICATIONS

Gaiser, F. et al. "Novel Dimerization Fold of RAP30/RAP74 in Human TFIIF at 1.7 A Resolution," J. Mol. Biol. 2000, pp. 1119-1127, vol. 302, Academic Press.

Romier, C. et al. "The NF-YB/NF-YC Structure Gives Insight into DNA Binding and Transcription Regulation by CCAAT Factor NF-Y," The Journal of Biological Chemistry, 2003, pp. 1336-1345, vol. 278, No. 2, The American Society of Biochemistry and Molecular Biology, Inc.

Stebbins, C. E. et al. "Structure of the VHL-ElonginC-ElonginB Complex: Implications for VHL Tumor Suppressor Function," Science, Apr. 16, 1999, pp. 455-461, vol. 284.

Studier, F. W. "Protein production by auto-induction in high density shaking cultures," Protein Expression and Purification, 2005, pp. 207-234, vol. 41, Elsevier, Inc.

Duong, F. & Wickner, W. "The SecDFyajC domain of preprotein translocase controls preprotein movement by regulating SecA membrane cycling," The EMBO Journal, 1997, pp. 4871-4879, vol. 16, No. 16, Oxford University Press.

* cited by examiner

Acceptor

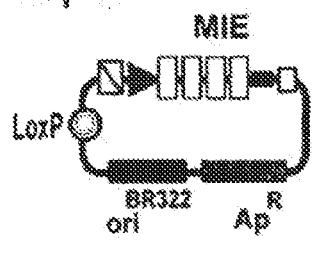
pACE

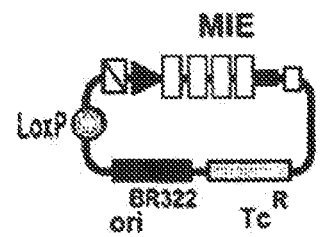
pACE2

Donor

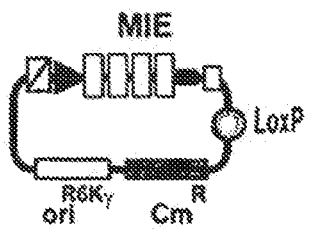
pDC

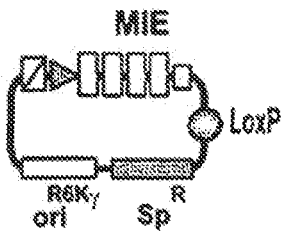
pDS

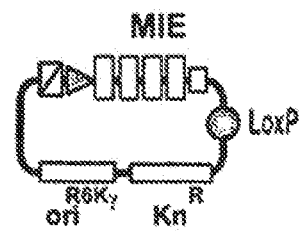
pDK

▶ Promoter 1 (T7)  ◨ Homing endonuclease site 1 (I-Ceul)
▷ Promoter 2 (Lac)  ◩ Homing endonuclease site 2 (PI-SceI)
■ Terminator (T7)   □ BstXI site MIE    Multiple Integration Element
LoxP   31bp imperfect inverted repeat for Cre mediated fusion
ori$^{R6K\gamma}$  conditional origin of replication from phage R6Kγ
ori$^{BR322}$  regular origin of replication

*Resistance markers Ampicillin (Ap), Tetracyclin (Tc), Chloramphenicol (Cm), Spectinomycin (Sp), Kanamycin (Kn)*

Fig. 1

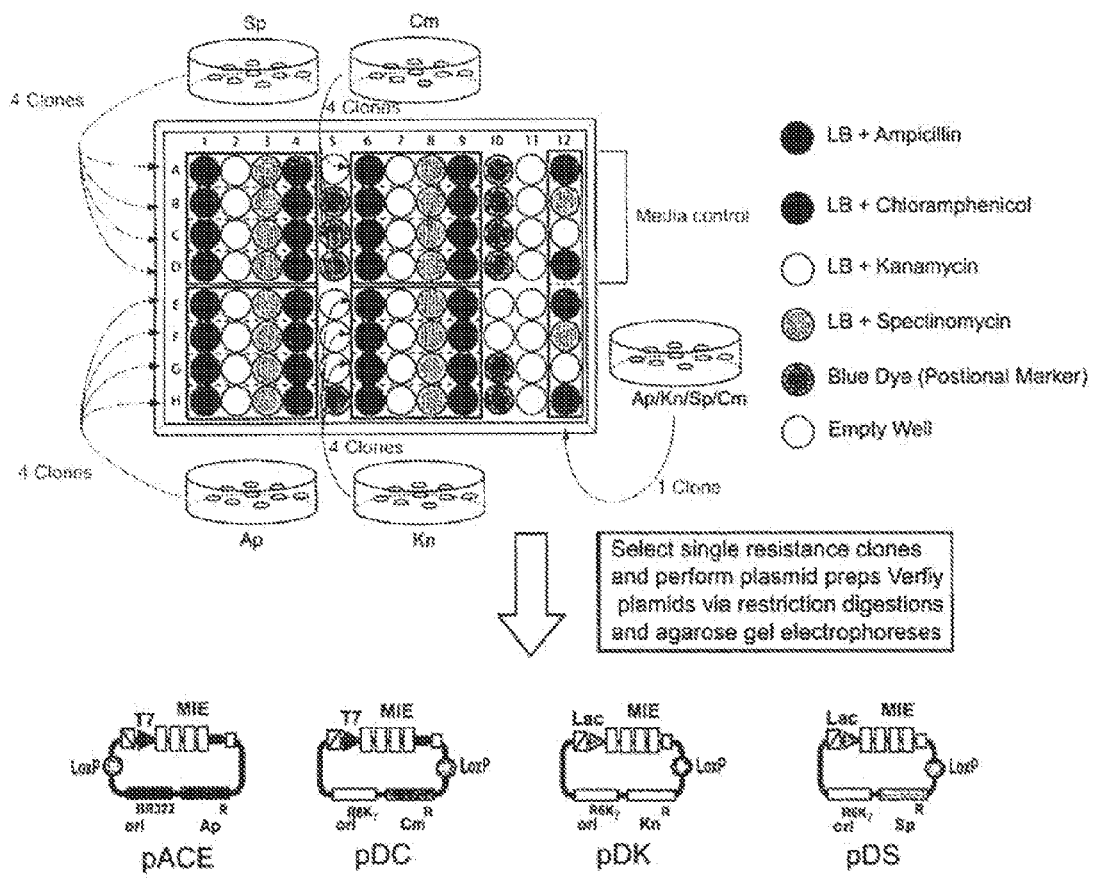
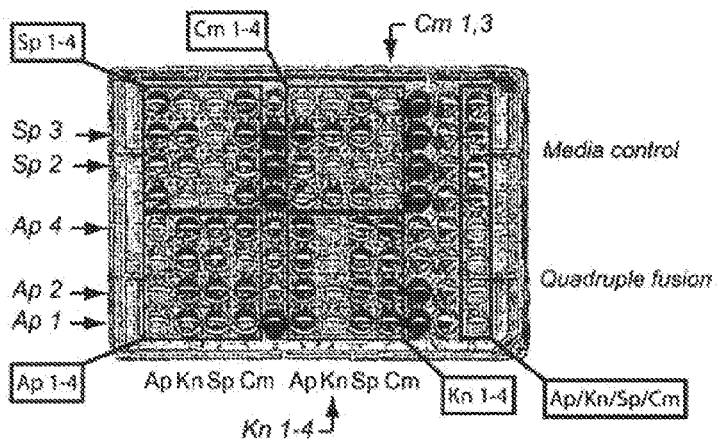
Fig. 12 p10 EC structure as in pIDK

NUCLEIC ACIDS FOR CLONING AND EXPRESSING MULTIPROTEIN COMPLEXES

The present invention relates to a nucleic acid containing at least one homing endonuclease site (HE) and at least one restriction enzyme site (X) wherein the HE and X sites are selected such that HE and X result in compatible cohesive ends when cut by the homing endonuclease and restriction enzyme, respectively, and the ligation product of HE and X cohesive ends can neither be cleaved by the homing endonuclease nor by the restriction enzyme. Further subject-matter of the present invention relates to a vector comprising the nucleic acid of the present invention, host cells containing the nucleic acid and/or the vector, a kit for cloning and/or expression of multiprotein complexes making use of the vector and the host cells, a method for producing a vector containing multiple expression cassettes, and a method for producing multiprotein complexes. The invention also relates to a method for assembling multiple single vectors ("vector entities") into fusion vectors and to a method for disassembling a fusion vector containing multiple of such vector entities into lower order fusion vectors and/or into single vectors. The invention is also directed to fusion vectors containing multiple vector entities.

Many vital processes in cells are controlled by proteins associating into interlocking molecular machines, in higher eukaryotes often containing 10 and more subunits (Rual, J. F. et al. Nature 437, 1173-1178 (2005); Charbonnier, S., Gallego, O. and Gavin, A. C. Biotechnol. Annu. Rev. 14, 1-28 (2008)). This has profound consequences for functional and structural studies that now aim to decipher physiologically relevant molecular mechanisms. Consequently, work on complexes is increasingly becoming imperative in contemporary biology. The low abundance and frequently heterogeneous nature of many multisubunit complexes, however, often preclude extraction from source.

Recombinant production methods certainly have had a decisive impact on life science research. In particular E. coli, as an expression host, is commonplace. Successful functional analysis of proteins and elucidation of their molecular architecture often crucially depends on introducing alterations, such as truncations, mutations and extension with purification tags, or with particular promoter/terminator elements. The ensuing requirements in terms of experimental throughput are already considerable for diversifying single open reading frames (ORFs). In particular structural genomics consortia demand the standardization of subcloning routines and implementation of automation for this. The exponential increase in workload when many ORFs have to be rapidly diversified and assembled in the context of a multisubunit complex is daunting, and an unresolved challenge to date.

A number of systems have been introduced in recent years for expression of several genes in eukaryotic and prokaryotic hosts; see, e.g. Fitzgerald et al. (2006) Nat. Methods 3, 1021-1032; Tan et al. (2005) Protein Expr. Purif. 40, 385-395 (2005); Tolia, N. H. and Joshua-Tor (2006). Nat. Methods 3, 55-64; Chanda et al. (2006) Protein Expr. Purif. 47, 217-224; Scheich et al. (2007). Nucleic Acids Res. 35, e43 (2007). In spite of considerable improvements of eukaryotic expression systems, in particular the baculovirus/insect cell expression (Fitzgerald et al. (2006), supra), E. coli still remains to date the dominant work-horse in most laboratories, for many good reasons such as low-cost and availability of a multitude of specialized expression strains. The current co-expression systems for E. coli rely essentially on serial, mostly conventional (i.e. restriction/ligation) subcloning of encoding genes either as single expression cassettes (Tolia et al. (2006), supra; Chanda et al. (2006), supra) or as polycistrons constituting several genes under the control of the same promoter (Tan et al. (2005), supra). This considerably limits the applicability of these co-expression techniques for production of protein complexes with many subunits, in particular at the throughput typically required for structural molecular biology.

A major impediment of such largely serial (one gene at a time) constructions stems from the inherent inflexibility with regards to rapidly revising an expression experiment once the multiprotein complex has been produced, purified and characterized. However, such revisions, including variations of the protein subunits, are a sine qua non in contemporary functional and structural research.

Fitzgerald et al. (2006), supra, and WO-A-2005/085456 describe polynucleotides having a so-called multiplication module wherein two expression cassettes in head-to-head, head-to-tail or tail-to-tail orientation are flanked by specifically designed pairs of restriction enzyme sites allowing iterative cloning of multiple genes into the expression cassettes.

In view of the draw backs of prior art constructs it is therefore the technical problem underlying the present invention to provide versatile systems for cloning and expression of multiprotein complexes.

The solution to the above technical problem is achieved by the provision of the embodiments of the present invention as defined in the claims.

In particular, the present invention relates to a nucleic acid (or polynucleotide) containing at least one homing endonuclease site (HE) and at least one restriction enzyme site (X) wherein the HE and X sites are selected such that HE and X result in compatible cohesive ends when cut by the homing endonuclease and restriction enzyme, respectively, and the ligation product of HE and X cohesive ends can neither be cleaved by the homing endonuclease nor the restriction enzyme.

According to the present invention, the terms "nucleic acid" and "polynucleotide" are used interchangeably and refer to DNA, RNA or species containing one or more nucleotide analogues. Preferred nucleic acids or polynucleotides according to the present invention are DNA, most preferred double-stranded (ds)DNA.

Preferably, the nucleic acid of the present invention has the following sequence elements:
HE-Prom-MCS-Term-X or HE-Prom-MCS-X
wherein
Prom: represents a promoter;
MCS: represent a multiple cloning site; and
Term: represents a terminator.

The above arrangement is hereinafter often referred to as "multiple integration element" (MIE).

Promoters useful in the present invention include, but are not limited to, promoters of prokaryotic, viral, mammalian, or insect cell origin or a combination thereof. Likewise, terminators useful in a nucleic acid according to the invention include, but are not limited to, terminators of prokaryotic, viral, mammalian, insect cell origin or a combination thereof. The term "multiple cloning site" according to the present invention means a sequence having at least one restriction enzyme site different from the site X as defined above. The MCS according to the present invention may, e.g. be derived from the multiple cloning sites of any commercially available plasmid.

Preferred prokaryotic promoters are Lac, T7, arabinose and trc promoters. Further promoters useful in the context of the present invention are viral promoters, in particular baculoviral promoters such as polh, p10 and $p_{XIV}$ very late baculoviral promoters, vp39 baculoviral late promoter, vp39 polh baculoviral late/very late hybrid promoter, $P_{cap/polh}$, pcna, etl, p35, egt, da26 baculoviral early promoters. Further promoters useful in the context of the present invention are the promoter sequences CMV, SV40, UbC, EF-1α, RSVLTR, MT, $P_{DS47}$, Ac5, $P_{GAL}$ and $P_{ADH}$.

Examples of terminator sequences useful in the context of the present invention are T7, SV40, HSVtk or BGH.

The multiple cloning site according to the present invention may contain, in addition to the at least one restriction enzyme site (other than X), one or more, especially 1 to 4 homology regions. The restriction enzymes sites contained in the MCS can easily be chosen by the skilled person and examples of such sites together with their recognition sequences can be taken from the latest product catalogue of New England Biolabs, Ipswich, Mass., USA.

A "homing endonuclease" according to the present invention is a DNase specific for double-stranded DNA having a large, isometric recognition site of e.g. 12-40 base pairs or even more, preferably 20 to 30 base pairs. For a recent review with regard to homing endonucleases, see Stoddard B. L. (2005) Q. Rev. Biophys. 38, 49-95. Due to the length of HE recognition sequences it is highly unlikely that a corresponding site occurs in the nucleotide sequence of a gene or polygene (or any other nucleotide sequence of any origin) to be inserted into the constructs according to the present invention making this strategy particularly useful for cloning larger and/or many genes of interest ("GOI").

A preferred HE site according to the present invention is a recognition sequence of a homing endonuclease that results in a 4 nucleotide overhang when cut by the respective homing endonuclease.

Examples of such HE sites include, but are not limited to, recognition sequences of PI-SceI, I-CeuI, I-PpoI, I-HmuI I-CreI, I-DmoI, PI-PfuI and I-MsoI, PI-PspI, I-SceI, other LAGLIDAG group members and variants thereof, SegH and Hef or other GIY-YIG homing endonucleases, I-ApeII, I-AniI, Cytochrome b mRNA maturase bl3, PI-TliI and PI-TfuII, PI-ThyI and others; see also Stoddard (2005), supra.

A preferred restriction enzyme site X according to the present invention compatible with HE sites producing a 4 bp overhang (examples are given above) is a BstXI site.

Corresponding enzymes are commercially available, e.g. from New England Biolabs Inc., Ipswich, Mass., USA.

Especially preferred MIEs of the invention containing prokaryoutic promoters/terminators have one of the following structures:
I-CeuI-T7 Prom-MCS-T7 Term-BstXI
PI-SceI-T7 Prom-MCS-T7 Term-BstXI Especially preferred MIEs of the invention containing baculoviral promoters have one of the following structures:
I-CeuI-p10-MCS-BstXI
PI-SceI-p10-MCS-BstXI
I-CeuI-polh-MCS-BstXI
PI-SceI-polh-MCS-BstXI Particularly preferred examples of nucleic acids according to the present invention comprise the sequence according to SEQ ID NO: 1 (for a detailed map see FIGS. 13A and B; the sequence antisense to SEQ ID NO: 1 is outlined in SEQ ID NO: 54), SEQ ID NO: 50 (restriction map: FIG. 42), SEQ ID NO: 51 (restriction map: FIG. 43), SEQ ID NO: 52 (restriction map: FIG. 44) or SEQ ID NO: 53 (restriction map: FIG. 45).

In preferred embodiments of the present invention, the above-defined nucleic acid additionally comprises at least one site for integration of the nucleic acid into a vector or host cell. The integration site may allow for a transient or genomic incorporation.

With respect to the integration into a vector, in particular into a plasmid or virus, the integration site is preferably compatible for integration of the nucleic acid into an adenovirus, andeno-associated virus (AAV), autonomous parvovirus, herpes simplex virus (HSV), retrovirus, rhadinovirus, Epstein-Barr virus, lentivirus, semliki forest virus or baculovirus.

Particularly preferred integration sites that may be incorporated into the nucleic acid of the present invention can be selected from the transposon element of Tn7, λ-integrase specific attachment sites and site-specific recombinases (SSRs), in particular LoxP site or FLP recombinase specific recombination (FRT) site. Further preferred mechanisms for integration of the nucleic acid according to the invention are specific homologous recombination sequences such as lef2-603/Orf1629.

In further preferred embodiments of the present invention, the nucleic acid as described herein additionally contains one or more resistance markers for selecting against otherwise toxic substances. Preferred examples of resistance markers useful in the context of the present invention include, but are not limited to, antibiotics such as ampicillin, chloramphenicol, gentamycin, spectinomycind, and kanamycin resistance markers.

The nucleic acid of the present invention may also contain one or more ribosome binding site(s) (RBS), preferably integrated into an MIE as defined above.

Further subject-matter of the present invention relates to a vector comprising a nucleic acid as defined above.

Preferred vectors of the present invention are plasmids, expression vectors, transfer vectors, more preferred eukaryotic gene transfer vectors, transient or viral vector-mediated gene transfer vectors. Other vectors according to the invention are viruses such as adenovirus vectors, adeno-associated virus (AAV) vectors, autonomous parvovirus vectors, herpes simples virus (HSV) vectors, retrovirus vectors, rhadinovirus vectors, Epstein-Barr virus vectors, lentivirus vectors, semliki forest virus vectors and baculovirus vectors.

Baculovirus vectors suitable for integrating a nucleic acid according to the invention (e.g. present on a suitable plasmid such as a transfer vector) are also subject matter of the present invention and preferably contain site-specific integration sites such as a Tn7 attachment site (which may be embedded in a lacZ gene for blue/white screening of productive integration) and/or a LoxP site. Further preferred baculovirus according to the invention contain (alternative to or in addition to the above-described integration sites) a gene for expressing a substance toxic for host flanked by sequences for homologous recombination. An example for a gene for expressing a toxic substance is the diphtheria toxin A gene. A preferred pair of sequences for homologous recombination is e.g. Isf2-603/Orf1629. The baculovirus can also contain further marker gene(s) as described above, including also fluorescent markers such as GFP, YFP and so on. Specific examples of corresponding baculovirus of the invention have the structure of EMBac, EMBAcY, EMBac_Direct and EMBAcY_Direct as disclosed in the schemes according to FIGS. 38, 39, 40 and 41, respectively.

Vectors useful in prokaryotic host cells comprise, preferably besides the above-exemplified marker genes (one or more thereof), an origin of replication (ori). Examples are BR322, ColE1, and conditional origins of replication such as OriV and R6Kγ, the latter being a preferred conditional origin of replication which makes the propagation of the vector of the present application dependent on the pir gene in a prokaryotic host. OriV makes the propagation of the vector of the present application dependent on the trfA gene in a prokaryotic host.

Furthermore, the present invention is directed to a host cell containing the nucleic acid of the invention and/or the vector of the present invention.

The host cells may be prokaryotic or eukaryotic. Eukaryotic host cells may for example be mammalian cells, preferably human cells. Examples of human host cells include, but are not limited to, HeLa, Huh7, HEK293, HepG2, KATO-III, IMR32, MT-2, pancreatic β-cells, keratinocytes, bone-marrow fibroblasts, CHP212, primary neural cells, W12, SK-N-MC, Saos-2, WI38, primary hepatocytes, FLC4, 143TK, DLD-1, embryonic lung fibroblasts, primery foreskin fibroblasts, MRC5, and MG63 cells. Further preferred host cells of the present invention are porcine cells, preferably CPK, FS-13, PK-15 cells, bovine cells, preferably MDB, BT cells, bovine cells, such as FLL-YFT cells. Other eukaryotic cells useful in the context of the present invention are *C. elegans* cells. Further eukaryotic cells include yeast cells such as *S. cerevisiae, S. pombe, C. albicans* and *P. pastoris*. Furthermore, the present invention is directed to insect cells as host cells which include cells from *S. frugiperda*, more preferably Sf9, Sf21, Express Sf+, High Five H5 cells, and cells from *D. melanogaster*, particularly S2 Schneider cells. Further host cells include *Dictyostelium discoideum* cells and cells from parasites such as *Leishmania* spec.

Prokaryotic hosts according to the present invention include bacteria, in particular *E. coli* such as commercially available strains like TOP10, DH5α, HB101 etc.

The person skilled in the art is readily able to select appropriate vector construct/host cell pairs for appropriate propagation and/or transfer of the nucleic acid elements according to the present invention into a suitable host. Specific methods for introducing appropriate vector elements and vectors into appropriate host cells are equally known to the art and methods can be found in the latest edition of Ausubel et al. (ed.) Current Protocols In Molecular Biology, John Wiley & Sons, New York, USA.

In preferred embodiments of the present invention, the vector as defined above additionally comprises a site for site specific recombinases (SSRs), preferably one or more LoxP sites for Cre-lox specific recombination. In further preferred embodiments, the vector according to the present invention comprises a transposon element, preferably a Tn7 attachment site.

It is further preferred that the attachment site as defined above is located within a marker gene. This arrangement makes it feasible to select for successfully integrated sequences into the attachment site by transposition. According to preferred embodiments, such a marker gene is selected from luciferase, β-GAL, CAT, fluorescent encoding protein genes, preferably GFP, BFP, YFP, CFP and their variants, and the lacZα gene.

Particularly preferred embodiments of the vector according to the present invention have a sequence selected from the group consisting of SEQ ID NO: 2 to SEQ ID NO: 17.

Further preferred embodiments of the present invention are vectors containing more than one of the sequence elements of the nucleic acids of the present invention as defined above and, optionally, additionally containing more than one recombination sequence for a site specific recombinase, e.g. 2 to 6, more preferred 2, 3 or 4 of such recognition sequences, preferably 2 to 6, especially preferred 1 to 4 loxP sites.

A particularly preferred example of such a vector has the sequence of SEQ ID NO. 18.

It is to be understood that, if the vector of the present invention contains more than one recombination sequences, these can be recognition sequences of the same or different site-specific recombinases.

Further subject-matter of the present invention is a kit for cloning and/or expression of multiprotein complexes containing at least one vector as defined above together with at least host cell suitable for the propagation of said vector(s). Preferred host cells have been already described above. Preferably, the kit of this aspect of the present invention additionally contains a site-specific recombinase such as Cre.

The present invention also relates to a method for producing a vector containing multiple expression cassettes comprising the steps of:
(a) inserting one or more genes between the HE and the X site of a first vector of the present invention;
(b) inserting one or more genes between the HE and the X site of a second vector as defined herein;
(c) cleaving the first vector with a homing endonuclease specific for site HE and with a restriction enzyme specific for site X yielding a fragment containing the at least one gene flanked by the cleaved HE and X sites;
(d) cleaving the second vector with a homing endonuclease specific for site HE;
(e) ligating the fragment obtained in step (c) into the cleaved second vector obtained in step (d) generating a third vector; and optionally
(f) repeating steps (a) to (e) with one or more vector(s) generating a vector containing multiple genes.

According to preferred embodiments of the present invention it is possible to insert one or more genes into the vectors of the invention by methods known to the skilled person, e.g. by restriction enzyme digestion/ligation via compatible sites within the MCS or by recombination, preferably using the optionally present homology region(s), preferably using the SLIC method. If more than one gene is inserted, these can be provided as single expression cassettes. However, it is clear for the skilled person that the (several or multiple) genes can be present as a polygene within in one ORF.

The present invention is further directed to a method for producing multiple protein complexes comprising the steps of
(i) producing a vector containing multiple expression cassettes by the method as defined above;
(ii) introducing the vector obtained in step (i) into a suitable host cells such as the host cells described above; and
(iii) incubating the host cell under conditions allowing the simultaneous expression of the genes present in the vector.

The introduction of the vector into suitable host cells (as exemplified above) is carried out by methods known to the skilled person (see, e.g. Ausubel et al. (ed.), supra).

A further aspect of the present application is a fusion vector comprising n vector entities separated from each other by n of the same site-specific recombination site wherein each vector entity contains an individual resistance marker gene different from the resistance marker genes of the other vector entities, wherein n is an integer of at least 3.

A "single vector" or "vector entity" according to the present aspect of the invention is generally a nucleic acid suitable for integration of foreign genetic elements (in particular, one or more genes of interest) into host cells and which are suited for amplification. Typical examples are plasmids, bacmids, viruses, lambda vectors, cosmids etc. Preferred examples of one or more of the above vector categories are outlined in more detail above with respect to the HE/X site containing vector which definitions are also valid for this aspect of the present invention.

It is clear for the skilled person that the number of vector entities to be assembled into a fusion vector according to the present invention (or disassembled from such a fusion vector; with respect to methods of assembly/disassembly see below)

is generally not specifically limited as long as a corresponding number of resistance markers is available. With respect to practical considerations, the number n in the context pf the present invention is preferably 3, 4, 5 or 6, (but may be more) which in part depends on the size of constructs that can be propagated in the host.

The present invention furthermore relates to a kit for assembly and/or disassembly of n vectors comprising
a fusion vector comprising n vector entities separated from each other by n of the same site-specific recombination site wherein each vector entity contains an individual resistance marker gene different from the resistance marker genes of the other vector entities; and/or
n vectors (vector entities) each containing a site-specific recombination site and an individual resistance marker gene different from the resistance marker genes of the other vectors,
wherein n is an integer of at least 3; and
a recombinase specific for said site-specific recombination site and/or cells for the propagation of said fusion vector and/or said n vectors.

Preferred embodiments of the above fusion vector and vector kits are or contain, respectively, fusion vector(s) and/or vector entities comprising LoxP sites and Cre as the corresponding recombinase enzyme. Other examples of site-specific recombination sites/recombinases are FRT sites and the corresponding enzyme (FLP recombinase).

According to a preferred embodiment the above-defined n vectors or vector entities, respectively, each contain one or more expression cassettes of the form Prom-MCS-Term or Prom-MCS-Term (definitions are as defined above, preferably between a HE and restriction enzyme site X as defined above). It is further preferred that the expression cassette preferably present in the vectors or vector entities, respectively, contains one or more genes of interest ("GOI").

Examples of resistance marker genes (or simply "resistance markers") useful in the context of this aspect of the present invention are as already defined above.

An especially preferred example of the fusion vector as defined above is vector pACKS (SEQ ID NO: 18) described in more detail below.

Preferred examples of the vector entities are pACE (SEQ ID NO: 2), pACE2 (SEQ ID NO: 3), pDC (SEQ ID NO: 4), pDK (SEQ ID NO: 5) and pDS (SEQ ID NO: 6), which are all adapted for expression in prokaryotic hosts, and pIDC (SEQ ID NO: 7), pIDK (SEQ ID NO: 8), pIDS (SEQ ID NO: 9), pACEBac1 (SEQ ID NO: 10), pACEBac2 (SEQ ID NO: 11), pACEBac3 (SEQ ID NO: 12), pACEBac4 (SEQ ID NO: 13), pOmniBac1 (SEQ ID NO: 14), pOmniBac2 (SEQ ID NO: 15, pOmniBac3 (SEQ ID NO: 16) and pOmniBac4 (SEQ ID NO: 17), which are tailored for expression in insect cells using baculovirus. The above preferred examples of vector entities are described in more detail below.

It is further preferred that at least one of the vector entities (and/or of the individual vectors in the above kit) contains a further selectable marker different from the resistance marker genes. An example is a conditional origin of replication making the propagation of the respective vector entity dependent on a specific genetic background in a host. An example is an Ori derived from (or being) R6kγ making the propagation of the vector dependent on the pir gene.

The present invention further provides a method for assembling n vector entities into 1 to (n−1) fusion vectors wherein said fusion vector(s) contain(s) 2 to n of said vector entities comprising the steps of:
(1) contacting n vector entities each containing a site-specific recombination site and an individual resistance marker different from the resistance markers of the other vector entities with a recombinase specific for said site-specific recombination site so as to generate a mixture of fusions of the vector entities comprising 2 to n of said vector entities,
(2) transforming said mixture into host cells;
(3) culturing one or more sample(s) of the transformed cells in the presence of the appropriate combination of antibiotics for selecting a desired fusion vector containing 2 to n vector entities.
(4) obtaining n single clones of transformed cells from the culture obtained in step (3) in which these were viable in the presence of the respective combination of antibiotics; and
(5) culturing n samples of each of said n single clones in the presence of each of n antibiotics specific for the n individual resistance markers present in said n vector entities;
wherein n is as defined above.

If it is desired to select for more than one desired vector fusions, the transformed cells obtained in above step (2) are divided into the appropriate number of aliquots or samples. For example, if it is desired to select all possible (n!-n) vector fusions (i.e. the single vector entities as educts of the above method are not selected for), the transformed host cells are divided into (n!-n) aliquots (or samples) and each aliquot is cultured in the presence of the appropriate antibiotics.

In the context of the present invention, the term "aliquot" as used herein does not necessarily mean that the aliquots have the same volume or number of cells. Rather, each of the aliquots or samples may have the same or different volumes or number of cells.

The term "culturing" the transformed cells or the aliquot (or sample) means that the transformed cells are incubated under the appropriate conditions for viability of the host cells. For example, the transformed host cells may be used to inoculate a (e.g. larger) volume of liquid culture medium or the aliquot may be plated out on an appropriate solid medium.

If the vector assembly method as defined above is used to select for more than one desired vector fusion, e.g. if all possible fusions are desired, the selection step (3) is preferably carried out using typical well plate formats such as 96-well plates.

According to a preferred embodiment of the present vector assembly method each of the vector entities to be fused each contains a further selectable marker different from the resistance marker. Such vector entities are hereinafter referred to as "Donor" vectors, since, when fused to a vector entity which does not contain said selectable marker different from the resistance marker (hereinafter referred to as "Acceptor"), in a fusion between the Donor(s) and the Acceptor, said Donor(s) provide host cells with a phenotype that allows only the propagation of Acceptor-Donor fusions but not Donor-Donor fusions. Preferred examples of such a selectable marker are conditional origins of replication making the propagation of the Donor dependent on a specific genetic background. A specific example of such a selectable marker is R6Kγ Ori making the propagation of the Donor dependent on the presence of the pir gene in a bacterial host such as *E. coli*. In this case, the mixture obtained in step (i) of the above vector assembly method is transformed into bacterial cells lacking the pir gene (such *E. coli* strains TOP10, DH5α, HB101 or other commercially available pir⁻ cells).

A preferred embodiment of the above-defined vector assembly method is described in more detail below (ACEMBL system; Section C.2.1)

According to a preferred embodiment of the above-defined method, the n vector entities, respectively, each contain one or more expression cassettes of the form Prom-MCS-Term or Prom-MCS (as defined above, preferably between a HE and restriction enzyme site X as defined above). It is further preferred that the expression cassette preferably present in the vectors or vector entities, respectively, contains one or more genes of interest ("GOI") to be expressed in a suitable host.

Another method for providing fusion vectors according to the present invention is a sequential assembly process wherein in the first step two of the vector entities are recombined, transformed into host cells and the host cells cultured in the presence of two antibiotics. The second round comprises the isolation of the double fusion vector (n=2) from a viable clone, contacting with a third vector entity in the presence of the respective recombinase, transformation into host cells and selection for the three resistance markers present in the triple fusion vector (n=3) and so on until the desired multifusion vector is reached.

Of course, it is also possible to provide fusion vectors according to the invention, in particular fusion vectors of higher order (i.e. n>3) by a combined approach using the vector assembly method of steps (1) to (5) as defined above (e.g. for assembling a fusion vector with n=3, 4 or 5) and then adding one or more further vector entities sequentially as described in the previous paragraph.

The principle underlying the above-described method for assembling a fusion vector, i.e. the equilibrium of educts and products in recombination reactions, can equally be applied to the disassembly of fusion vectors.

Therefore, the invention further provides a method of disassembling a fusion vector containing n vector entities into one or more desired fusion vectors selected from the group consisting of fusion vectors containing 2 to (n−1) vector entities or into one or more desired single vector entities, wherein in said fusion vector containing n vector entities said n vector entities are separated from each other by n site-specific recombination sites and each vector entity contains an individual resistance marker different from the resistance markers of the other vector entities, comprising the steps of:
(A) contacting the fusion vector containing n vector entities with a recombinase specific for said site-specific recombination sites in order to generate a mixture of fusion vectors comprising 2 to (n−1) of said vector entities and single vector entities;
(B) transforming said mixture into host cells; and
(C) culturing one or more sample(s) of the transformed cells in the presence of
(C1) an appropriate combination of antibiotics for selecting one or more desired fusion vector(s) containing 2 to (n−1) vector entities; and/or
(C2) a single appropriate antibiotic for selecting a desired single vector entity;
(D) obtaining n single clones of transformed cells from the sample of the transformed cells in which these were viable in the presence of the respective antibiotic or combination of antibiotics, respectively; and
(E) culturing n samples of each of said n single clones in the presence of each of n antibiotics specific for the n individual resistance markers present in said n vector entities;
wherein n is as defined above.

If it is desired to select for single vectors using the above fusion vector disassembly method, it is preferred that steps (A), (B) and (C1) to (E) are carried out for selecting an appropriate fusion vector containing 2 to (n−1) vector entities and then to perform steps (A), (B) and (C2) to (E) are carried out with said selected fusion vector containing 2 to (n−1) vector entities. It is understood that this sequential approach can be repeated which is especially preferred when starting from a fusion vector containing a higher number of vector entities, i.e. one can select for a (n−1) fusion vector in the first, then for a (n−2) construct in the second round and so on, e.g. until reaching a fusion vector with n=3 or 2 such that the presence of the single vector entities in the recombinase reaction equilibrium makes the selection of respective clones containing said single vector entities according to the selection steps (C2) to (E) more likely.

Furthermore, in analogy to the above-defined vector assembly method, it is preferred in the fusion vector disassembly method of the present invention that (n−1) of the vector entities in said fusion vector containing n vector entities each contains a further selectable marker different from the resistance markers such that only host cells transformed with fusions between a vector entity not containing the further selectable marker and one or more of the vector entities containing the selectable marker are viable in step (C1).

With respect to preferred selectable markers (conditional Ori etc.), host cells, the use of multi well test plates etc. it is referred to the preferred embodiments of the vector assembly method outlined above.

The fusion vector disassembly method of the present application is further elaborated below with respect to a preferred embodiment (ACEMBL system; Section C.2.2).

The nucleic acids and vectors (including fusion vectors and single vectors (i.e. vector entities)) of the present invention may contain further typical sequence elements, e.g. elements that enable or simplify the detection and/or purification of the (multiple) proteins expressed from the one or more genes of interest. Typical examples of such elements are sequences coding for GFP and its derivatives, His-tags, GST etc.

Fusion vectors according to the present invention are advantageously used for the expression of mutliprotein complexes in a suitable host. Thus, the present invention further provides a corresponding process comprising transforming a fusion vector of the invention (containing vector entities having inserted one or more genes of interest, e.g. in form of multiple or single expression cassettes, or in the form of polygenes as appropriate) into a suitable host and culturing the transformed host under conditions allowing simultaneous expression of the genes of interest.

From the disclosure of the various aspects of the present invention the skilled person readily understands that the HE/X site polynucleotide (in particular corresponding vectors), preferably used for iterative cloning of multiple expression cassettes, can be combined with the assembly (or disassembly) methods as defined above for creating multigene constructs: For example, one or more of a single gene or multigene vector(s) can be prepared using the HE/X site elements as described which may then be assembled into fusion vectors of choice (e.g. triple, quadruple or higher order fusion vectors) using the recombination-based assembly methods defined herein. Such fusion vectors may then be (partly or completely) disassembled as disclosed herein and different constructs can be assembled in turn as appropriate for the respective multiprotein application envisaged by the skilled person. Thus, the aspects of the present invention represent a building block system which provides the person skilled in the art with a hitherto unknown freedom of combining multiple genes (or polygenes) of interest for multiprotein applications.

The figures show:

FIG. 1 shows a schematic overview of preferred vectors according to the present invention for expression of multiprotein complexes in prokaryotic hosts contained in a preferred kit called "ACEMBL".

Figure 3:
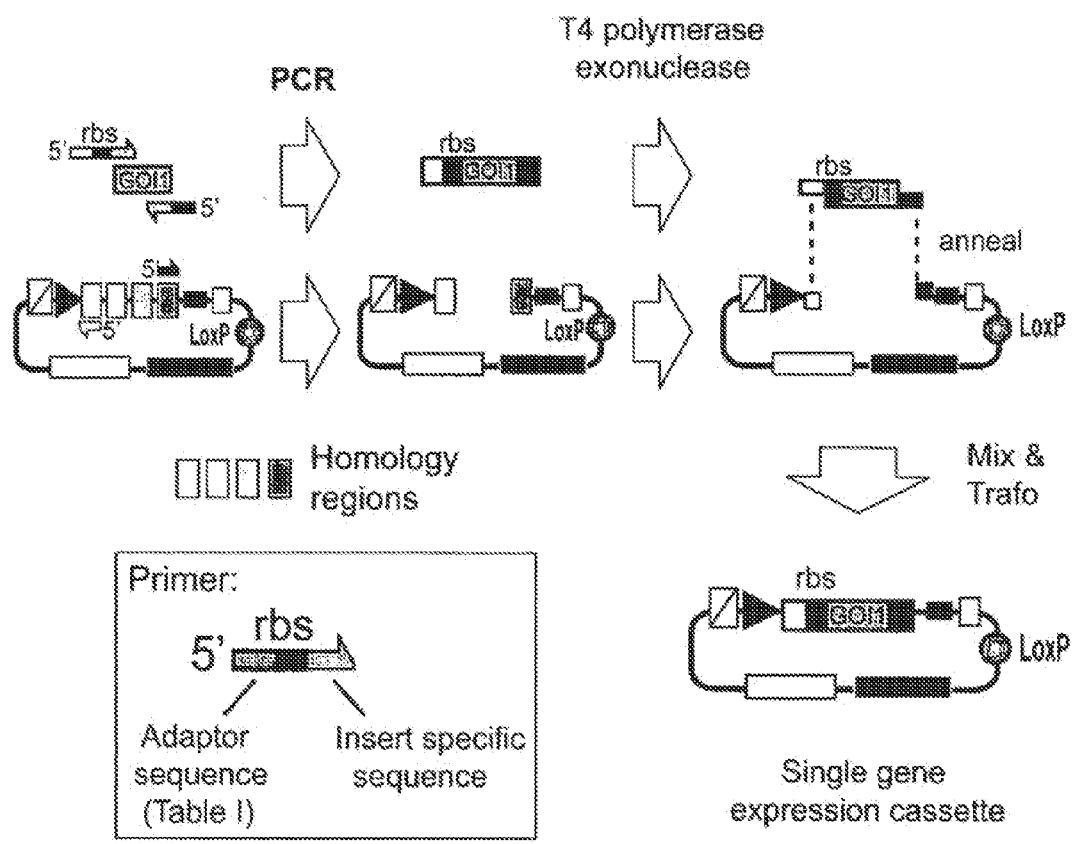

FIG. 3 shows a schematic overview of a preferred method for inserting a gene of interest ("GOI") into a vector of the present invention by sequence and ligation independent cloning (SLIC; see Tan, S. et al. *Protein Expr. Purif.* 40, 385 (2005)). A gene of interest (GOI 1) is PCR amplified with specific primers and integrated into a vector (Acceptor, Donor) linearized by PCR with complementary primers (complementary regions are shaded in light gray or dark grey, respectively). Resulting PCR fragments contain homology regions at the ends. T4 DNA polymerase acts as an exonuclease in the absence of dNTP and produces long sticky overhangs. Mixing (optionally annealing) of T4 DNA polymerase exonuclease treated insert and vector is followed by transformation, yielding a single gene expression cassette.

Figure 4:
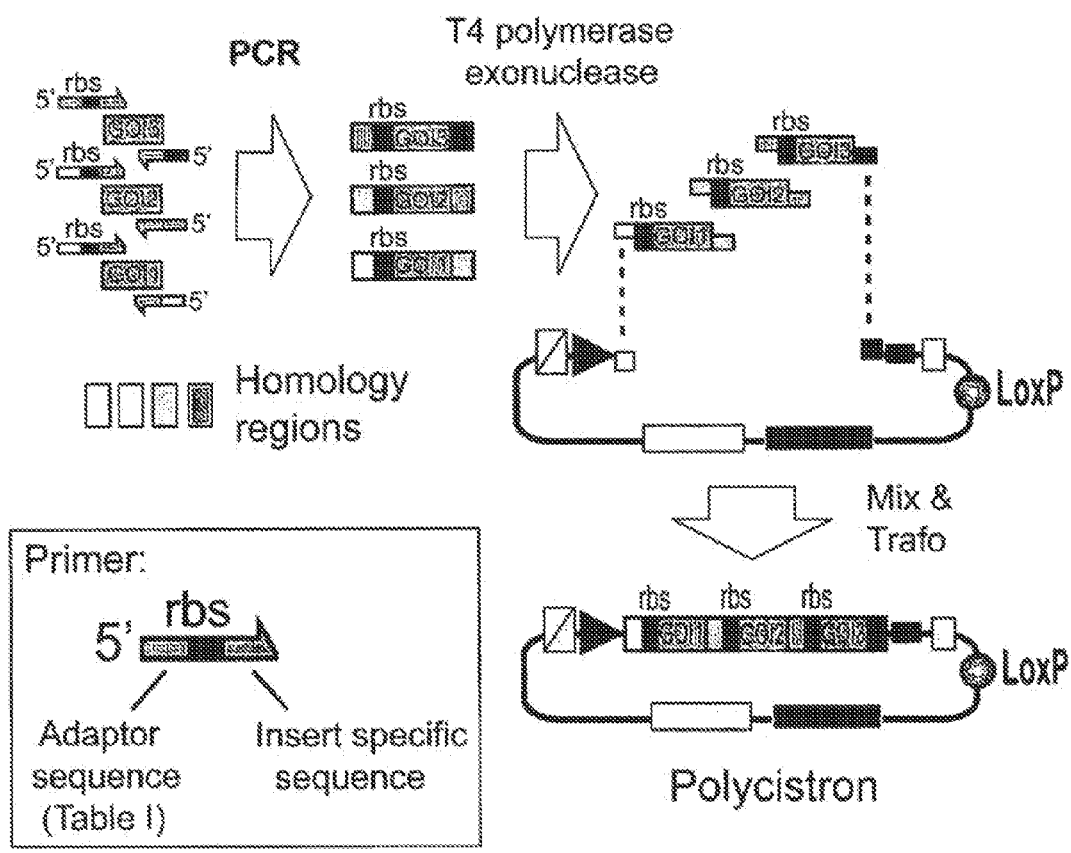

FIG. 4 shows a schematic overview of a preferred method for inserting a polycistron into a vector of the present invention by SLIC. Genes of interest (GOI 1, 2, 3) are PCR amplified with specific primers and integrated into a vector (Acceptor, Donor) linearized by PCR with primers complementary to the ends of the forward primer of the first (GOI 1) and the reverse primer of the last (GOI 3) gene to be assembled in the polycistron (complementary regions are shaded in light gray or dark grey, respectively). Resulting PCR fragments contain homology regions at the ends. T4 DNA polymerase acts as an exonuclease in the absence of dNTP and produces long sticky overhangs. Mixing (optionally annealing) of T4 DNA polymerase exonuclease treated insert and vector is followed by transformation, yielding a polycistronic expression cassette.

Figure 5:
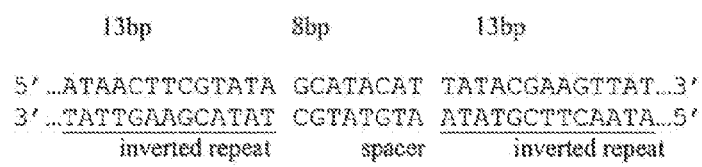

FIG. 5 shows the sequence of a LoxP imperfect inverted repeat (SEQ ID NO: 19).

Figure 6:
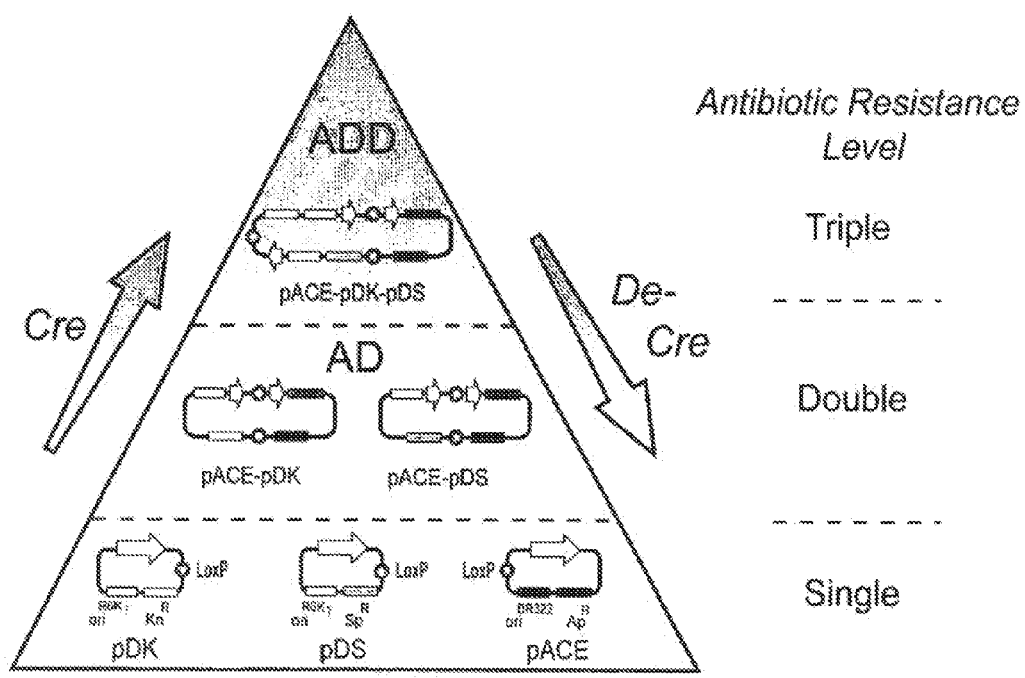

FIG. 6 (left panel) shows a schematic representation in form of a pyramid illustrating Cre-mediated assembly and disassembly of preferred embodiments of the vector of the present invention (pACE, pDK and pDS vectors). LoxP sites are shown as red circles, resistance markers and origins are labelled. White arrows stand for the entire expression cassette (including promoter, terminator and multiple integration elements) in the ACEMBL vectors. Not all possible fusion products are shown for clarity. Levels of multiresistance are indicated in the right panel.

Figure 7:
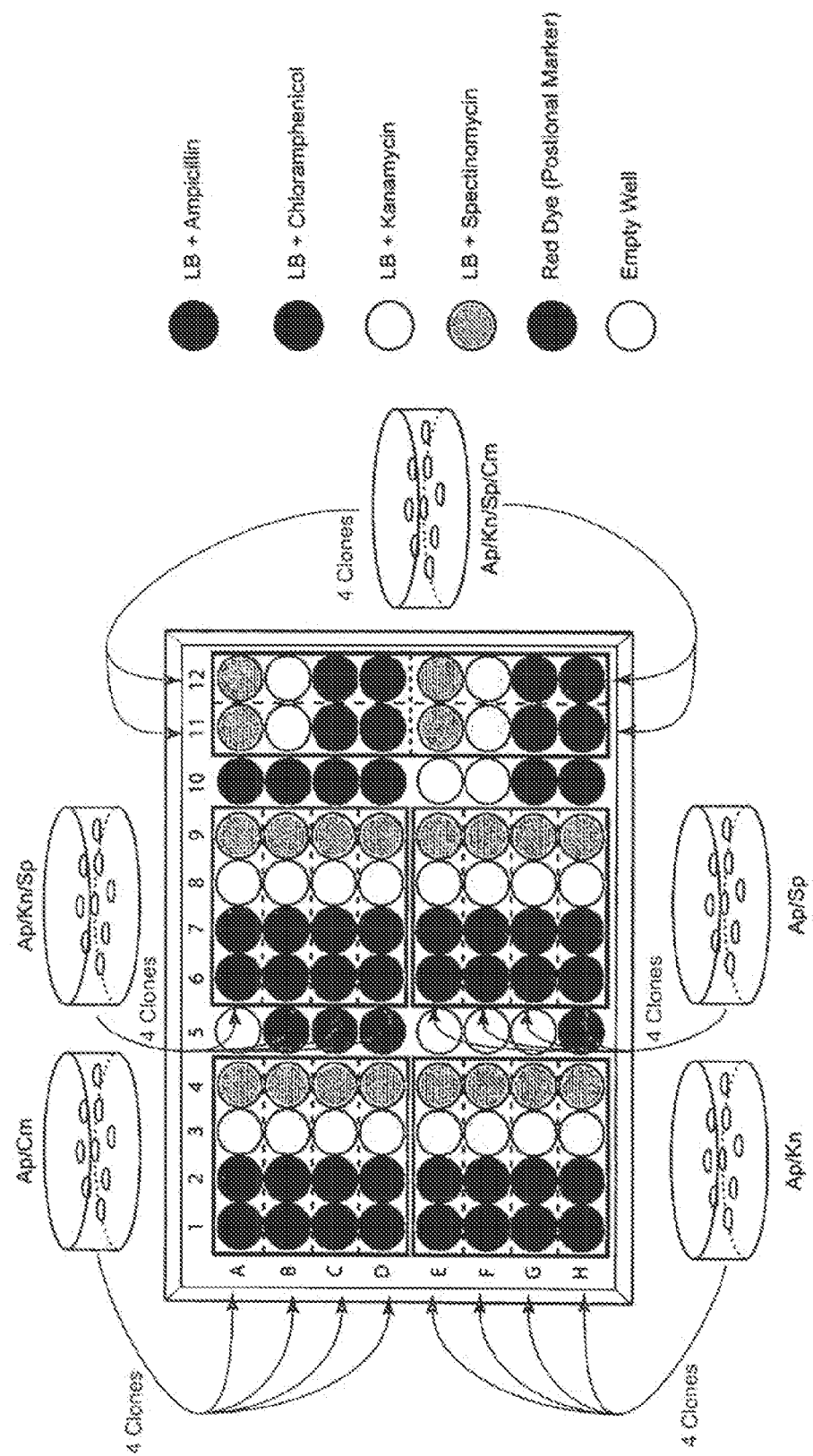

FIG. 7 is a schematic representation of a multiresistance analysis of bacterial colonies carrying vector constructs resulting from Cre-deCre assembly/disassembly according to the invention (cf. also FIG. 12).

Figure 8:
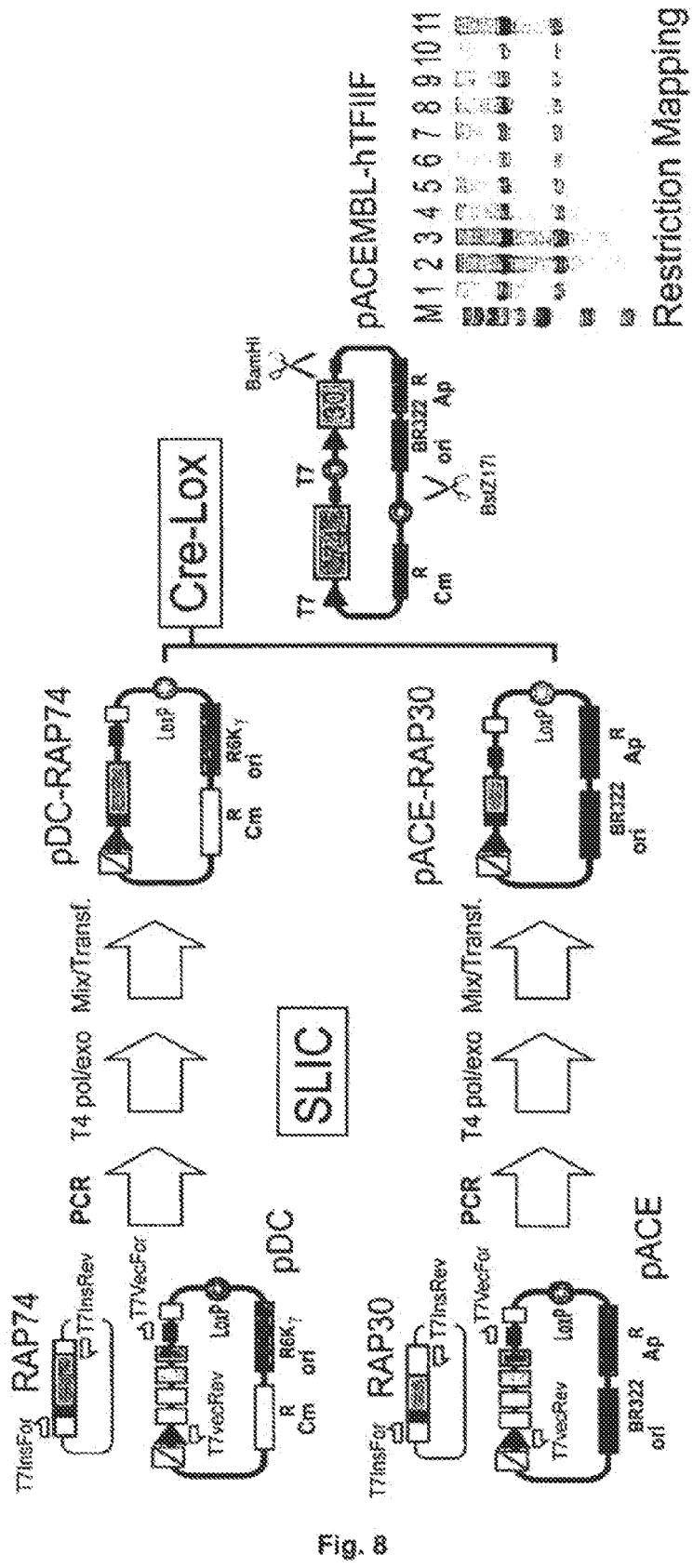

FIG. 8 shows a schematic representation of the strategy for cloning of human RAP74 and human RAP30 into vectors of the present invention for expression of human TFIIF (left panel). hRAP74 was cloned by SLIC into pDC. hRAP30 was cloned by SLIC into pACE. Cre-Lox recombination of pDC-RAP74 (donor) and pACE-RAP30 results in vector pACEMBL-hTFIIF. Results from restriction mapping by BstZ17I/BamHI double digestion of 11 double resistant (Cm, Ap) colonies are shown by a gel section from 1% E-gel electrophoresis (M: NEB 1 kb DNA marker). All clones tested showed the expected pattern (5.0+2.8 kb) (left panel).

Figure 9:
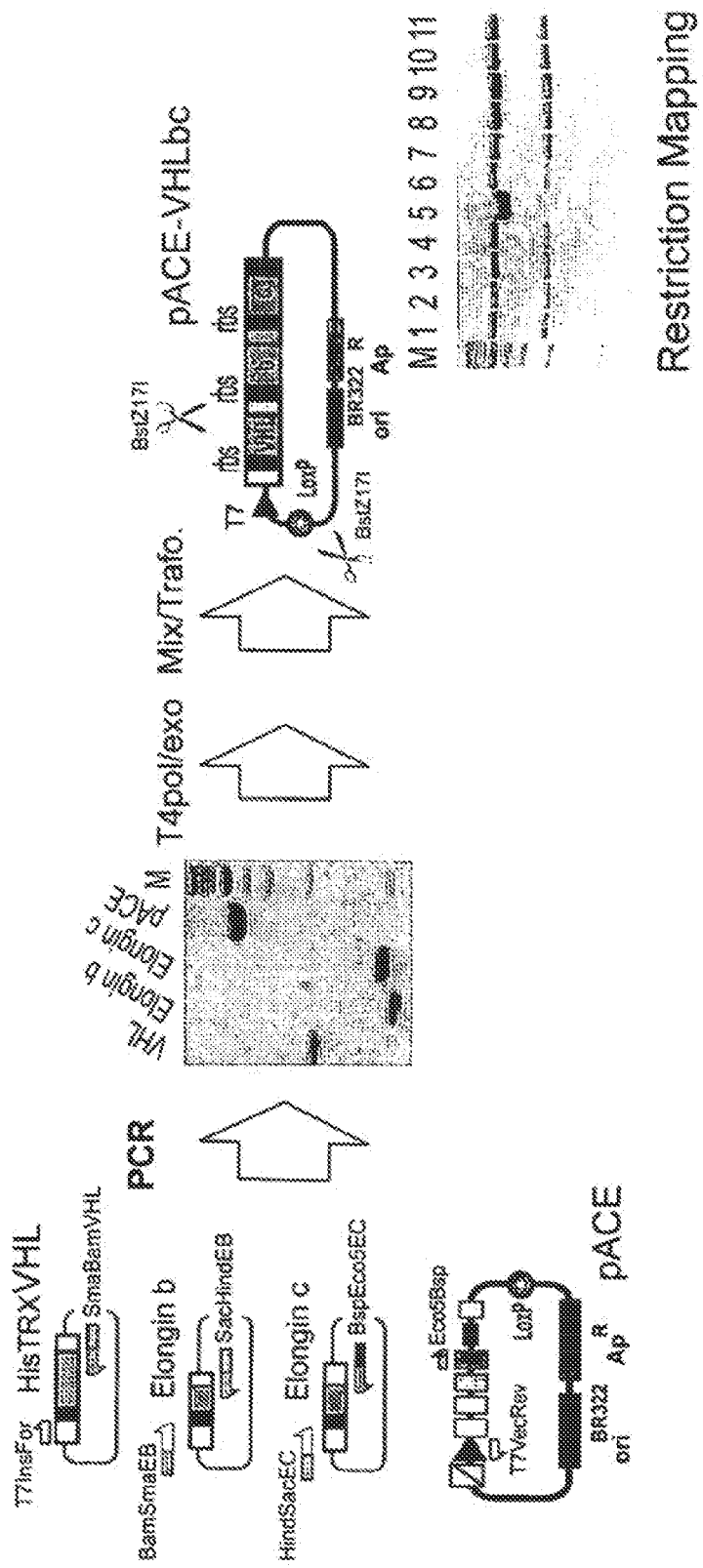

FIG. 9 illustrates the strategy for cloning of human VHL/elongin b/elongin c complex (VHLbc) (tricistron) into vector pACE by multifragment SLIC.

Figure 10:
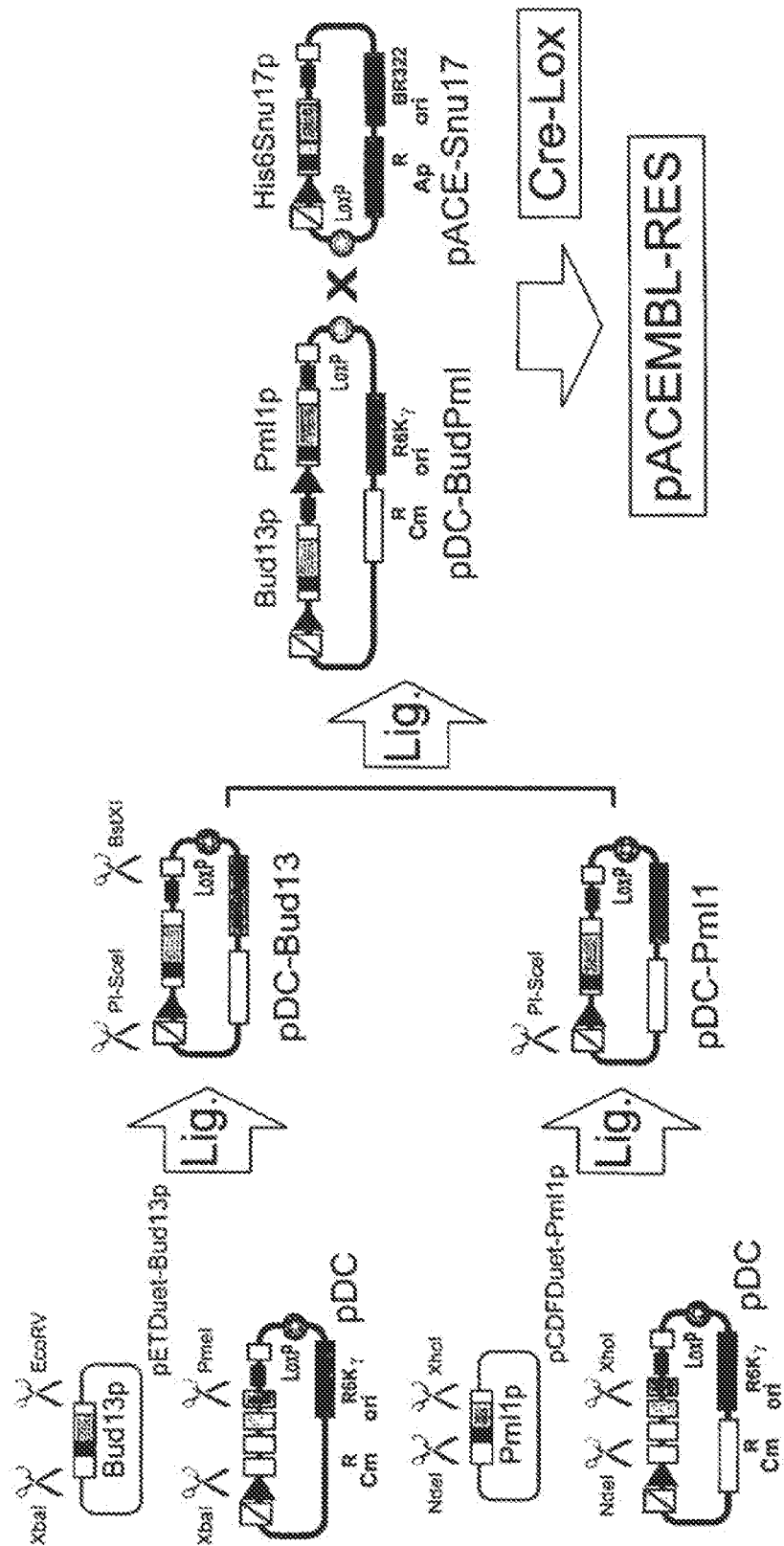

FIG. 10 shows a schematic representation of the strategy for iterative cloning of the components of yeast RES complex (Pml1p, Snu17p, Bud13p) using a preferred homing endonuclease site (HE)/restriction enzyme site (X) module (PI-SceI/BstXI) according to the present invention.

Figure 11:
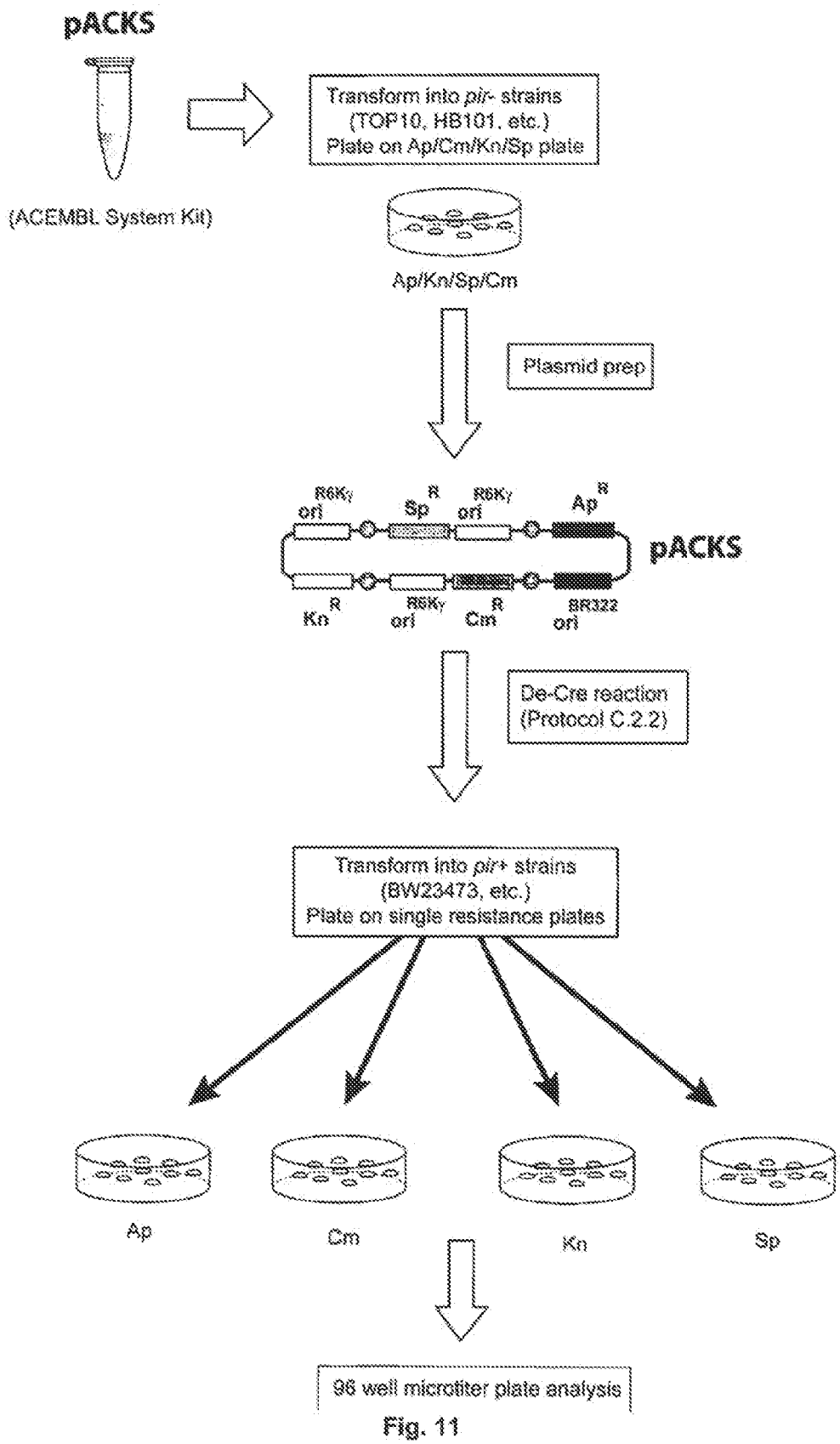

FIG. 11 shows a schematic representation of the generation of single vectors from multifusion vector pACKS (SEQ ID NO: 18).

FIG. 12 shows schematic representations and photographs illustrating a 96 well microtiter analysis of pACKS De-Cre reaction.

Figure 13A:
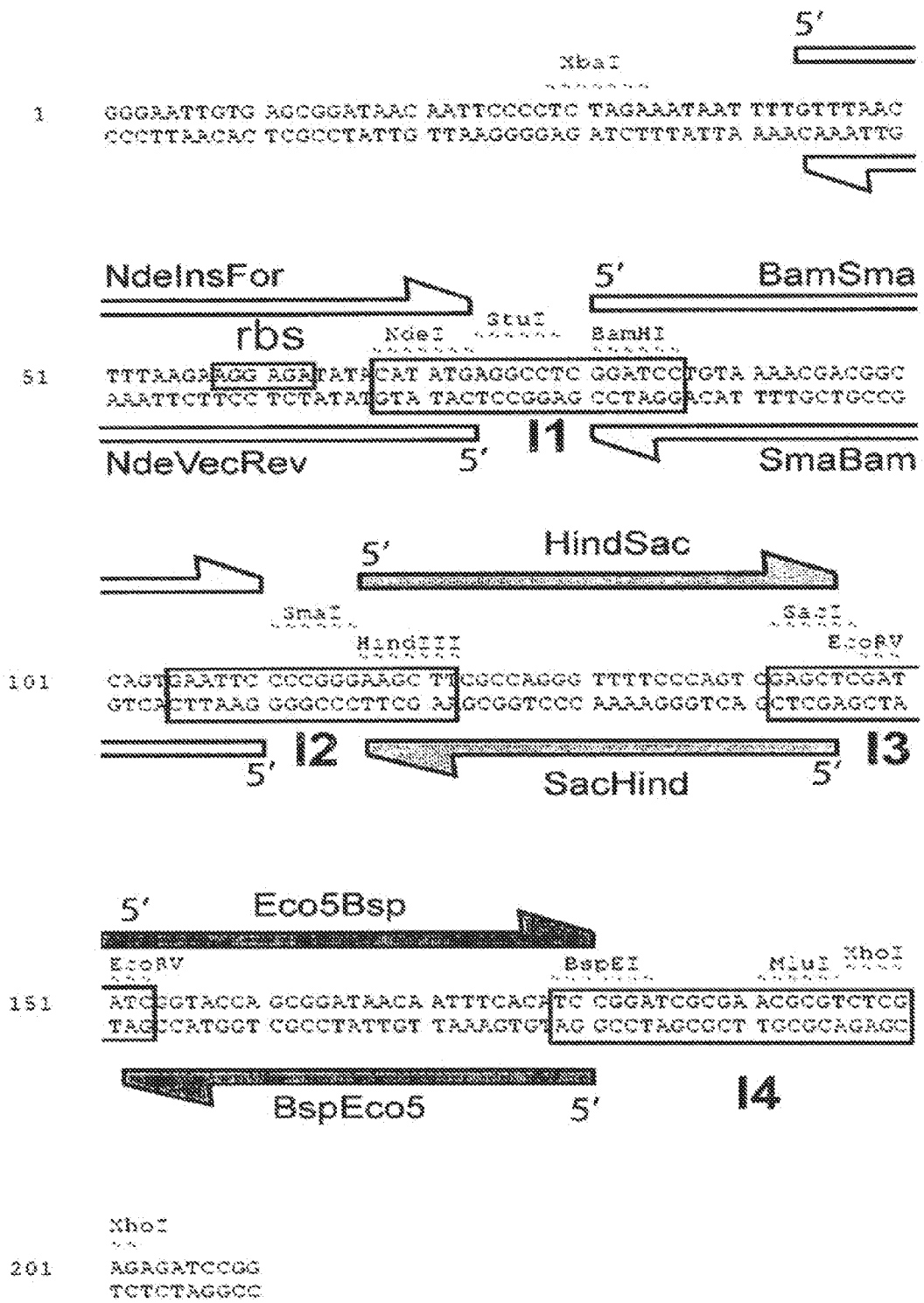
Figure 13B:
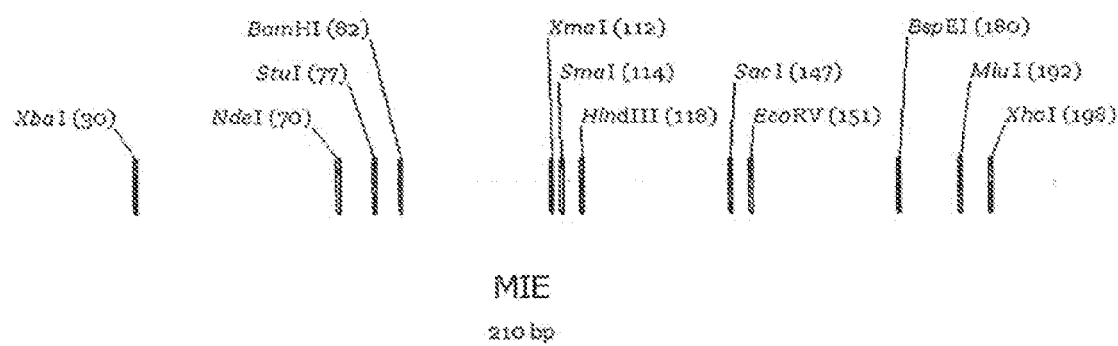

FIG. 13 shows the sequence and map of a preferred nucleic acid ("multiple integration element", MIE) according to the present invention (SEQ ID NO: 1). Forward and reverse primers for sequencing can be standard vector primers for T7 and lac. Adaptor primer sequences (see Table I) are indicated. DNA sequences in these homology regions contain tried-and-tested sequencing primers (Tan et al. (2005), supra). Sites of insertion (I1-I4) are shown. The adaptor sequences, and probably any sequence in the homology regions, can be used as adaptors for multifragment insertions. The ribosome binding site present in the MIE (rbs) is boxed in red.

Figure 14:
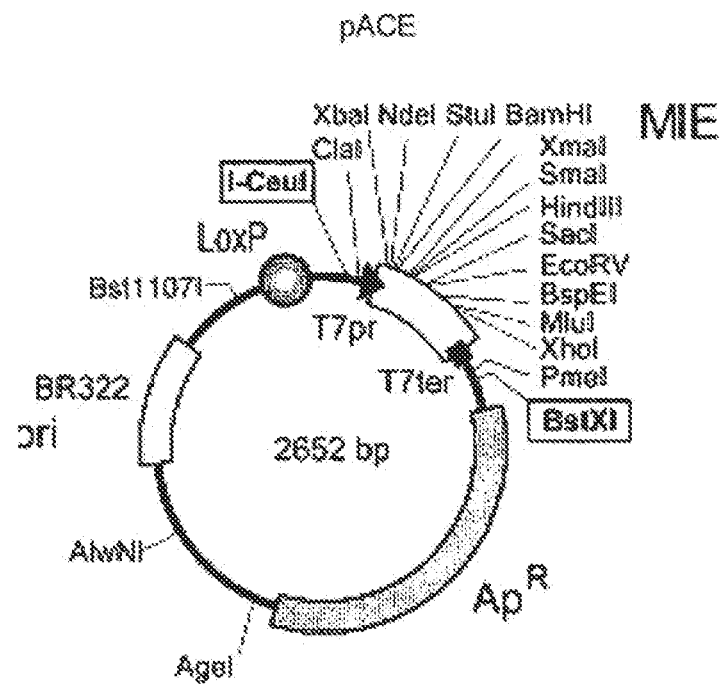
Figure 15:
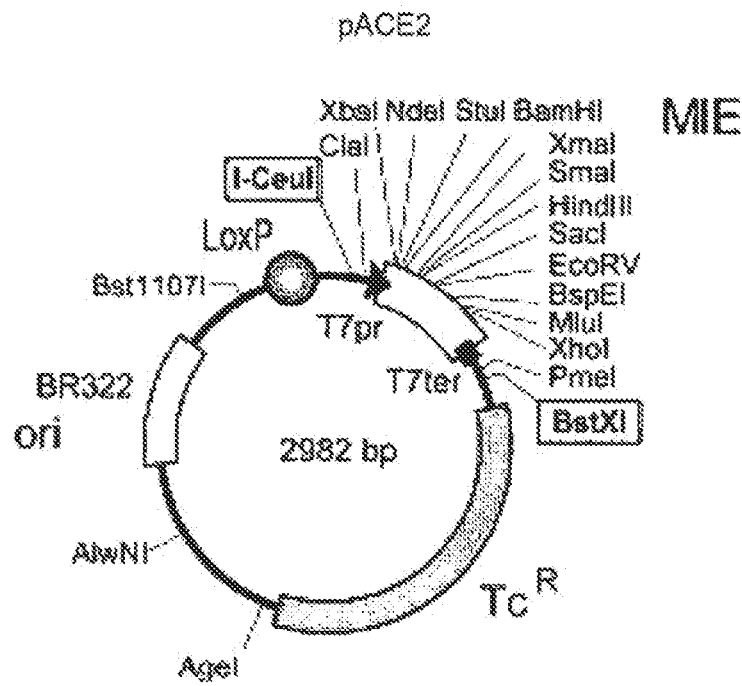
Figure 16:
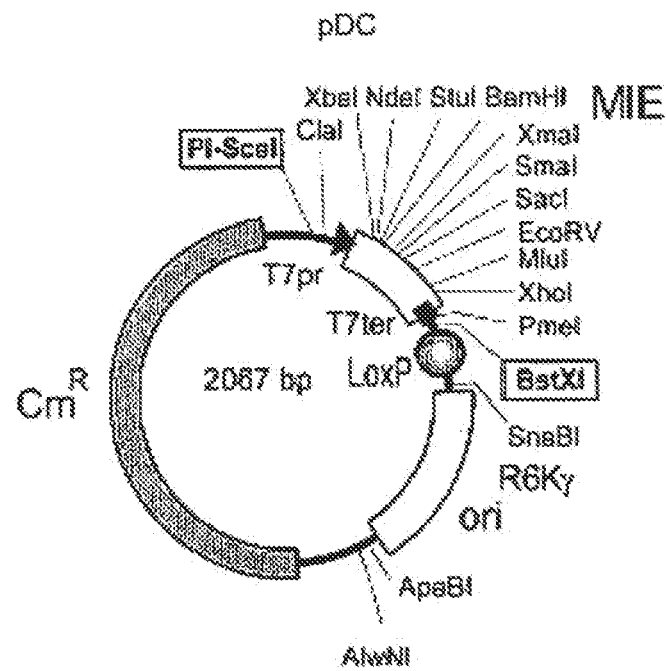
Figure 17:
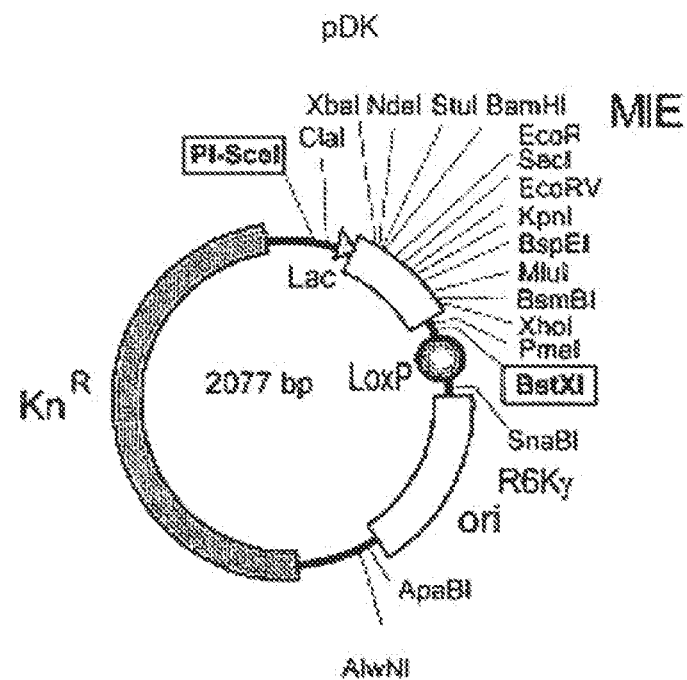
Figure 18:
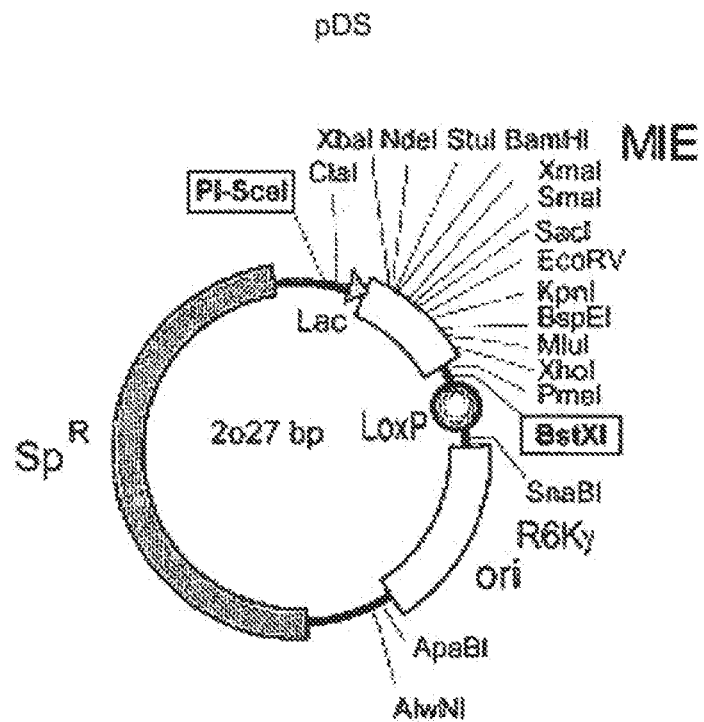

FIG. 14 shows a plasmid map of Acceptor vector pACE.
FIG. 15 shows a plasmid map of Acceptor vector pACE2.
FIG. 16 shows a plasmid map of Donor vector pDC.
FIG. 17 shows a plasmid map of Donor vector pDK.
FIG. 18 shows a plasmid map of Donor vector pDS.

As can be seen in the above plasmid maps, Acceptor vectors pACE (FIG. 14) and pACE2 (FIG. 15) contain a T7 promoter and terminator. Donor vectors pDC (FIG. 16), pDK (FIG. 17) and pDS (FIG. 18) contain conditional origins of replication. pDS (FIG. 18) and pDK (FIG. 17) have a lac promoter. pDC (FIG. 16) has a T7 promoter. Resistance markers and origins of replication are shown. LoxP imperfect inverted repeat sequences are shown as circles. Homing endonuclease sites and corresponding BstXI sites are boxed. The restriction enzyme sites in the multiple integration element (MIE) are indicated. All MIEs have the same DNA sequence between ClaI and PmeI. Differences in unique restriction site composition stem from differences in the plasmid backbone sequences.

Figure 19:
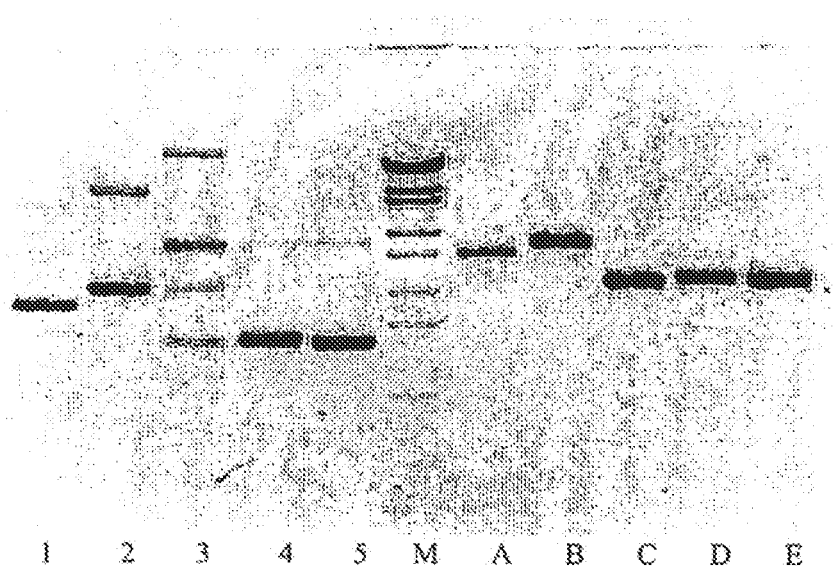

FIG. 19 shows the results of a restriction mapping of preferred vectors according to the invention. Both undigested Acceptor (pACE, pACE2) and Donor vectors (pDC, pDK, pDS) are shown as well as the same vectors digested with BamHI. All restriction reactions yield the expected sizes. Lanes 1-5 show uncut pACE, pACE2, pDC, pDK, and pDS vectors; lane M shows λ StyI marker; lanes A-E show BamHI digested pACE, pACE2, pDC, pDK, and pDS vectors.

Figure 20:
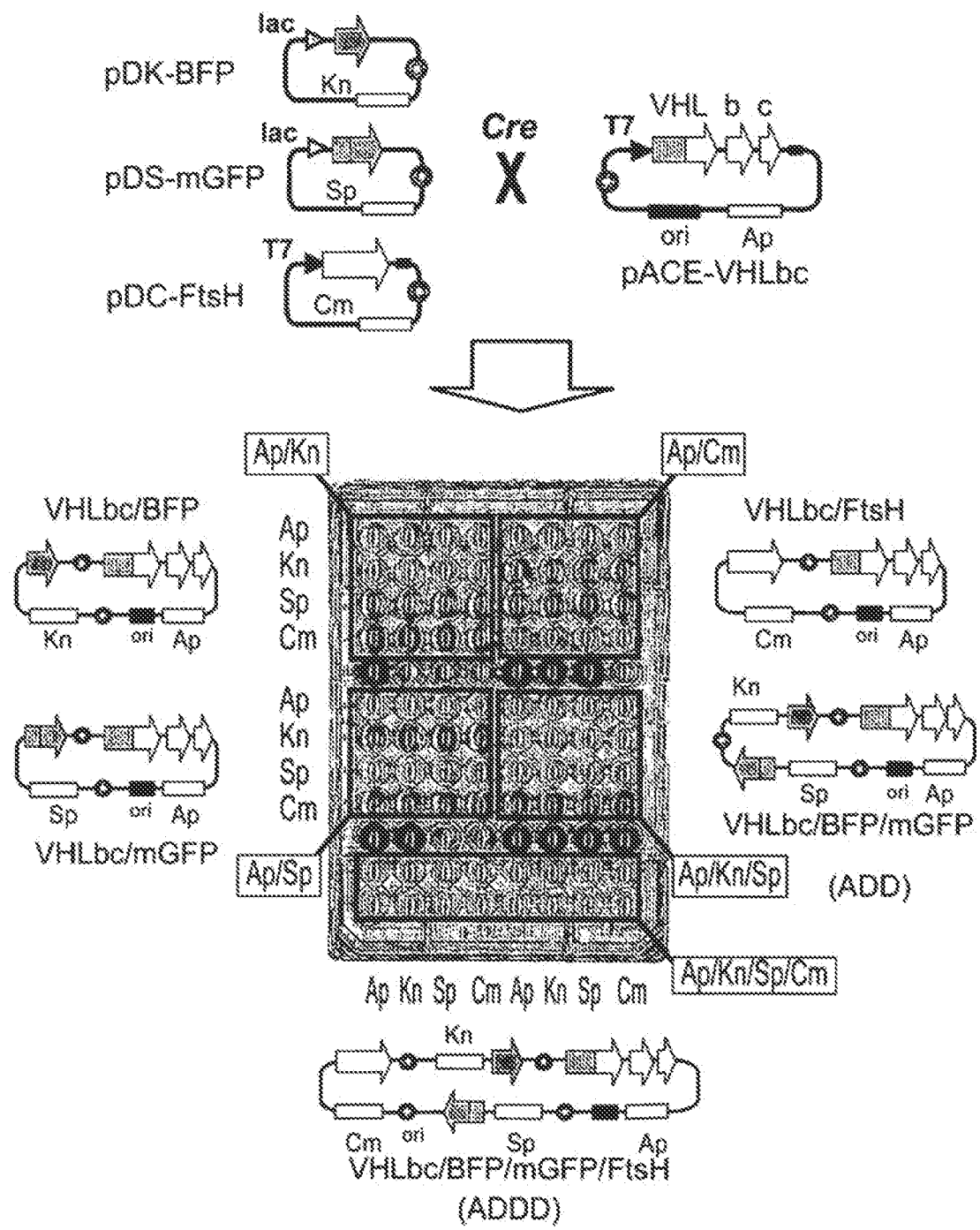

FIG. 20 shows the strategy for Acceptor/Donor recombineering according to the invention exemplified for genes coding for Von Hippel-Lindau/elonginB/elonginC (VHLbc) complex (Tan et al. (2005), supra; see also FIG. 9 above), FtsH soluble domain (Bieniossek et al. (2006) *Proc. Natl. Acad. Sci. USA* 103, 3066-3071), blue fluorescent protein (BFP), and green fluorescent protein (mGFP) with a coiled-coil domain (Berger et al. (2003) *Proc. Natl. Acad. Sci. USA* 100, 12177-12182) were inserted into pACE, pDC, pDK and pDS, respectively. Cre-fusion was followed by transformation into pir⁻ cells (TOP10). Aliquots were plated on agar with two (Ap/Kn; Ap/Cm; Ap/Sp), three (Ap/Kn/Sp) and four (Ap/Kn/Sp/Cm) antibiotics. Four colonies from each plate were challenged in a 96 well microtiter plate. Labels left of the plate image denote antibiotics contained in media aliquots in horizontal rows. Wells in the bottom two rows were charged differently (labels below the plate image). Those inoculated with four colonies each from one agar plate are boxed in black, and flagged with antibiotics contained in the agar plate. Four vertical rows in each such 16-well box were inoculated with the same colony. In the bottom two rows, four wells in a row were inoculated with the same colony. Expected vector architecture of the double, triple (ADD) and quadruple (ADDD) fusions is shown left or right (16 well boxes), respectively, or below (bottom two rows) of the plate image. Red dye is used as positional marker. Deconstruction of the ADDD fusion was carried out successfully in the reverse approach.

Figure 21:
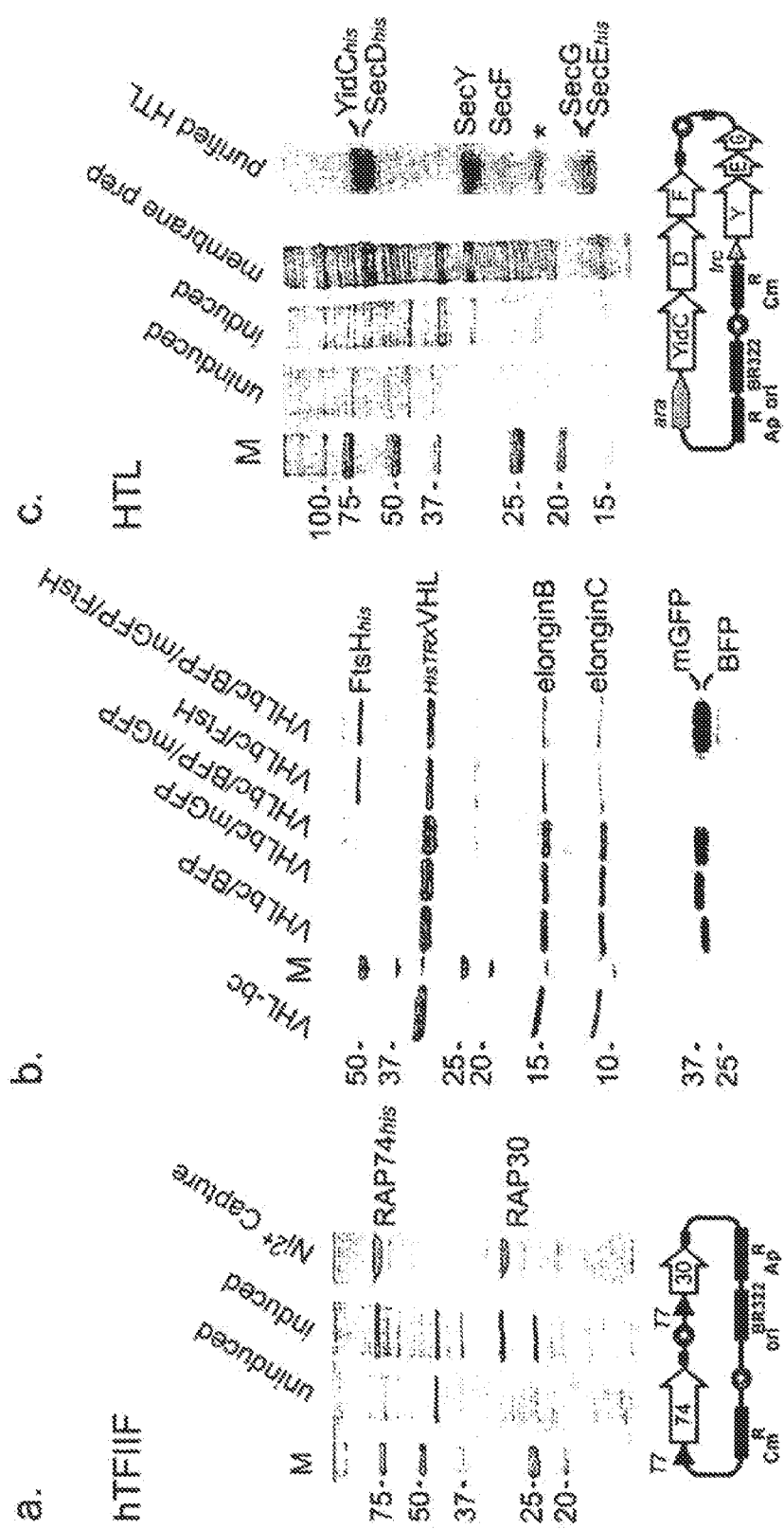

FIG. 21 shows the results of multiprotein complex expression of human TFIIF (FIG. 21A), the Von Hippel-Lindau/elonginB/elonginC (VHLbc) complex (FIG. 21B) and the prokaryotic transmembrane holotranlocon (HTL) YidC-SecYEGDF (FIG. 21C). (A) Human TFIIF was assembled and purified using a TECAN Freedom EvoII 200 workstation, and analyzed by SDS-PAGE. Uninduced and induced whole cell extracts and purified hTFIIF are shown, with subunits (RAP74, RAP30) marked. RAP74 contained a C-terminal oligohistidine tag. (B) All multigene constructs from FIG. 20 were assembled, expressed and cell lysates analyzed in parallel following the same routine as for hTFIIF (labels as in FIG. 20). The VHLbc complex was captured by an oligohistidine-thioredoxin-fusion tag on the VHL subunit (Tan et al. (2005), supra). FtsH contained an oligohistidine tag at its C-terminus (Bieniossek et al. (2006, supra). Fluorescent proteins were identified in lysates by Western blot with antibody Roche 1814460 (1:1000 in TBST/3(YoBSA). (C) Production of the entire prokaryotic transmembrane holotranslocon (HTL) YidC-SecYEGDF. Membrane vesicle preparation, detergent solubilization, $Ni^{2+}$ affinity capture and size exclusion chromatography resulted in purified holotranslocon complex (right). Subunits are labeled. A breakdown product of SecY is marked with an asterisk. In all panels, M stands for Biorad broad range marker (sizes in kDa).

Figure 22:
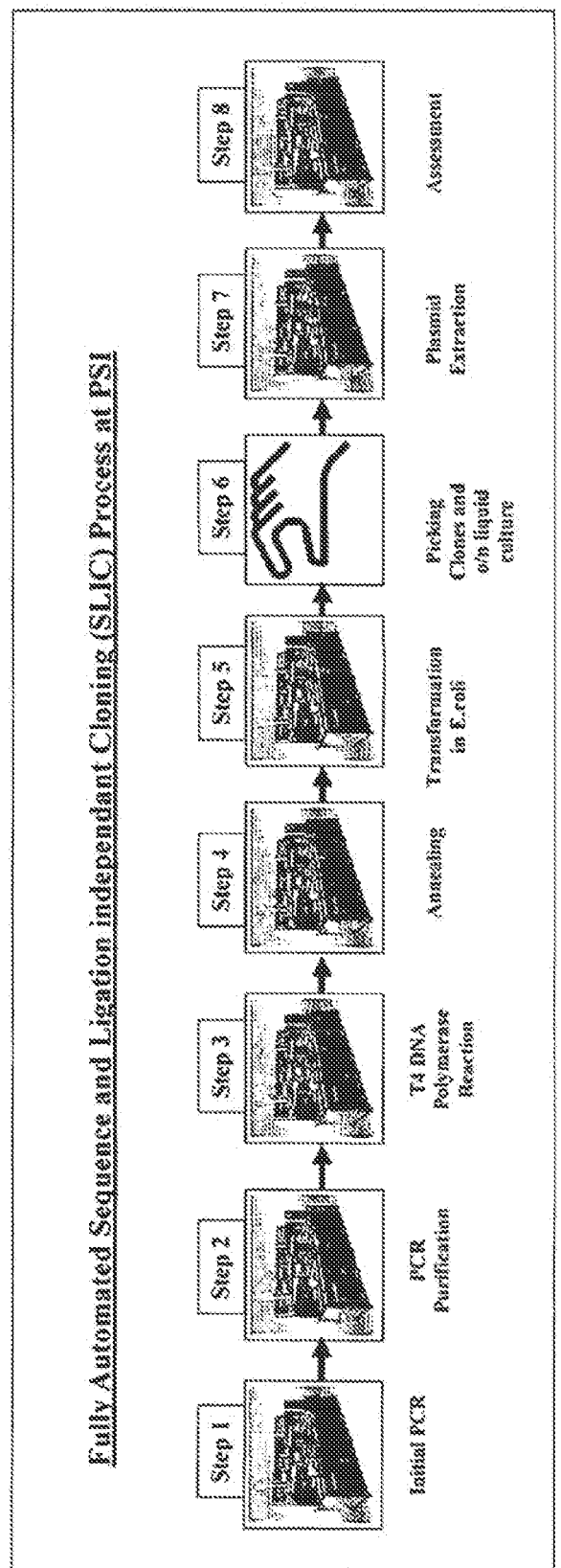

FIG. 22 shows a schematic workflow for an automated SLIC process.

Figure 23:
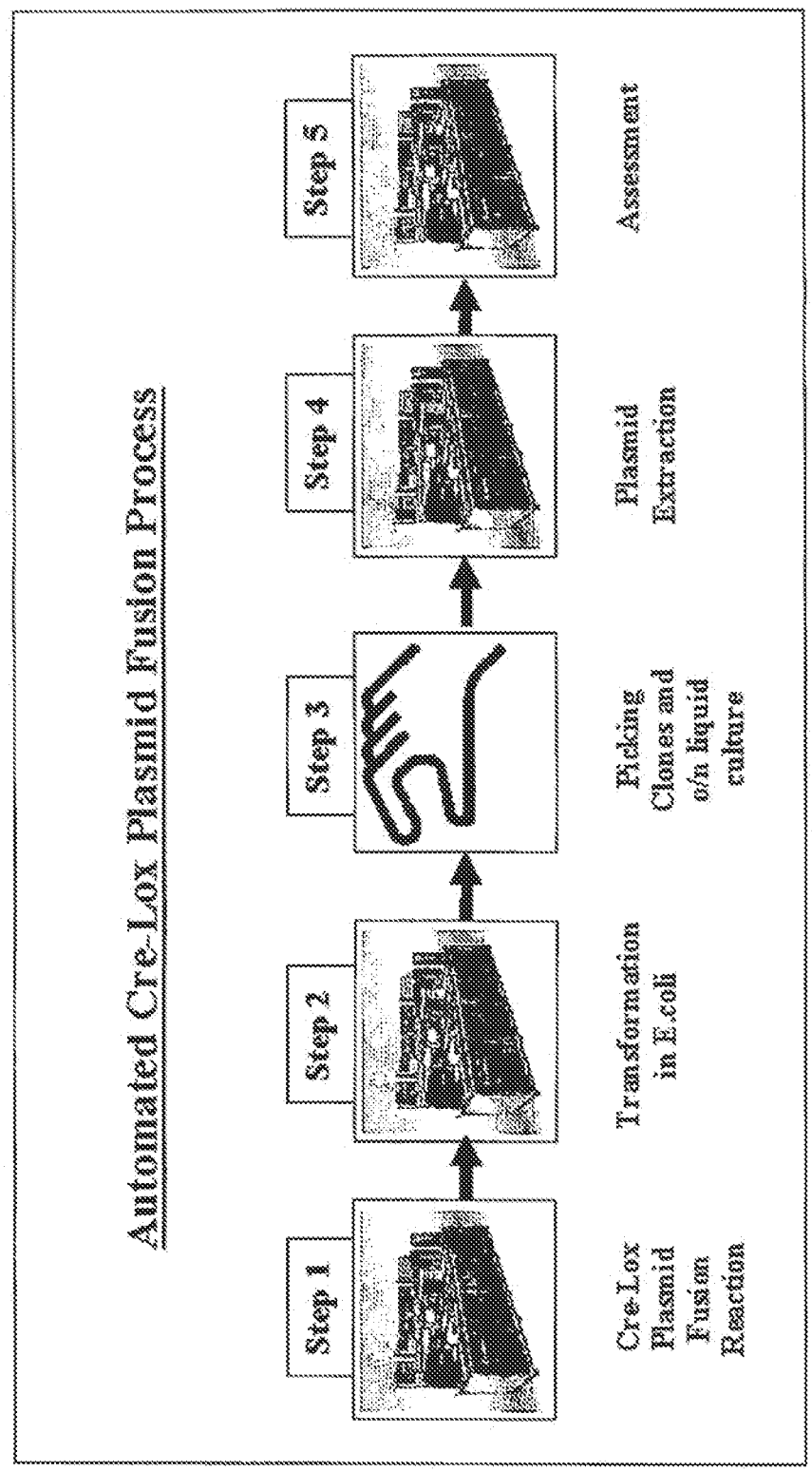

FIG. 23 shows a schematic workflow for an automated Cre fusion process.

Figure 24:
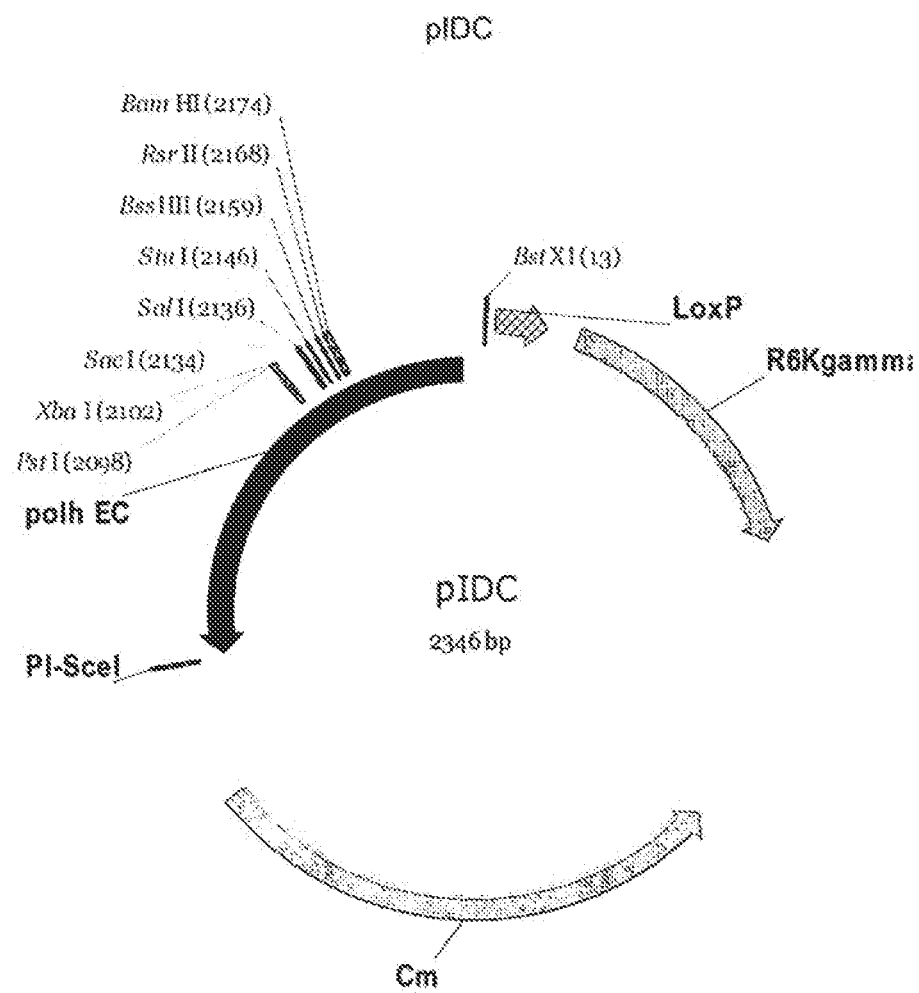

FIG. 24 shows a plasmid map of a preferred vector (Donor vector) of the invention called pIDC (SEQ ID NO: 7).

Figure 25:
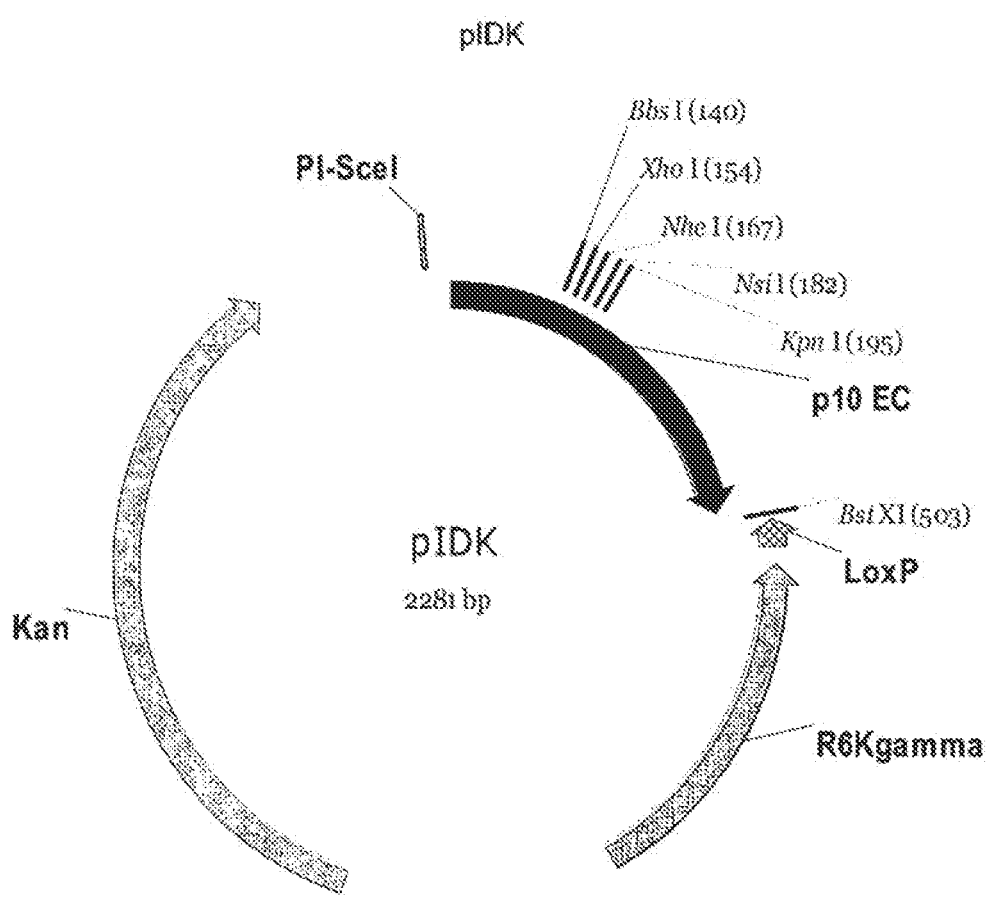

FIG. 25 shows the plasmid map of a preferred vector (Donor vector) of the invention called pIDK (SEQ ID NO: 8).

Figure 26:
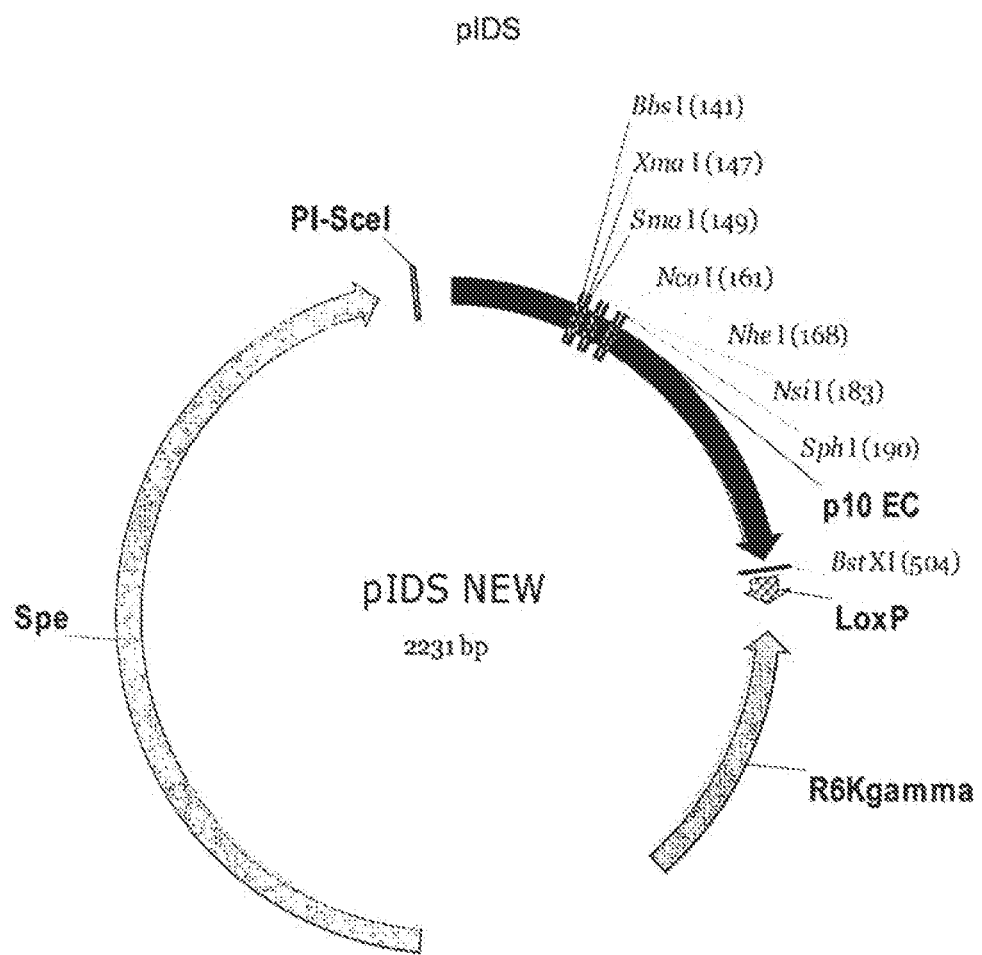

FIG. 26 shows the plasmid map of a preferred vector (Donor vector) of the invention called pIDS (SEQ ID NO: 9).

Figure 27:
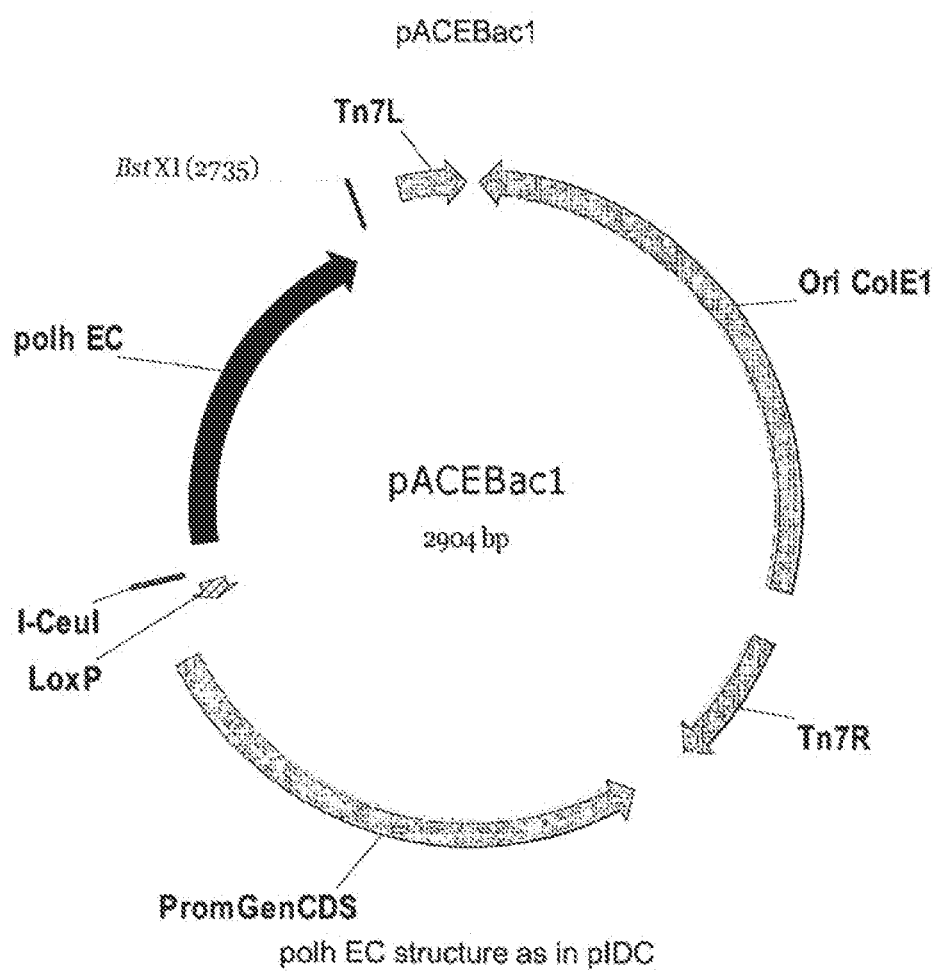

FIG. 27 shows the plasmid map of a preferred vector (Acceptor vector) of the invention called pACEBac1 (SEQ ID NO: 10).

Figure 28:
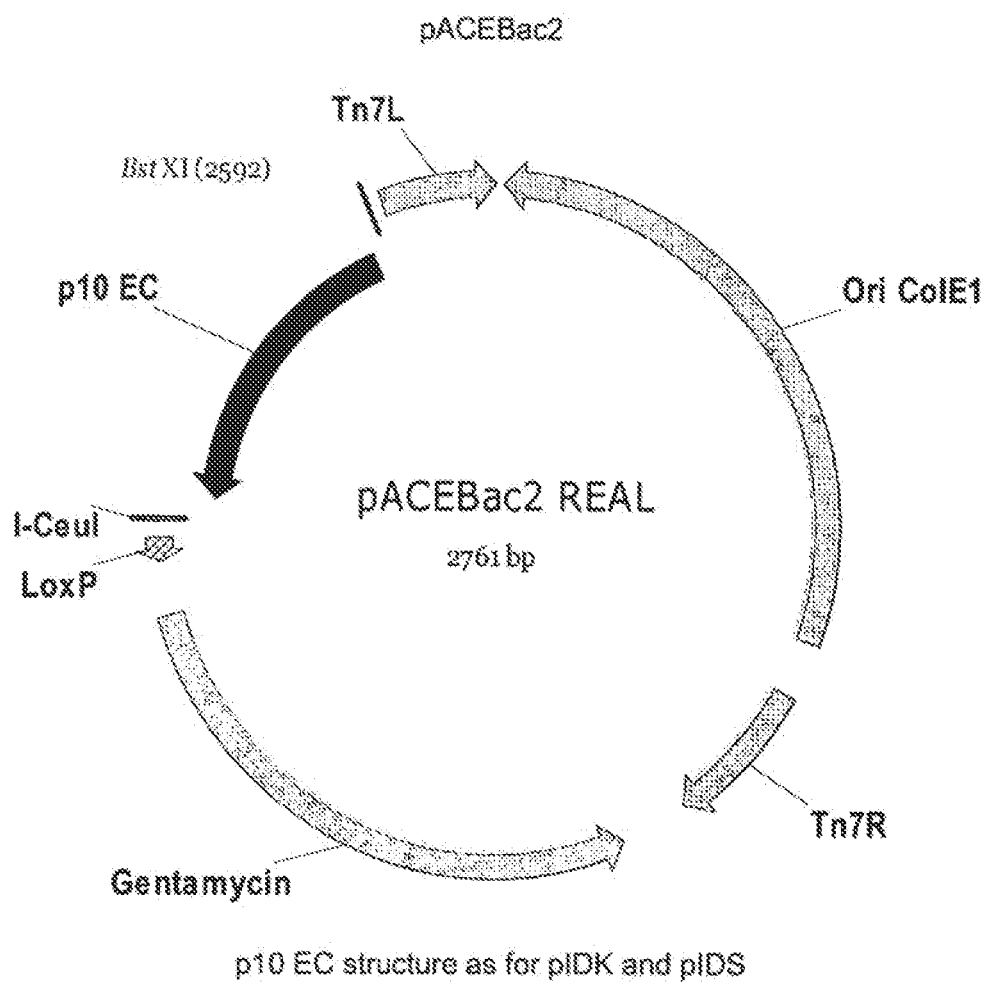

FIG. 28 shows the plasmid map of a preferred vector (Acceptor vector) of the invention called pACEBac2 (SEQ ID NO: 11).

Figure 29:
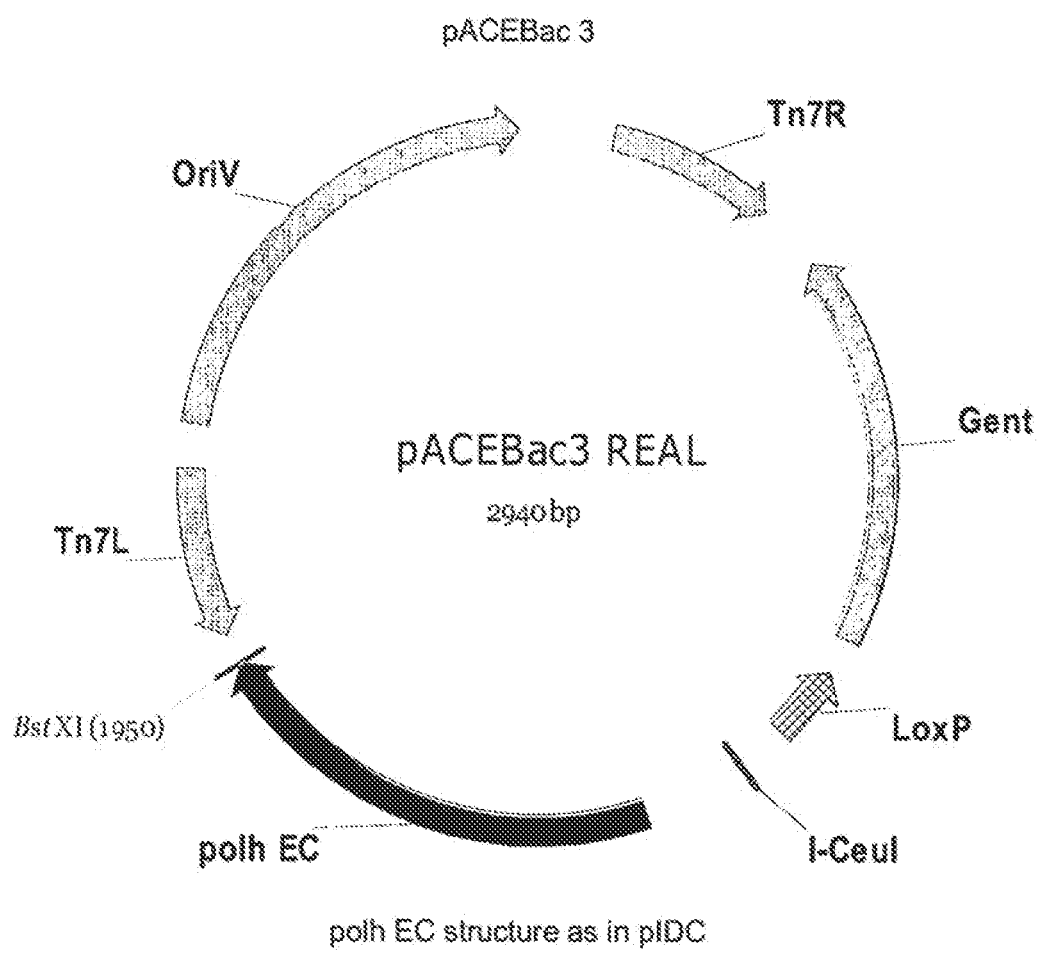

FIG. 29 shows the plasmid map of a preferred vector (Acceptor vector) of the invention called pACEBac3 (SEQ ID NO: 12).

Figure 30:
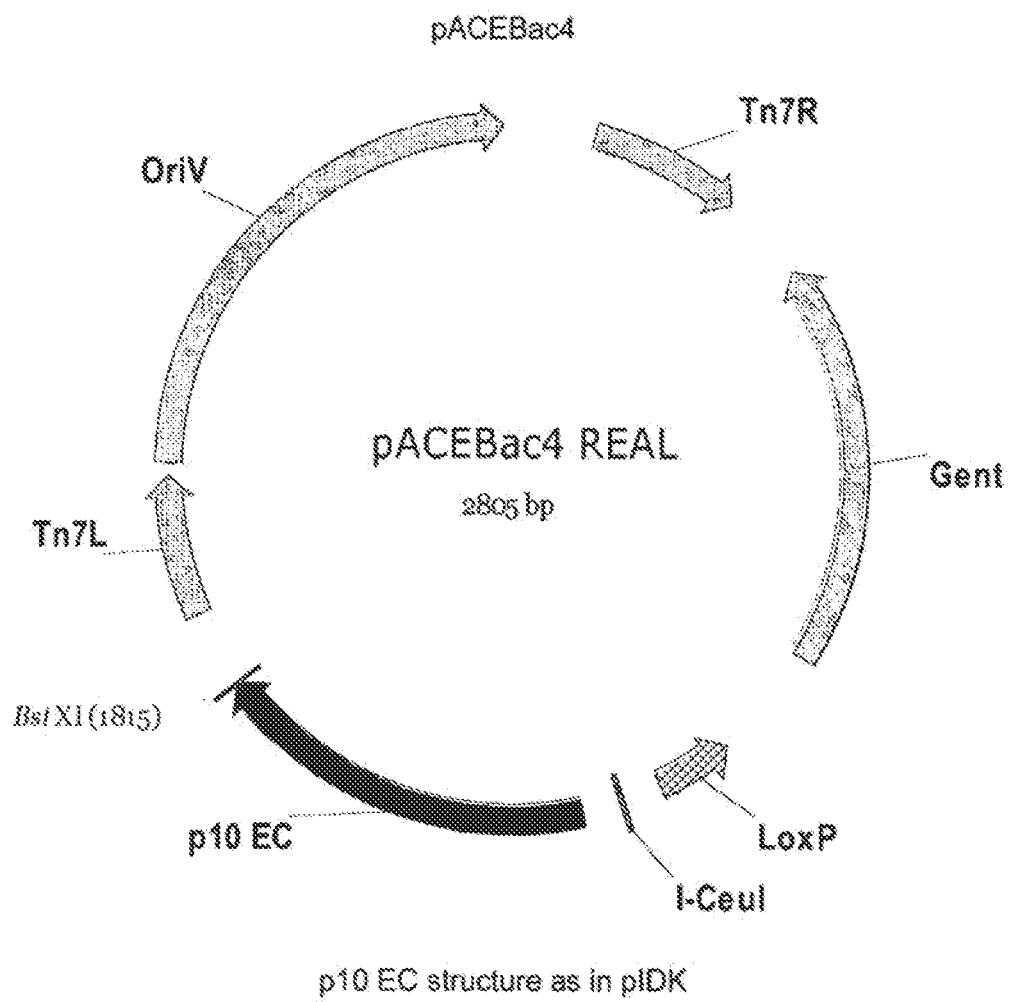

FIG. 30 shows the plasmid map of a preferred vector (Acceptor vector) of the invention called pACEBac4 (SEQ ID NO: 13).

Figure 31:
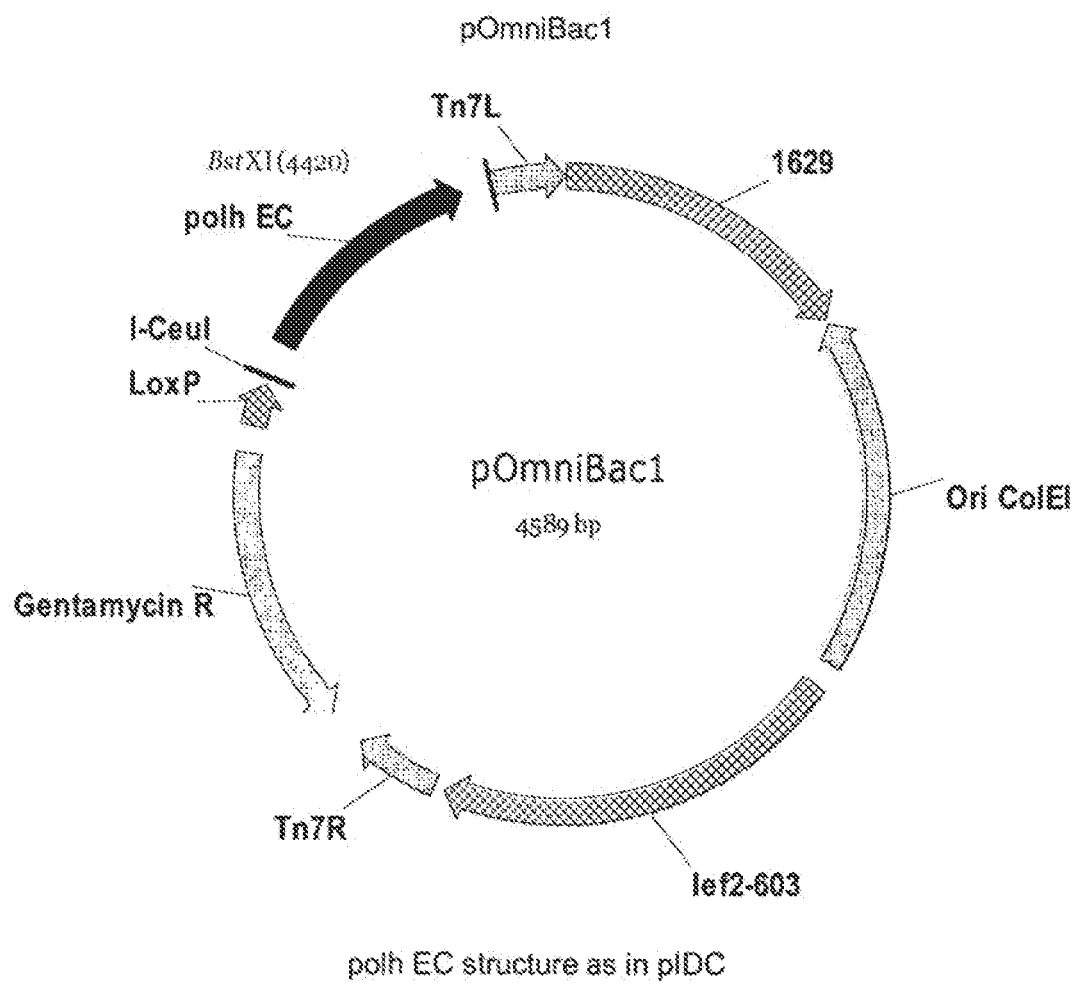

FIG. 31 shows the plasmid map of a preferred vector (Acceptor vector) of the invention called pOmniBac1 (SEQ ID NO: 14).

Figure 32:
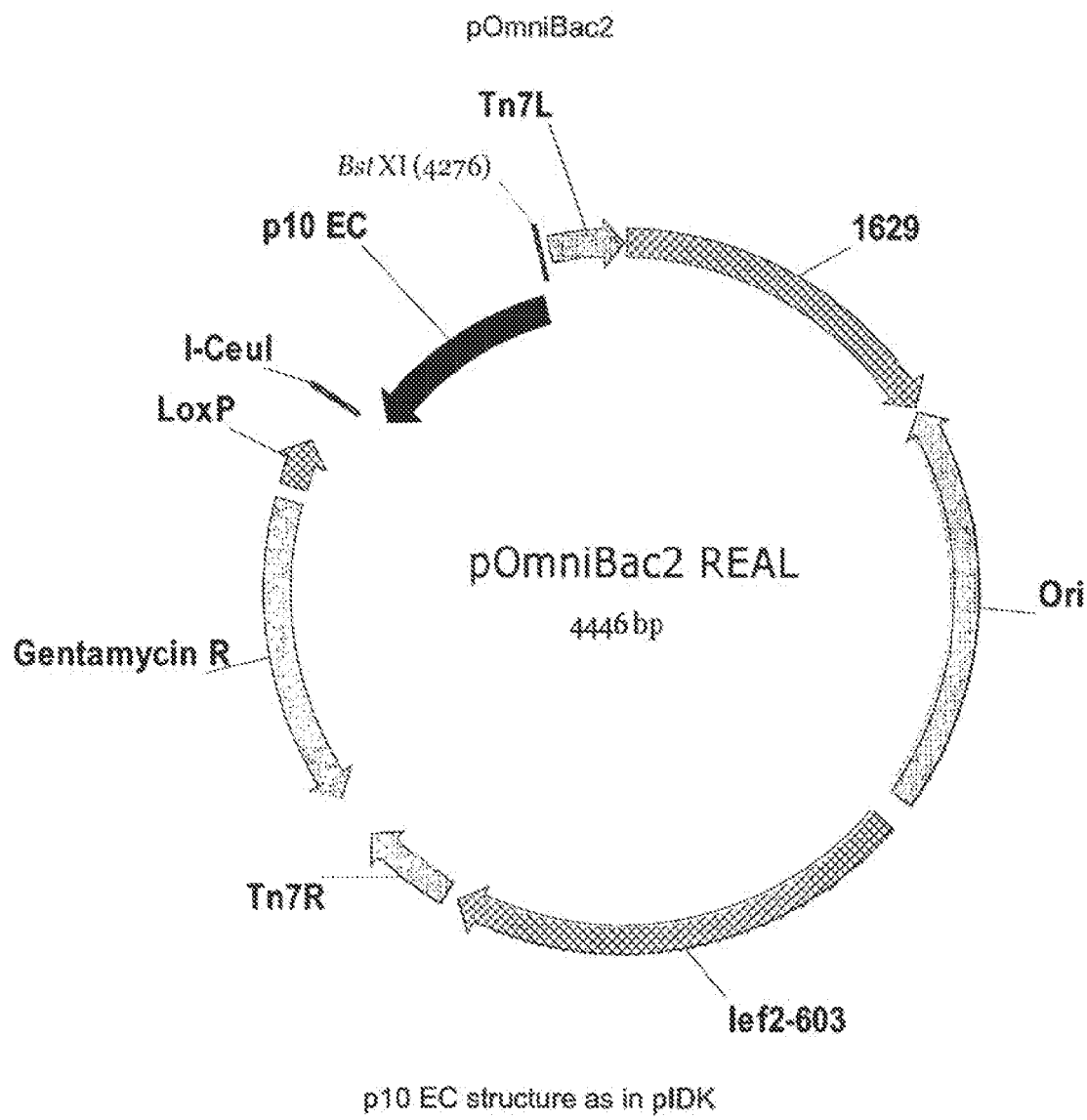

FIG. 32 shows the plasmid map of a preferred vector (Acceptor vector) of the invention called pOmniBac2 (SEQ ID NO: 15).

Figure 33:
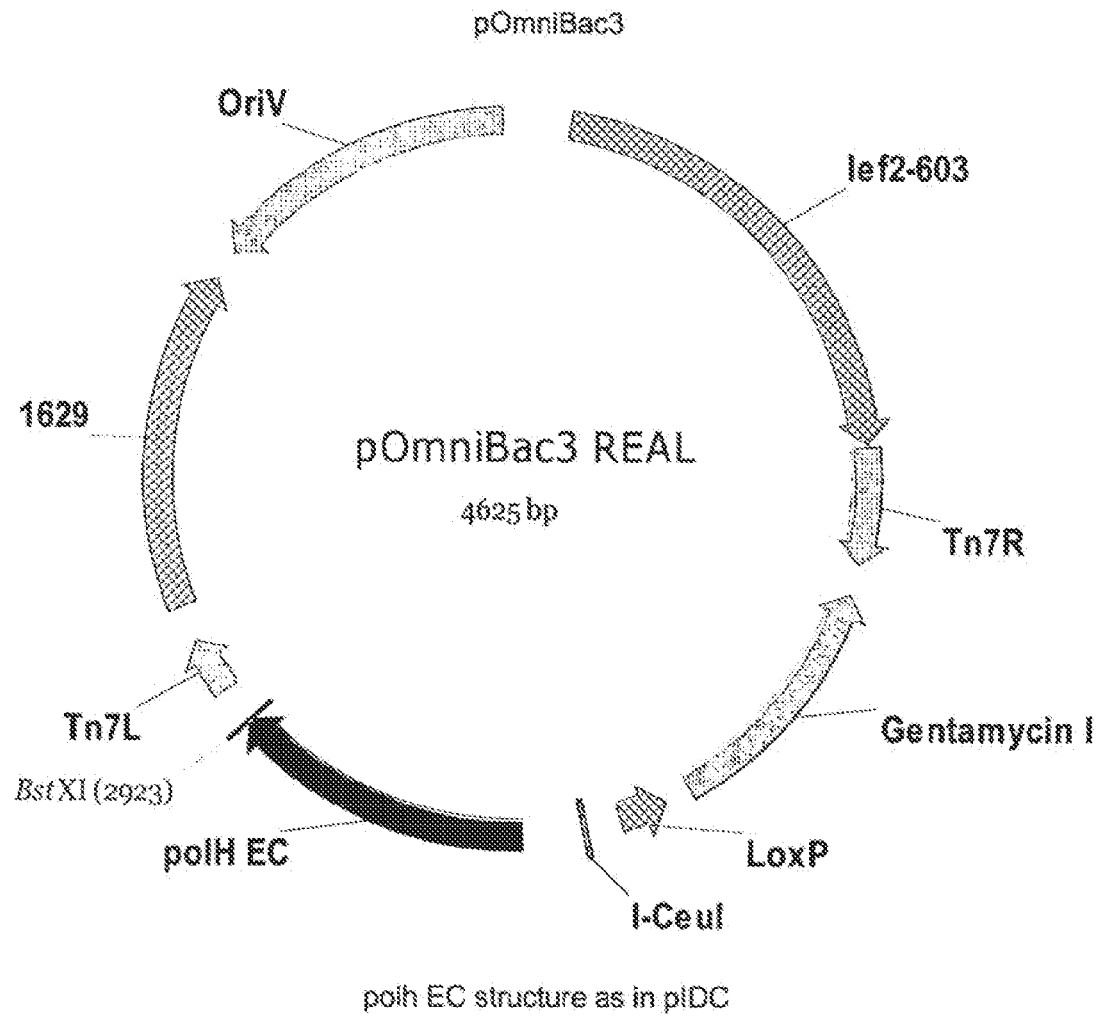

FIG. 33 shows the plasmid map of a preferred vector (Acceptor vector) of the invention called pOmniBac3 (SEQ ID NO: 16).

Figure 34:
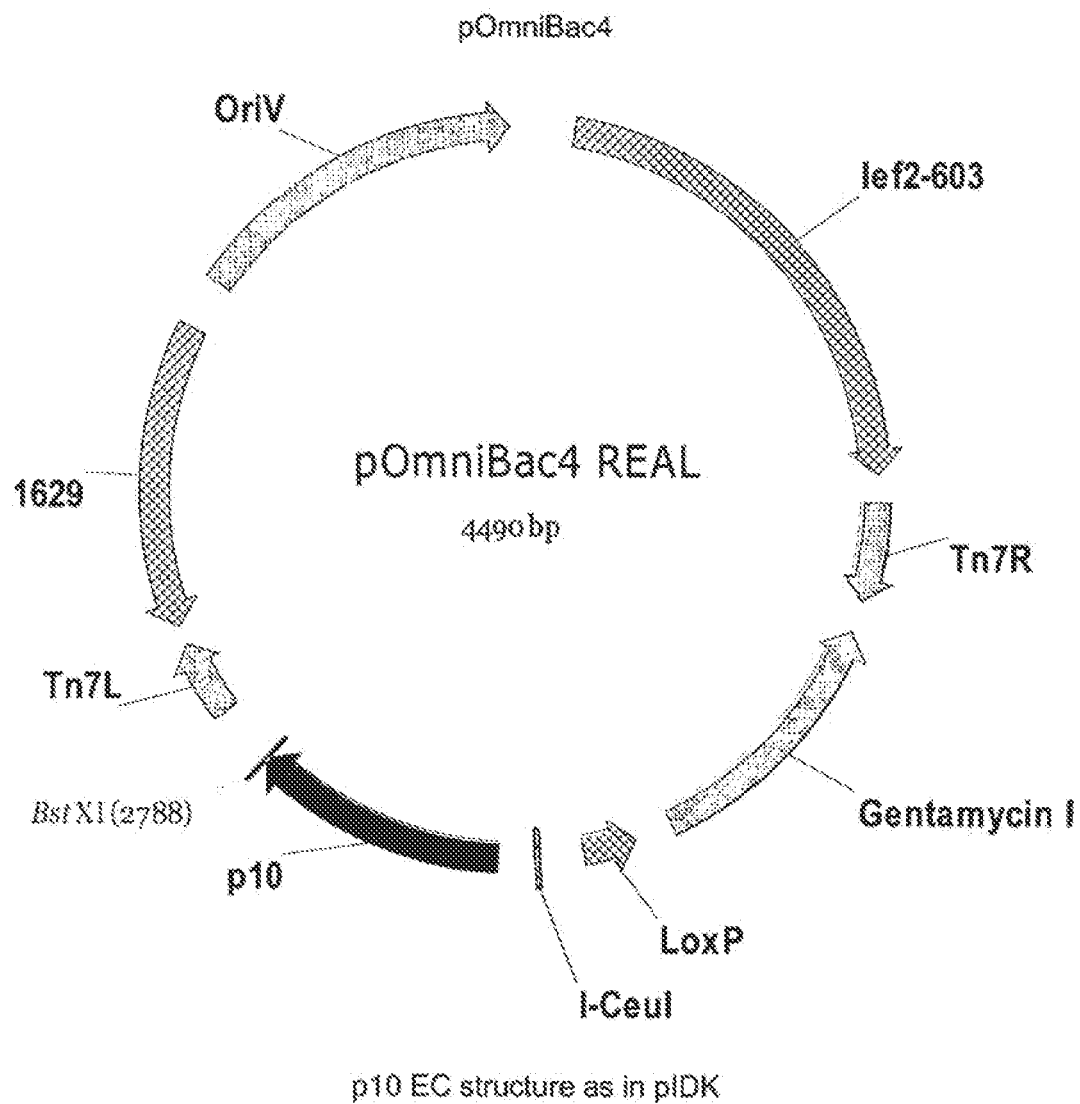

FIG. 34 shows the plasmid map of a preferred vector (Acceptor vector) of the invention called pOmniBac4 (SEQ ID NO: 17).

Figure 35:
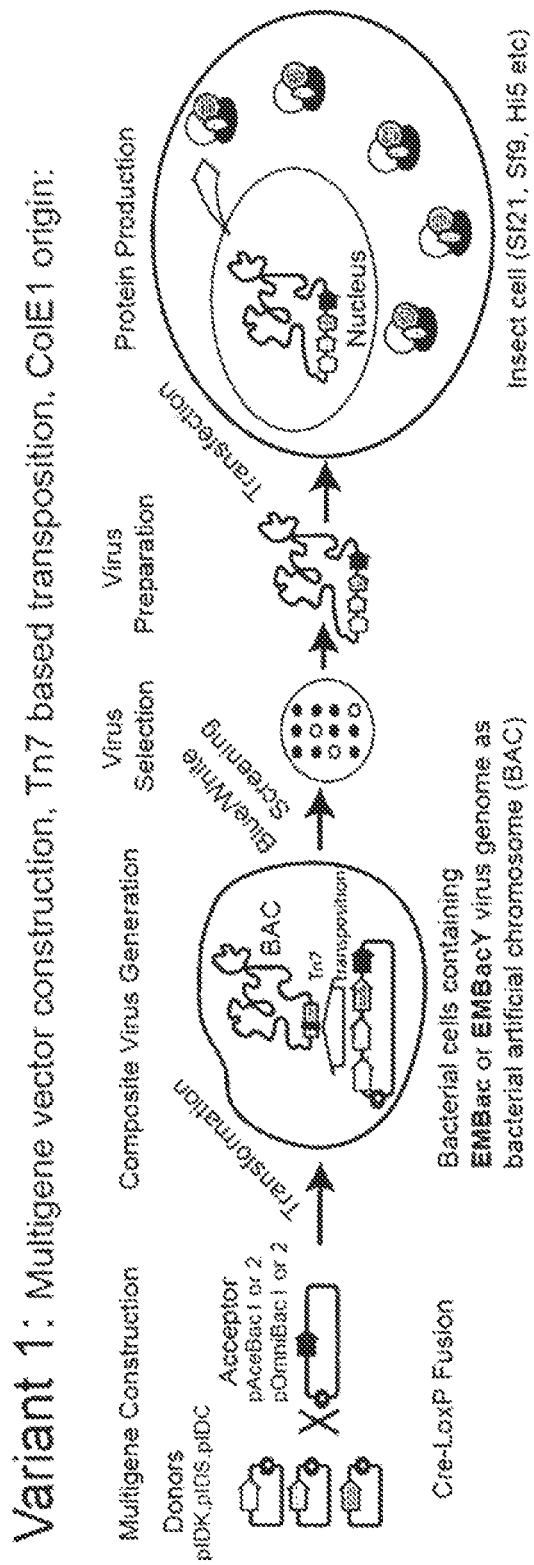

FIG. 35 shows a scheme for multiprotein expression in insect cells by generating composite baculovirus using Acceptor vectors of the present invention carrying a ColE1 origin (pACEBac1, pACEBac2, pOmniBac1, pOmniBac2). Multigene fusions are generated by Cre-LoxP fusion of the desired Donor/Acceptor combinations (multigene construction). The fusion vector is transformed in bacteria carrying a baculovirus genome (such as bacoluvirus EMBac or EMBAcY) as a bacterial artificial chromosome (BAC). The vector fusion is integrated into the baculovirus genome by Tn7 based transposition. Productive composite viruses are selected by blue/white screening (integration of the vector fusion into the T7 attachment site of the virus destroys a lacZ gene present on the virus). Composite viruses are prepared and suitable insect cells are transfected for protein production.

Figure 36:
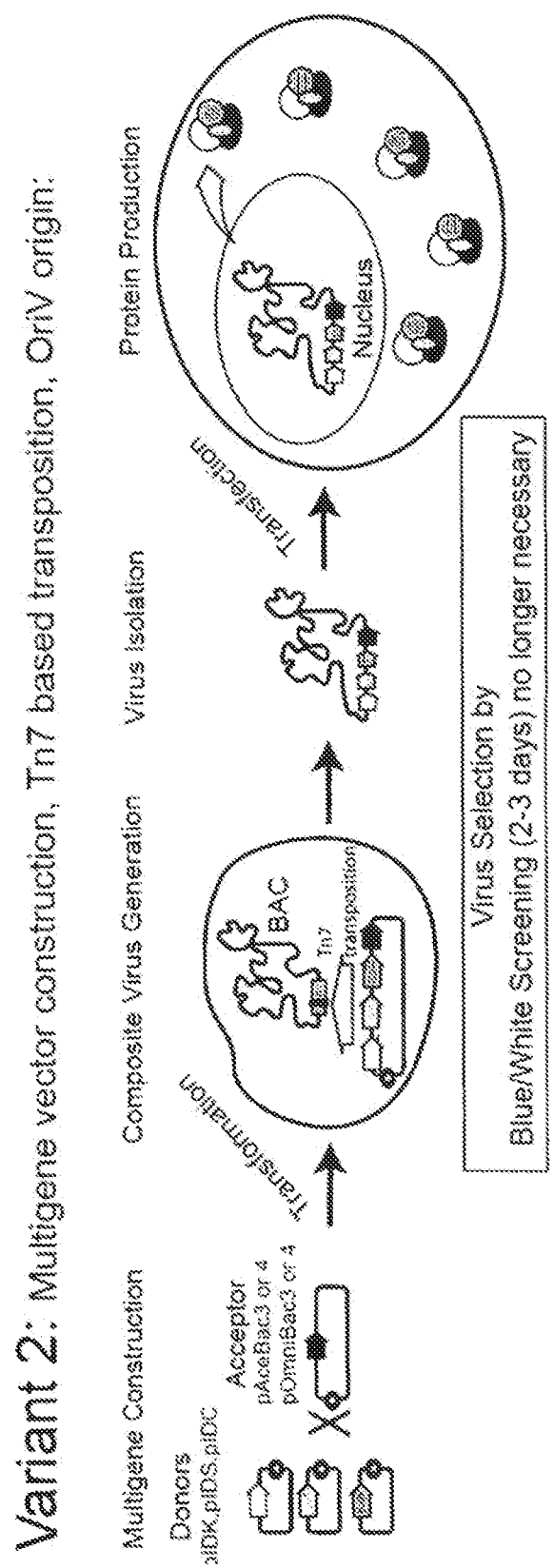

FIG. 36 shows a scheme for multiprotein expression in insect cells by generating composite baculovirus using Acceptor vectors of the present invention carrying an OriV origin (pACEBac3, pACEBac4, pOmniBac3, pOmniBac4). Multigene fusions are generated by Cre-LoxP fusion of the desired Donor/Acceptor combinations. The fusion vector is transformed in bacteria carrying a baculoviurs genome (such bacoluvirus EMBac or EMBAcY) as a bacterial artificial chromosome (BAC). The vector fusion is integrated into the baculovirus genome by Tn7 based transposition. Since the Acceptor vectors carrying an OriV can only be propagated, if a trfA gene is provided in trans, unproductive integration events in bacteria not containing the trfA gene leads to elimination of such transformants upon exposure to the appropriate antibiotic (here: gentamycin). Thus, blue/white screening is not necessary in this case. Composite viruses are then prepared and suitable insect cells are transfected for protein production.

Figure 37:
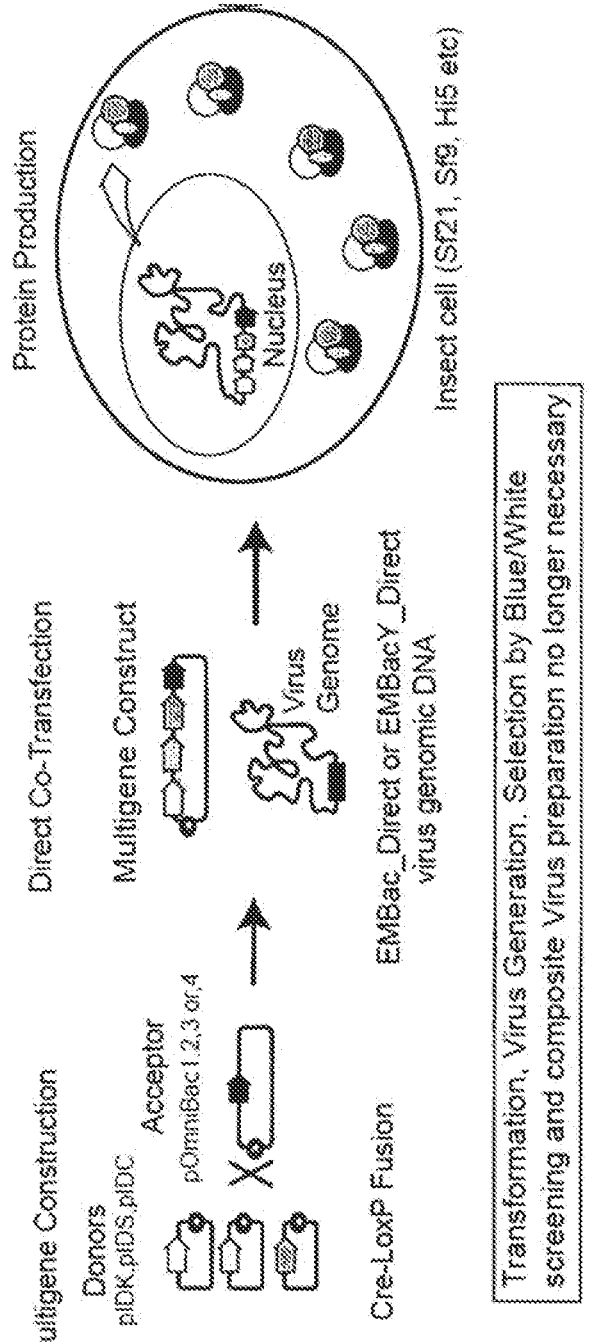

FIG. 37 shows a scheme for multiprotein expression in insect cells by generating composite baculovirus using Acceptor vectors of the present invention carrying lef2-603 and Orf1629 homology sequences (pOmniBac1, pOmniBac2, pOmniBac3, pOmniBac4). Multigene fusions are generated by Cre-LoxP fusion of the desired Donor/Acceptor combinations (multigene construction). The multigene construct and genomic baculovirus DNA carrying a diphtheria toxin A gene flanked by the lef2-603/Orf1629 homology sequences can be directly co-transfected into suitable insect cells for protein production. Transformation of transfer vector into bacteria containing the baculovirus genome, blue/white screening for composite viruses and preparation of composite viruses from the bacteria is no longer necessary.

Figure 38:
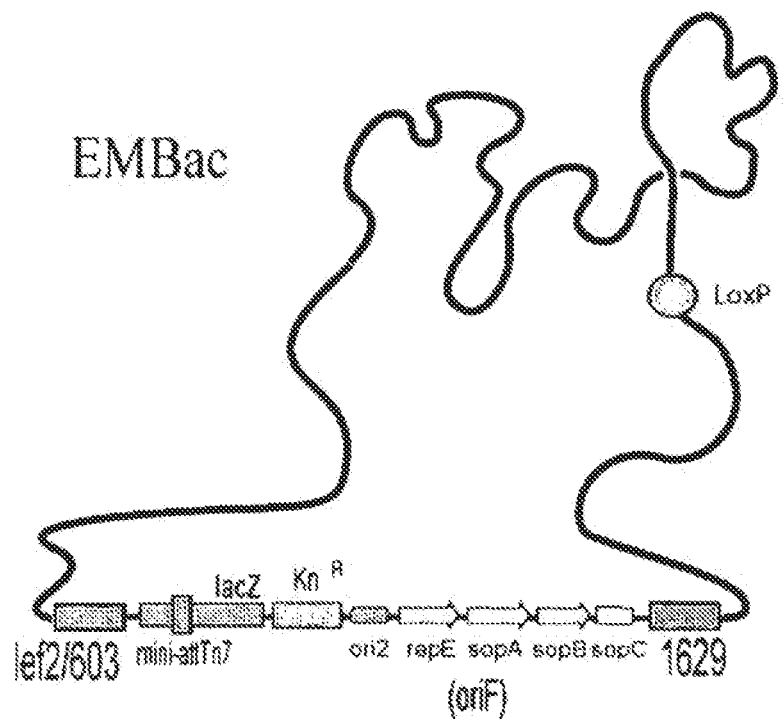

FIG. 38 shows a schematic representation of a baculovirus vector according to the invention called EMBac.

Figure 39:
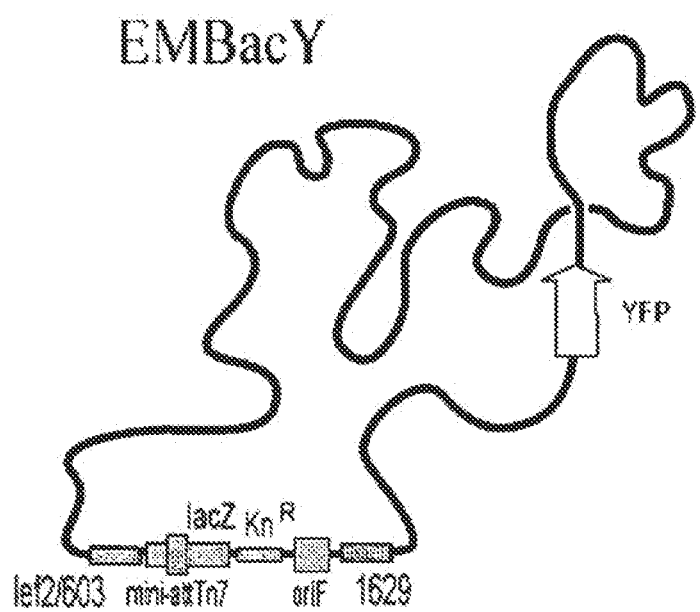

FIG. 39 shows a schematic representation of a baculovirus vector according to the invention called EMBacY.

Figure 40:
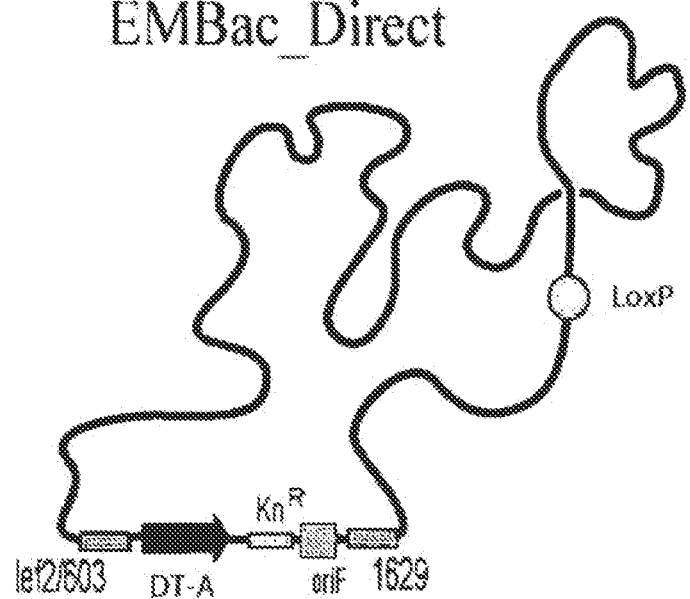

FIG. 40 shows a schematic representation of a baculovirus vector according to the invention called EMBac_Direct.

Figure 41:
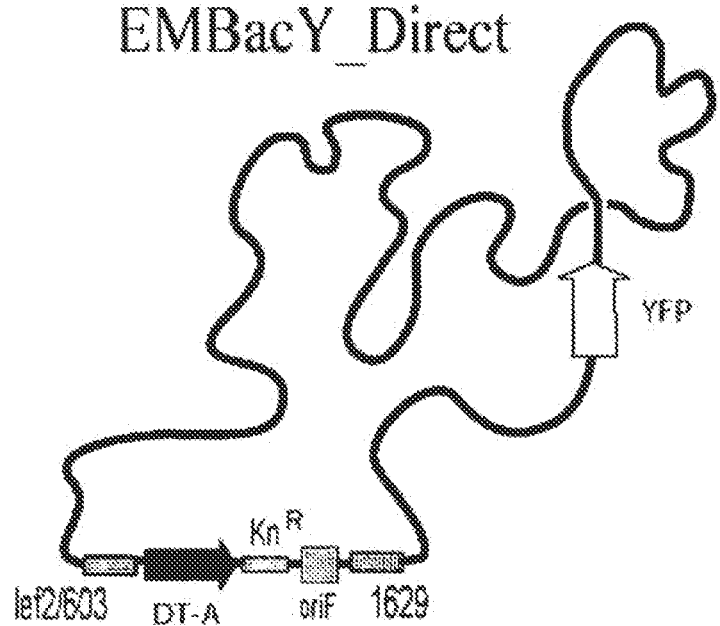

FIG. 41 shows a schematic representation of a baculovirus vector according to the invention called EMBac_DirectY.

Figure 42:
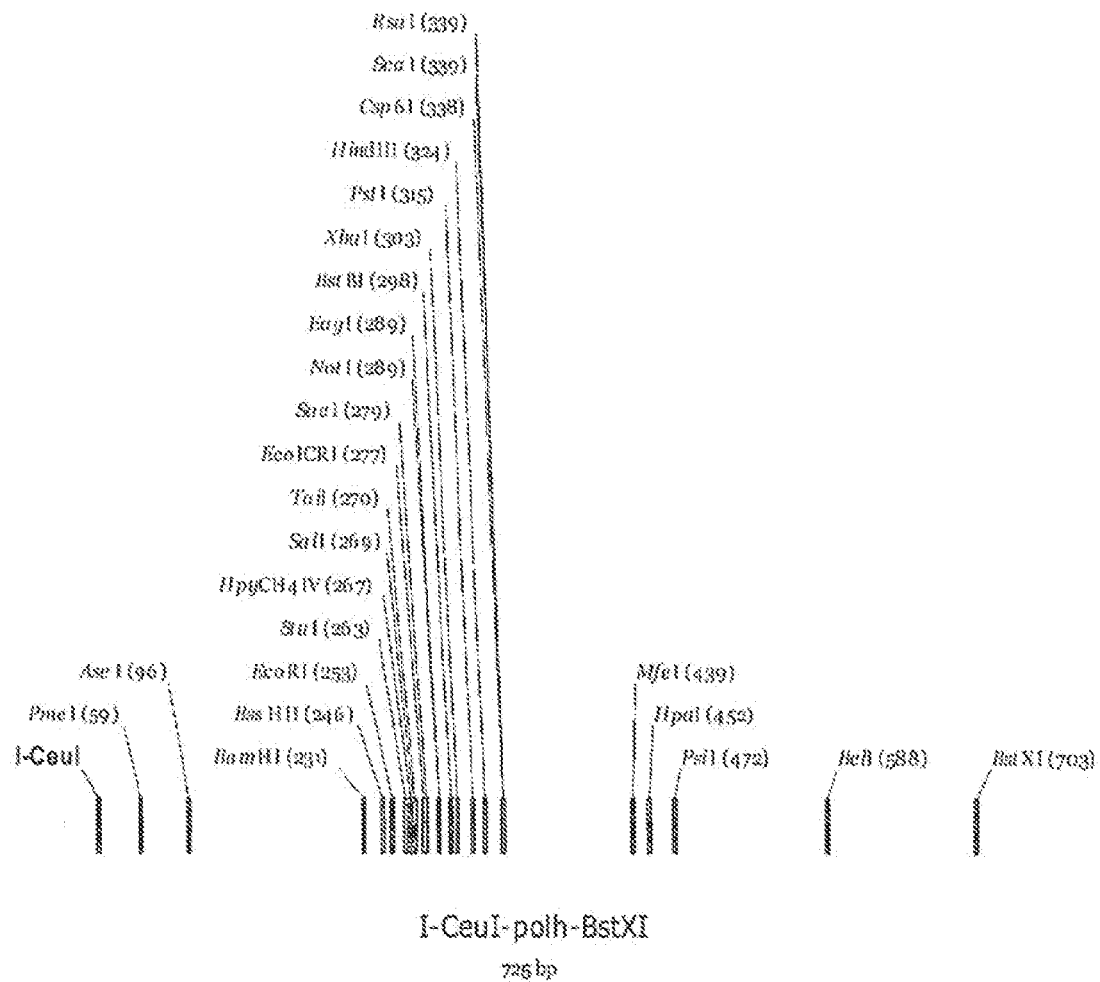

FIG. 42 shows a schematic representation of an MIE according to the invention having the general structure I-CeuI-p10-MCS-BstXI present, for example in Acceptor vectors such as pACEBac 2.

Figure 43:
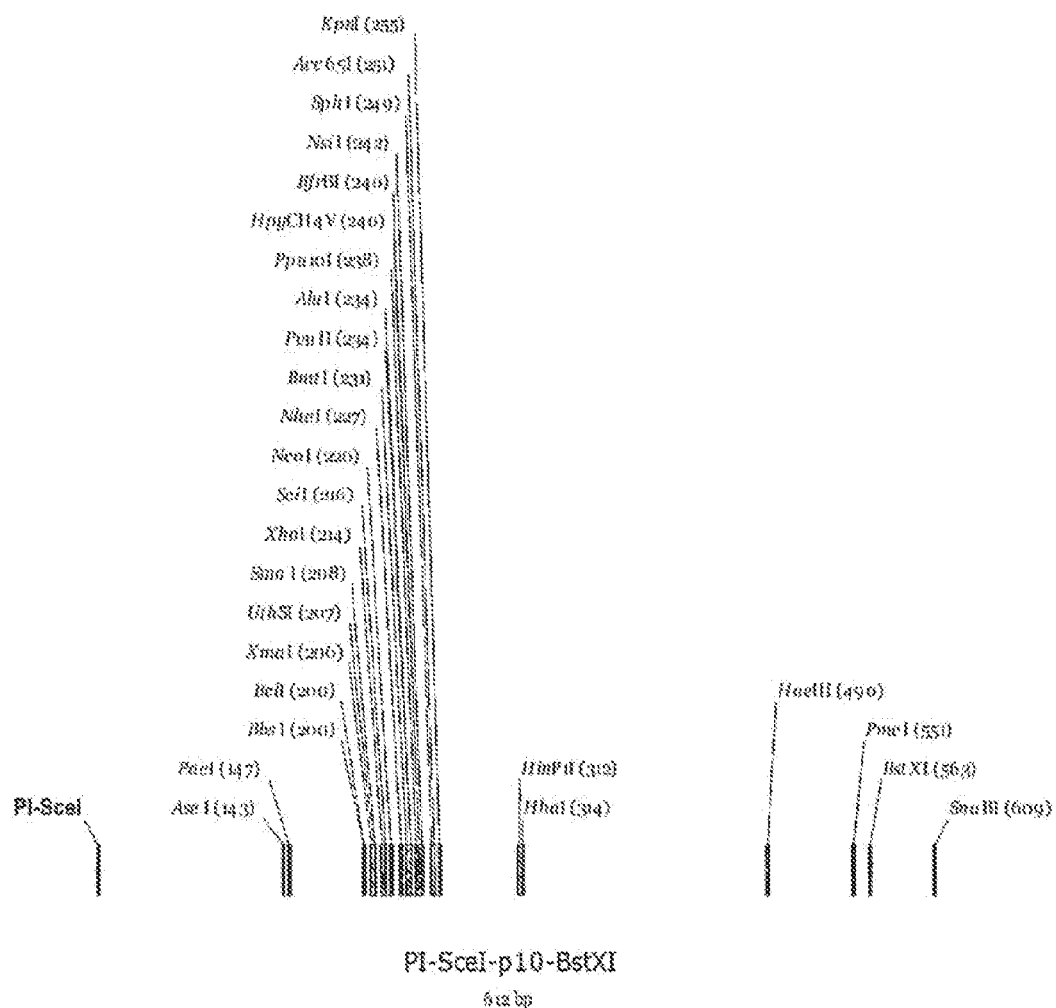

FIG. 43 shows a schematic representation of an MIE according to the invention having the general structure PI-SceI-p10-MCS-BstXI present, for example in Donor vectors such as pIDS.

Figure 44:
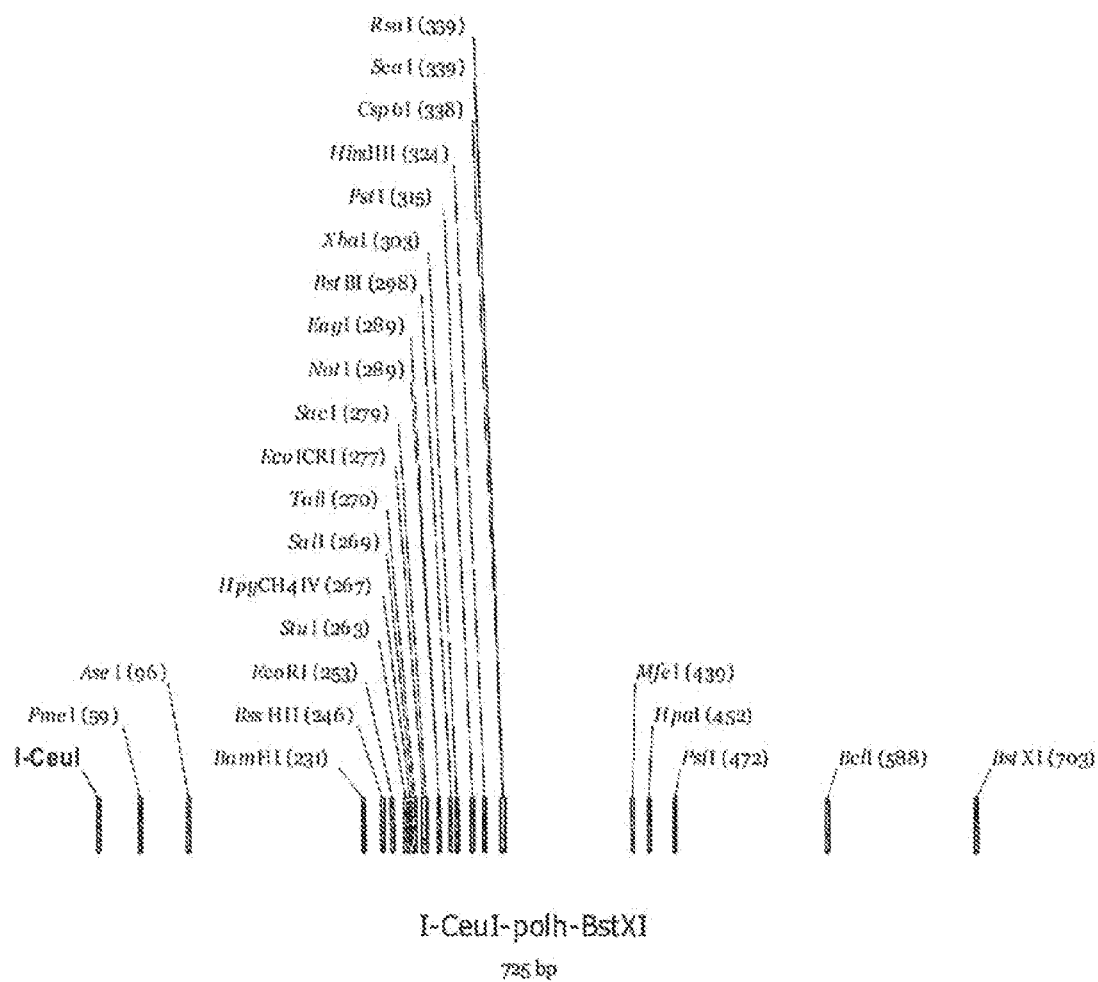

FIG. 44 shows a schematic representation of an MIE according to the invention having the general structure I-CeuI-polh-MCS-BstXI present, for example in Acceptor vectors such as pACEBac 1.

Figure 45:
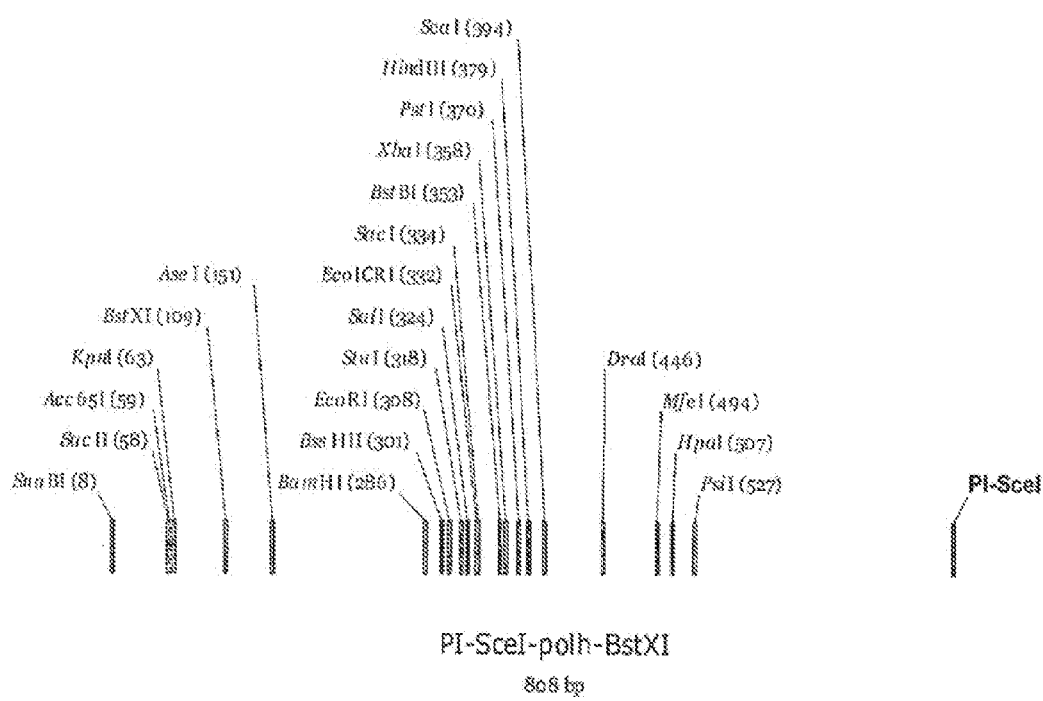

FIG. 45 shows a schematic representation of an MIE according to the invention having the general structure PI-SceI-polh-MCS-BstXI present, for example in Donor vectors such as pIDC.

Figure 46:
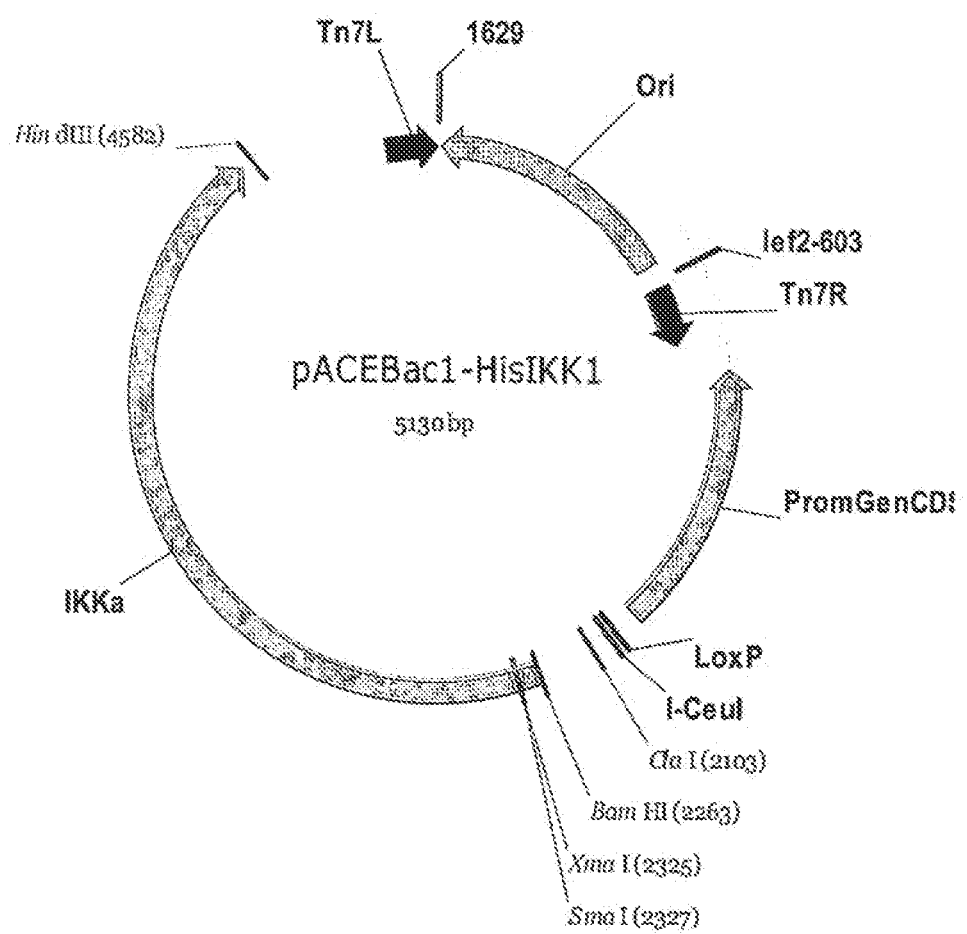

FIG. 46 shows a schematic representation of vector pACE-Bac1-HisIKK1.

Figure 47:
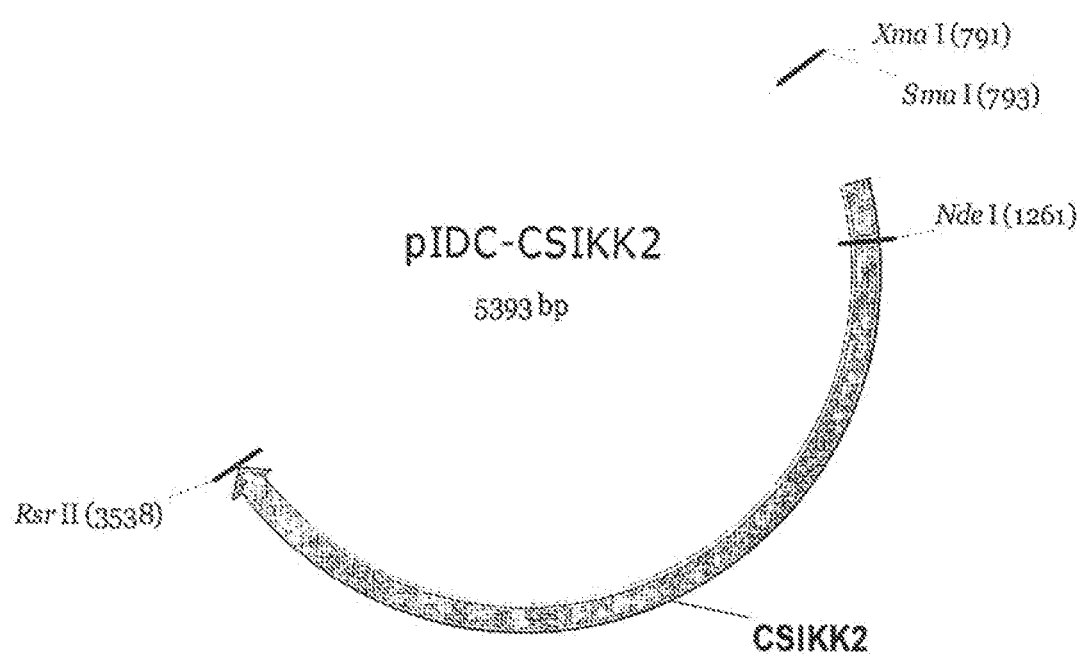

FIG. 47 shows a schematic representation of vector pIDC-CSIKK2.

Figure 48:
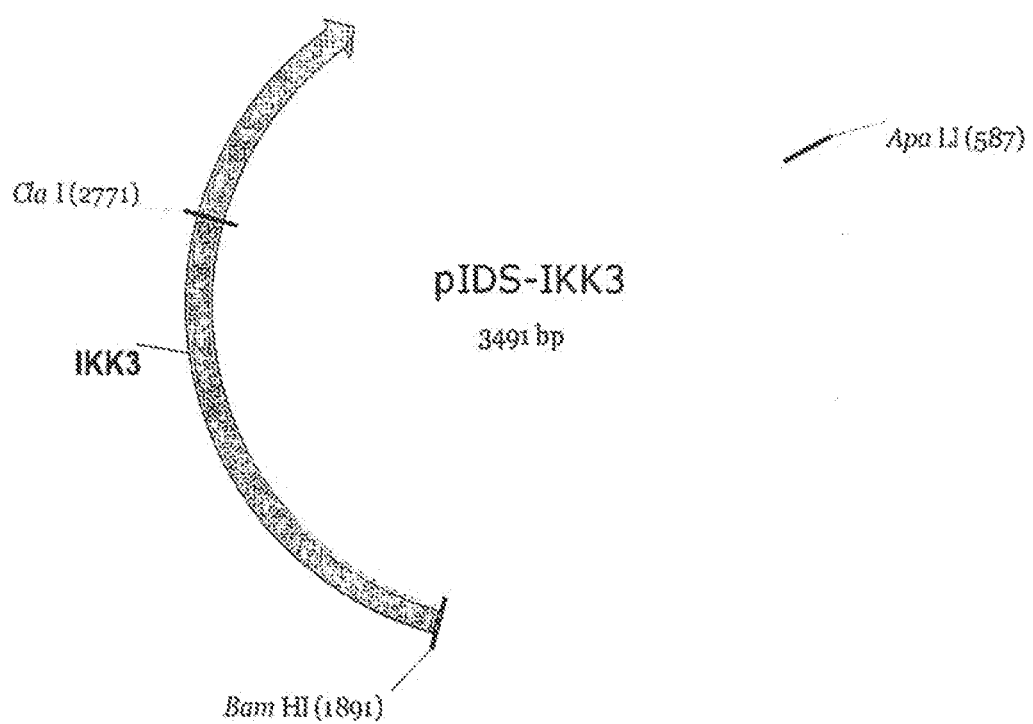

FIG. 48 shows a schematic representation of vector pIDS-IKK3.

Figure 49:
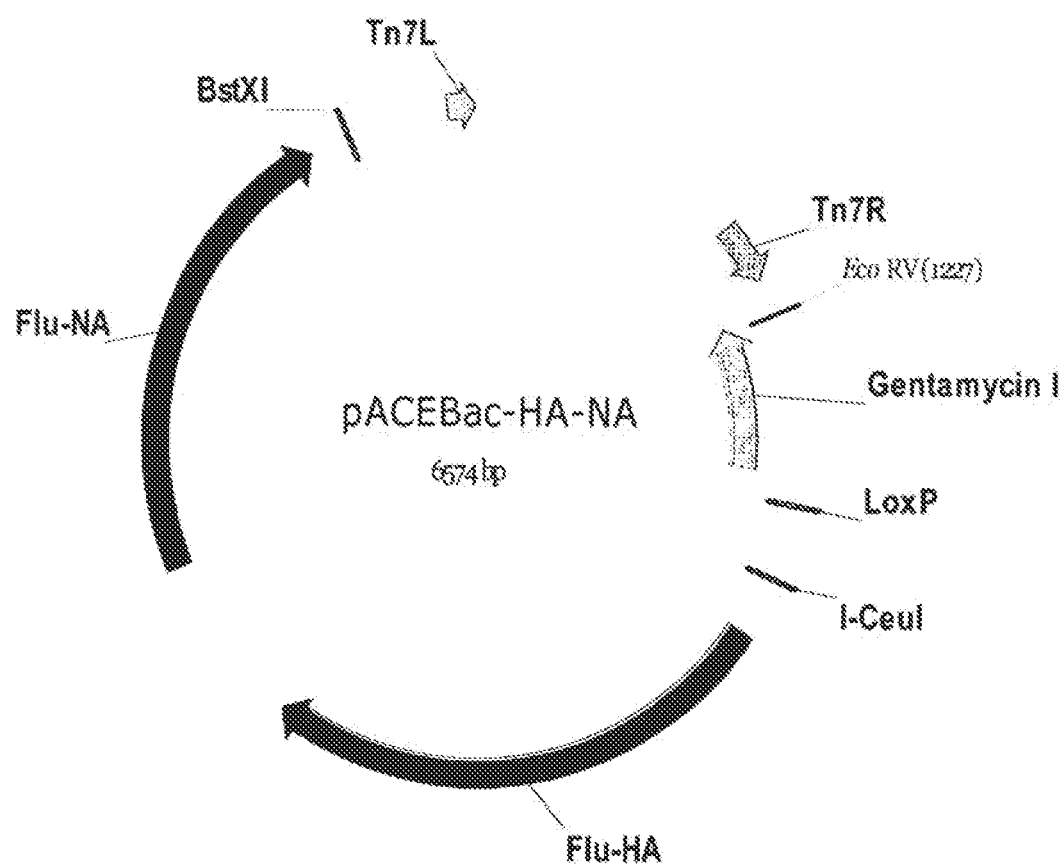

FIG. 49 shows a schematic representation of vector pACE-Bac-HA-NA.

Figure 50:
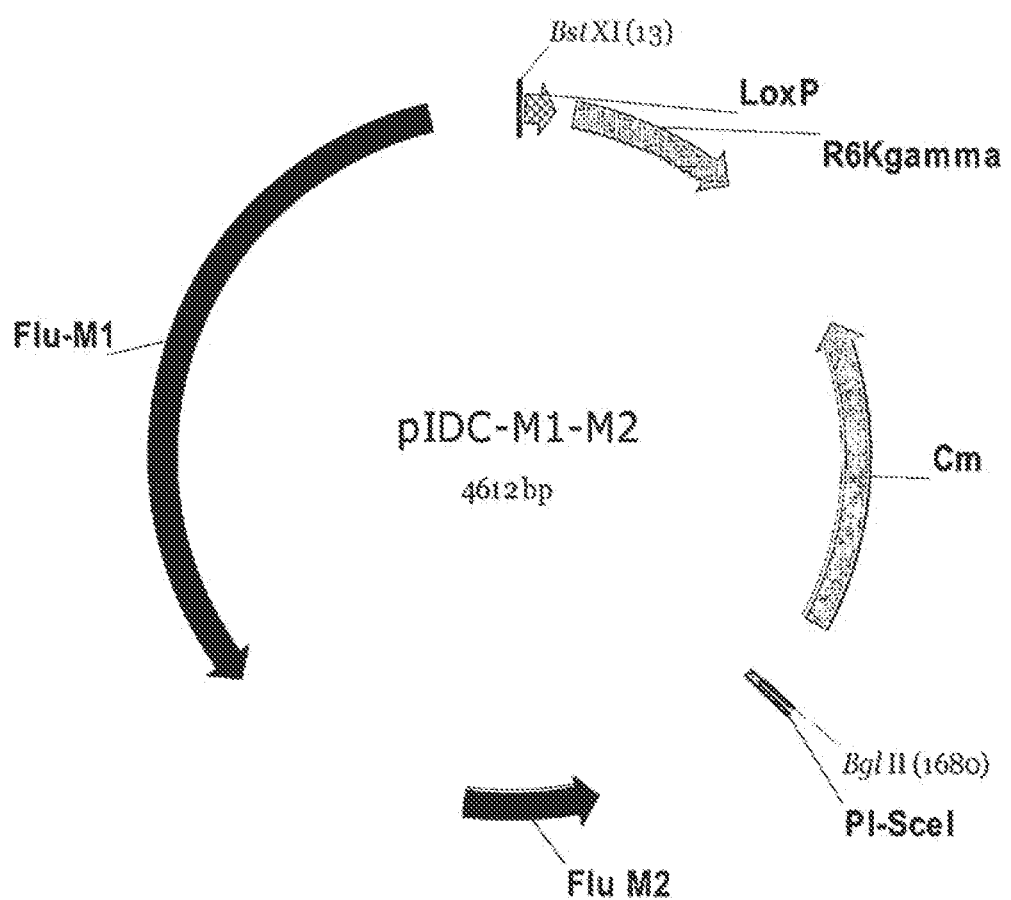

FIG. 50 shows a schematic representation of vector pIDC-M1-M2.

The present invention is in the following further described in detail with reference to preferred embodiments designated as "ACEMBL" system.

A. Synopsis

The preferred embodiments according to the present invention denoted as "ACEMBL" provide a multi-expression system for multigene expression in *E. coli* and insect cells using the baculovirus system. ACEMBL can be used both manually and also in an automated setup by using a liquid handling workstation. ACEMBL applies tandem recombination steps for rapidly assembling many genes into multigene expression cassettes. These can be polycistronic or multiple expression modules, or a combination of these elements. ACEMBL also offers the option to employ conventional approaches involving restriction enzymes and ligase, if desired.

The following strategies for multigene assembly and expression are provided for in the ACEMBL system:
(1) Single gene insertions into vectors (recombination or restriction/ligation)
(2) Multigene assembly into a polycistron (recombination or restriction/ligation)
(3) Multigene assembly using homing endonucleases
(4) Multigene plasmid fusion by Cre-LoxP reaction
(5) Multigene expression by cotransformation in *E. coli*
(6) Multigene expression in insect cells using the baculovirus system These strategies can be used individually or in conjunction, depending on the project and user.

In the following Section C, step-by-step protocols are provided for each of these methods for multigene cassette assembly that can be used in the ACEMBL system.

B. ACEMBL System

B.1 ACEMBL Vectors

The present invention provides as preferred exemplary embodiments small de novo designed vectors which are called "Acceptor" and "Donor" vectors (FIGS. 1 and 20; for plasmid maps, see FIGS. 14 to 18 and FIGS. 21 to 31). Acceptor vectors for expression of proteins in prokaryotic hosts (e.g. pACE, pACE2) contain origins of replication derived from ColE1 and resistance markers (ampicillin or tetracycline). Donor vectors contain conditional origins of replication (derived from R6Kγ), which make their propagation dependent on hosts expressing the pir gene. Donor vectors contain resistance markers kanamycin, chloramphenicol, and spectinomycin. Preferably, three Donor vectors are used in conjunction with one Acceptor vector.

All Donor and Acceptor vectors according the present example contain a LoxP imperfect inverted repeat and in addition, a multiple integration element (MIE). The preferred MIE of the invention comprises an expression cassette with a promoter of choice (prokaryotic, mammalian, insect cell specific or a combination thereof) and a terminator (prokaryotic, mammalian, insect cell specific or a combination thereof). In between is a DNA segment which contains a number of restriction sites that can be used for conventional cloning approaches or also for generating double-strand breaks for the integration of expression elements of choice (further promoters, ribosomal binding sites, terminators and genes). The MIE is completed by a homing endonuclease site and a specifically designed restriction enzyme site (BstXI) flanking the promoter and the terminator (see B.2.)

The sequences of ACEMBL vectors for expression in prokaryotic hosts are outlined in the sequence listing (pACE: SEQ ID NO: 2, pACE2: SEQ ID NO. 3; pDC: SEQ ID NO: 4; pDK: SEQ ID NO: 5; pDS: SEQ ID NO: 6; pACKS: SEQ ID NO: 18). Maps of the vectors pACE, pACE2, pDC, pDK and pDS are shown in FIGS. 14 to 18.

The ACEMBL system according to the present invention also provides Donor and Acceptor vectors adapted for expression of multiprotein complexes in insect cells using baculovirus (pIDC (SEQ ID NO: 7), pIDK (SEQ ID NO: 8), pIDS (SEQ ID NO: 9), pACEBac1 (SEQ ID NO: 10), pACEBac2 (SEQ ID NO: 11), pACEBac3 (SEQ ID NO: 12), pACEBac4 (SEQ ID NO: 13), pOmniBac1 (SEQ ID NO: 14), pOmniBac2 (SEQ ID NO: 15, pOmniBac3 (SEQ ID NO: 16) and pOmniBac4 (SEQ ID NO: 17)). Plasmid maps of the vectors are shown in FIGS. 24 to 34.

Donor vectors pIDS, pIDK and pIDS contain a conditional origin of replication (from R6Kgamma phage), a homing endonuclease (HE) site (PI-SceI) and a complementary BstXI site (see the corresponding *E. coli* vectors pDC, pDK, pDS). Donors are propagated in cell strains containing the pir gene.

In contrast to the versions adapted for expression in bacteria, the vectors for expression of proteins in insect cells do not contain prokaryotic promoter and terminator structures. Instead, they have either a polh expression cassette (polh EC) or a p10 expression cassette (p10 EC). These expression cassettes contain common polyhedron or p10 promoters from AcMNPV, an oligonucleotide encoding for restriction sites (different from the MIE in the prokaryotic ACEMBL version) and either SV40 or HSVtk polyadenylation signal sequences.

Obviously, due to the HE and BstXI sites, the expression cassettes can be freely exchanged in between the vectors, also if they contain an inserted gene. This can be done by restriction ligation or by restriction enzyme/ligase independent methods (e.g. SLIC). Therefore, versions can be created at ease which contain a p10 or polh marker in combination with any one of the resistance markers (spectinomycin, kanamycin, chloramphenicol, or others).

The HE/BstXI site combinations can be used to multiply expression cassettes or also to fit the vectors with combinations of p10 and polh expression cassettes.

All Donors contain a LoxP inverted imperfect repeat. This can be used for LoxP mediated constructions and deconstructions of Acceptor/Donor multifusions as described for the bacterial ACEMBL vectors.

The present embodiment of the invention relating to vectors adapted for protein expression in insect cells provides a number of Acceptor vectors in the baculovirus-version of ACEMBL. These share common features: all contain a LoxP site, a resistance marker (gentamycin) and again either a p10 or a polh expression cassette (identical to the ones present in the Donors).

The expression cassettes of the Acceptors are flanked by a homing endonuclease site (I-CeuI) and a corresponding BstXI site.

The expression cassettes can be exchanged in between the Acceptors and also multiplied or combined using the HE/BstXI combination as described for the bacterial ACEMBL vectors.

There are two families of Acceptors in terms of the origin used:

pACEBac1, pACEBac2, pOmniBac1 and pOmniBac2 contain all a ColEI origin of replication which allows propagation in all common *E. coli* cloning cell strains.

All Acceptor vectors contain the Tn7L and Tn7R sequences which enable integration of the region in between into a Tn7 attachment site by using the Tn7 transposition procedure.

pACEBac3, pACEBac4, pOmniBac3 and pOmniBac4 contain a conditional origin of replication (OriV) from *V. Cholerae* which is dependent on the trfA gene that needs to be provided in trans in the cloning strains used. The function of this OriV is to eliminate the background (blue colonies) when these Acceptors, fitted with genes and if required fused with Donors, are transformed into cells that contain the baculovirus genome in form of a bacterial artificial chromosome (i.e. DH10Bac from Invitrogen and similar). Here, the Tn7 transposition system is used to integrate the regions in between Tn7L and Tn7R of the DNA transformed into the cells into a Tn7 attachment site on the viral genome of choice. Normally, unproductive integration events would result in blue colonies (if the Tn7 attachment site is embedded in a LacZalpha gene on the baculovirus genome). These blue colonies propagate the plasmid transformed outside of the baculovirus genome. With these four OriV containing plasmids, the blue colonies cannot survive upon exposure to Gentamycin (since the DH10Bac or other cells do not contain trfA) and only white colonies are produced, which all contain productively integrated composite bacmid carrying the heterologous genes provided on the plasmid transformed; see also the scheme in FIG. 36.

The Acceptor vectors pOminBac1-4 contain, in addition to the Tn7L and Tn7R regions, also the lef2-603 and Orf1629 homology sequences. These are used for homologous recombination procedures for generating composite baculovirus as used by the Novagen Bacvector series, the Baculogold system from Pharmingen, FlashBac from OET and others. Thus, these Acceptor vectors can be used for every baculovirus system that is currently available, including the Tn7 based baculoviruses and all viruses relying on lef-2,603/1629 homologous recombination procedures, for expressing heterolgous genes in insect cell cultures; see also the scheme in FIG. 37.

B.2 Multiple Integration Element (MIE)

A preferred multiple integration element (MIE) according to the invention was derived from a polylinker (see Tan et al. (2005) supra) and allows for several approaches for multigene assembly (see Section C below). Multiple genes can be inserted into the MIE of any one of the vectors by a variety of methods, for example BD-In-Fusion recombination (see ClonTech TaKaRa Bio Europe, www.clontech.com) or SLIC (sequence and ligation independent cloning; see Li et al. (2007) *Nat. Methods* 4, 251). For this, the vector needs to be linearized, which can also be carried out efficiently by PCR reaction with appropriate primers, since the vectors are all small (2-3.0 kb). Use of ultrahigh-fidelity polymerases such as Phusion (Finnzymes/New England BioLabs, www.neb.com) is preferred. Alternatively, if more conventional approaches shall be used, e.g. in an ordinary wet lab setting without robotics, the vectors can also be linearized by restriction digestion, and a gene of interest can be integrated by restriction/ligation (see below Section C of the present embodiment). The DNA sequence (SEQ ID NO: 1) and map of the present MIE is shown in FIG. 13.

B3. Tags, Promoters, Terminators

For expression of proteins in prokaryotic hosts, the vectors of the ACEMBL system contain per default promoters T7 and Lac, as well as the T7 terminator element (FIGS. 1, 14). The T7 system requires bacterial strains which contain a T7 polymerase gene, e.g. in the *E. coli* genome. The Lac promoter is a strong endogenous promoter which can be utilized in most strains. The present ACEMBL vectors contain the lac operator element for repression of heterologous expression.

Evidently, all promoters and terminators present in ACEMBL Donor and Acceptor vectors, and in fact the entire multiple integration element (MIE), excluding the HE and X site, respectively, can be exchanged with an expression cassette of choice by using restriction/ligation cloning with appropriate enzymes (for example ClaI/PmeI, FIG. 2) or insertion into linearized ACEMBL vectors where the MIE was removed by sequence and ligation independent approaches such as SLIC. For example, the T7 promoter in pDC can be substituted with a trc promoter (pDC$^{trc}$), and the T7 promoter in pACE with an arabinose promoter (pACE$^{ara}$), Such variants can be used successfully in coexpression experiments by inducing with arabinose and IPTG.

In contrast to the ACEMBL vectors for expression in prokaryotic hosts, the vectors for expression in insect cells do not contain prokaryotic promoter and terminator structures. As already mentioned above, they have either a polh expression cassette (polh EC) or a p10 expression cassette (p10 EC). These expression cassettes contain common polyhedron or p10 promoters from AcMNPV, a sequence of restriction sites and either SV40 or HSVtk polyadenylation signal sequences.

The ACEMBL system vectors of the present example do not contain DNA sequences encoding for affinity tags to facilitate purification or solubilization of the protein(s) of interest. However, typically used C- or N-terminal oligohistidine tags, with or without protease sites for tag removal can be introduced by means of the respective PCR primers used for amplification of the genes of interest prior to insertion into the MIE, e.g. by SLIC-mediated insertion. Thus, Donor and Acceptor vectors of the present invention may be equipped by the array of custom tags prior to inserting recombinant genes of interest. This is best done by a design which will, after tag insertion, still be compatible with the recombination based principles of ACEMBL system usage.

B.4 Complex Expression

For expression in *E. coli*, the ACEMBL multigene expression vector fusions with appropriate promoters or terminators are transformed into the appropriate expression host of choice. With respect to the present exemplary vectors (T7 and lac promoter elements), most of the wide array of currently available expression strains can be utilized. If particular expression strains already contain helper plasmids with DNA encoding for chaperones, lysozyme or else, the design of the multigene fusion is preferably such that the ACEMBL vector containing the resistance marker that is also present on the helper plasmid is not included in multigene vector construction.

Alternatively, if further vectors are required for complex production in an experiment, the issue can be resolved by creating alternative versions of the ACEMBL vectors containing resistance markers that circumvent the conflict. This can be easily performed by PCR amplifying the vectors minus the resistance marker, and combine the resulting fragments with a PCR amplified resistance marker by recombination (SLIC) or blunt-end ligation (using 5' phosphorylated primers).

Donor vectors of the present example depend on expression by the host of the pir gene product, due to the R6Kγ conditional origin of replication. In regular expression strains, they rely on fusion with an Acceptor for productive replication. Donors or Donor-Donor fusions can nonetheless be used even for expression when not fused with an Acceptor, by using expression strains carrying a genomic insertion of the pir gene. Such strains are commercially available (Novagen Inc., Madison Wis., USA).

Cotransformation of two ACEMBL plasmids adapted for expression in bacteria can lead to a successful protein complex expression. The present ACEMBL system for expression in prokaryotic hosts contains two Acceptor vectors, pACE and pACE2, which are identical except for the resistance marker (FIGS. 1, 14). These can be used to express genes present on pACE or pACE2, respectively, by cotransformation and exposure to both antibiotics simultaneously. In fact, entire Acceptor-Donor fusions containing several genes, based on pACE or pACE2 as Acceptors, can in principle be cotransformed for multi-expression, if needed.

For expression in insect cells (such as Sf9, Sf21, Hi5 etc.) using the baculovirus system, suitable ACEMBL vectors of the present invention need to be integrated into a baculovirus genome (composite virus generation). This is typically carried out by transformation of the desired Cre-LoxP fusion into bacterial cells containing the desired virus genome as a bacterial artificial chromosome. Using the vector system of the present invention adapted for baculovirus integration is used, three approaches are possible as outlined in FIGS. 35, 36 and 37, respectively.

C. Procedures

C.1. Cloning into ACEMBL Vectors

All Donors and Acceptors of the preferred embodiment for expression prokaryotic hosts contain an identical MIE with exception of the homing endonuclease site/BstXI tandem encompassing the MIE (FIGS. 1 and 14). The MIE is tailored for sequence and ligation independent gene insertion methods. In addition, the MIE also contains a series of unique restriction sites, and therefore can be used as a classical polylinker for conventional gene insertion by restriction/ligation. For automated applications insertion of genes of interest is preferably carried out by recombination approaches such as SLIC.

The Donor vectors for expression in insect cells according to the present preferred embodiment also contain an MIE which is, however, different for each vector (see plasmid maps of vectors pIDC, pIDK and pIDS in FIGS. 21, 22 and 23, respectively).

C1.1. Single Gene Insertion into the MIE by SLIC

Several procedures for restriction/ligation independent insertion of genes into vectors have been published or commercialized (e.g. Novagen LIC, Becton-Dickinson BD InFusion etc.). These systems share in common that they rely on the exonuclease activity of DNA polymerases. In the absence of dNTPs, 5' extensions are created from blunt ends or overhangs by digestion from the 3' end. If two DNA fragments contain the same ~20-30 bp sequence at their termini at opposite ends, this results in overhangs that share complementary sequences capable of annealing. This can be exploited for ligation independent combination of two or several DNA fragments containing homologous sequences.

If T4 DNA polymerase is used, this can be carried out in a manner that is independent of the sequences of the homology regions (Sequence and Ligation Independent Cloning, SLIC) and detailed protocols are available for the skilled person. In the context of multiprotein expression, this is particularly useful, as this approach is independent of the presence of unique restriction sites, or of their creation by mutagenesis, in the ensemble of encoding DNAs.

For use in the context of the present invention, the SLIC process was adapted for inserting encoding DNAs amplified by Phusion polymerase into the ACEMBL Acceptor and Donor vectors. In this way, not only seamless integration of genes into the expression cassettes, but also concatamerization of expression cassettes to multigene constructs can be achieved by applying the same, simple routine that can be readily automated.

The following Protocol 1 represents an improved process based on the method described in Li et al. (2007, supra). Protocol 1 is designed for manual operation. Other systems may be used (e.g. BD-InFusion etc.), and if so, the manufacturers' recommendations should be followed. The present protocol may be adopted for robotics applications. Corresponding modifications of the protocol are outlined in Section D).

Protocol 1: Single Gene Insertion by SLIC.

Reagents Required:
  Phusion Polymerase
  5×HF Buffer for Phusion Polymerase
  dNTP mix (10 mM)
  T4 DNA polymerase (and 10× Buffer)
  DpnI enzyme
  *E. coli* competent cells
  100 mM DTT, 2M Urea, 500 mM EDTA
  Antibiotics Step 1: Primer Design Primers for the SLIC procedure are designed to provide the regions of homology which result in the long sticky ends upon treatment with T4 DNA polymerase in the absence of dNTP:

Primers for the insert contain a DNA sequence corresponding to this region of homology ("Adaptor sequence" in FIG. 3, inset), followed by a sequence which specifically anneals to the insert to be amplified (FIG. 3, inset). Useful examples of adaptor sequences for SLIC are listed below (Table I).

This "insert specific sequence" can be located upstream of a ribosome binding site (rbs), for example if the gene of interest (GOI) is amplified from a vector already containing expression elements (e.g. the pET vector series). Otherwise, the forward primer needs to be designed such that a ribosome binding site is also provided in the final construct (FIG. 3, inset).

Primers for PCR linearization of the vector backbone are simply complementary to the two adaptor sequences present in the primer pair chosen for insert amplification (FIG. 3).

Step 2: PCR Amplification of Insert and Vector

Identical reactions are prepared in 100 μl volume for DNA insert to be cloned and vector to be linearized by PCR:

| | |
|---|---|
| ddH$_2$O | 75 μl |
| 5× Phusion HF Reaction buffer | 20 μl |
| dNTPs (10 mM stock) | 2 μl |
| Template DNA (100 ng/μl) | 1 μl |
| 5 SLICprimer (100 μM stock) | 1 μl |
| 3 SLICprimer (100 μM stock) | 1 μl |
| Phusion polymerase (2 U/μl) | 0.5 μl |

PCR reactions are then carried out with a standard PCR program (unless very long DNAs are amplified, then double extension time):

1×98° C. for 2 min
  30×[98° C. for 20 sec.→50° C. for 30 sec.→72° C. for 3 min]
  Hold at 10° C.

Analysis of the PCR reactions by agarose gel electrophoresis and ethidium bromide staining is recommended.

Step 3: DpnI Treatment of PCR Products (Optional)

PCR reactions are then supplied with 1 µl DpnI enzyme which cleaves parental plasmids (that are methylated). For insert PCR reactions, DpnI treatment is not required if the resistance marker of the template plasmid differs from the destination vector.

Reactions are then Carried Out as Follows:
  Incubation: 37° C. for 1-4 h
  Inactivation: 80° C. for 20 min Step 4: Purification of PCR Products PCR products should be cleaned of residual dNTPs. Otherwise, the T4 DNA polymerase reaction (Step 5) is compromised. Product purification is preferably performed by using commercial PCR Purification Kits or NucleoSpin Kits (e.g. from Qiagen, Macherey-Nagel etc.). It is recommended to perform elution in the minimal possible volume indicated by the respective manufacturer.

Step 5: T4 DNA Polymerase Exonuclease Treatment

Identical reactions are prepared in 20 µl volume for insert and for vector (eluted in Step 4):

| | |
|---|---|
| 10x T4 DNA polymerase buffer | 2 µl |
| 100 mM DTT | 1 µl |
| 2M Urea | 2 µl |
| DNA eluate from Step 3 (vector or insert) | 14 µl |
| T4 DNA polymerase | 1 µl |

Reactions are then Carried Out as Follows:
  Incubation: 23° C. for 20 min
  Arrest: Addition of 1 µl 500 mM EDTA
  Inactivation: 75° C. for 20 min Step 6: Mixing and Annealing T4 DNA polymerase exonuclease-treated insert and vector are then mixed, followed by an (optional) annealing step which enhances the efficiency:
  T4 DNA pol-treated insert: 10 µl
  T4 DNA pol-treated vector: 10 µl
  Annealing: 65° C. for 10 min
  Cooling: Slowly (in heat block) to RT (room temperature)

Step 7: Transformation

Mixtures are next transformed into competent cells following standard transformation procedures.

Reactions for pACE and pACE2 derivatives are transformed into standard *E. coli* cells for cloning (such as TOP10, DH5α, HB101) and after recovery (2-4 h) plated on agar containing ampicillin (100 µg/ml) or tetracycline (25 µg/ml), respectively.

Reactions for Donor derivatives are transformed into *E. coli* cells expressing the pir gene (such as BW23473, BW23474, or PIR1 and PIR2, Invitrogen) and plated on agar containing chloramphenicol (25 µg/ml, pDC), kanamycin (50 µg/ml, pDK), and spectinomycin (50 µg/ml, pDS).

Step 8: Plasmid Analysis

Plasmids are cultured in small-scale in media containing the corresponding antibiotic, and analyzed by sequencing and (optionally) restriction mapping with an appropriate restriction enzyme.

C1.2. Polycistron Assembly in MIE by SLIC

The multiple integration element according to the present invention can also be used to integrate genes of interest by using multi-fragment SLIC recombination as shown in FIG. 4. Genes preceded by ribosome binding sites (rbs) can be assembled in this way into polycistrons.

A detailed protocol is outlined in the following Protocol 2:

Protocol 2. Polycistron Assembly by SLIC.

Reagents Required:
  Phusion Polymerase
  5×HF Buffer for Phusion Polymerase
  dNTP mix (10 mM)
  T4 DNA polymerase (and 10× Buffer)
  *E. coli* competent cells
  100 mM DTT, 2M Urea, 500 mM EDTA
  Antibiotics Step 1: Primer Design The MIE element according to the present embodiment is composed of tried-and-tested primer sequences. These constitute the "Adaptor" sequences that can be used for inserting single genes or multigene constructs. Examples of useful adaptor sequences are listed below (see Table I).

Adaptor sequences form the 5' segments of the primers used to amplify DNA fragments to be inserted into the MIE. Insert specific sequences are added at 3', DNA coding for a ribosome binding sites can be inserted optionally, if not already present on the PCR template.

Step 2: PCR Amplification of Insert and Primer

Identical reactions are prepared in 100 µl volume for all DNA insert (GOI 1, 2, 3) to be cloned and the vector to be linearized by PCR:

| | |
|---|---|
| ddH$_2$O | 75 µl |
| 5x Phusion HF Reaction buffer | 20 µl |
| dNTPs (10 mM stock) | 2 µl |
| Template DNA (100 ng/µl) | 1 µl |
| 5' SLIC primer (100 µM stock) | 1 µl |
| 3' SLIC primer (100 µM stock) | 1 µl |
| Phusion polymerase (2 U/µl) | 0.5 µl |

PCR reactions are then carried out with a standard PCR program (unless very long DNAs are amplified, then double extension time):
  1×98° C. for 2 min
  30×[98° C. for 20 sec.→50° C. for 30 sec.→72° C. for 3 min]
  Hold at 10° C.

Analysis of the PCR reactions by agarose gel electrophoresis and ethidium bromide staining is recommended.

Step 3: DpnI Treatment of PCR Products (Optional)

PCR reactions are then supplied with 1 µl DpnI enzyme which cleaves parental plasmids (that are methylated). For insert PCR reactions, DpnI treatment is not required if the resistance marker of the template plasmids differs from the destination vector.

Reactions are then Carried Out as Follows:
  Incubation: 37° C. for 1-4 h
  Inactivation: 80° C. for 20 min Step 4: Purification of PCR Products PCR products should be cleaned of residual dNTPs. Otherwise, the T4 DNA polymerase reaction (Step 5) is compromised.

Product purification is preferably performed by using commercial PCR Purification Kits or NucleoSpin Kits (Qiagen, Macherey-Nagel or others). It is recommended to perform elution in the minimal possible volume indicated by the respective manufacturer.

Step 5: T4 DNA Polymerase Exonuclease Treatment

Identical reactions are prepared in 20 μl volume for each insert (GOI 1, 2, 3) and for the vector (eluted in Step 4):

| | |
|---|---|
| 10x T4 DNA polymerase buffer | 2 μl |
| 100 mM DTT | 1 μl |
| 2M Urea | 2 μl |
| DNA eluate from Step 3 (vector or insert) | 14 μl |
| T4 DNA polymerase | 1 μl |

Reactions are then Carried Out as Follows:

Incubation: 23° C. for 20 min

Arrest: Addition of 1 μl 500 mM EDTA

Inactivation: 75° C. for 20 min

Step 6: Mixing and Annealing

T4 DNA polymerase exonuclease-treated insert and vector are then mixed, followed by an (optional) annealing step which enhances efficiency.

T4 DNA pol-treated insert 1 (GOI 1): 5 μl

T4 DNA pol-treated insert 2 (GOI 2): 5 μl

T4 DNA pol-treated insert 3 (GOI 3):

T4 DNA pol-treated vector: 5 μl

Annealing: 65° C. for 10 min

Cooling: Slowly (in heat block) to RT

Step 7: Transformation

Mixtures are next transformed into competent cells following standard transformation procedures.

Reactions for pACE and pACE2 derivatives are transformed into standard *E. coli* cells for cloning (such as TOP10, DH5α, HB101) and after recovery plated on agar containing ampicillin (100 μg/ml) or tetracycline (25 μg/ml), respectively.

Reactions for Donor derivatives are transformed into *E. coli* cells expressing the pir gene (such as BW23473, BW23474, or PIR1 and PIR2, available from Invitrogen) and plated on agar containing chloramphenicol (25 μg/ml, pDC), kanamycin (50 μg/ml, pDK), and spectinomycin (50 μg/ml, pDS).

Step 8: Plasmid Analysis

Plasmids are cultured and correct clones are selected based on specific restriction digestion and DNA sequencing of the inserts.

TABLE I

Adaptor DNA sequences.
For single gene or multigene insertions into ACEMBL vectors by SLIC.

Figure 2:
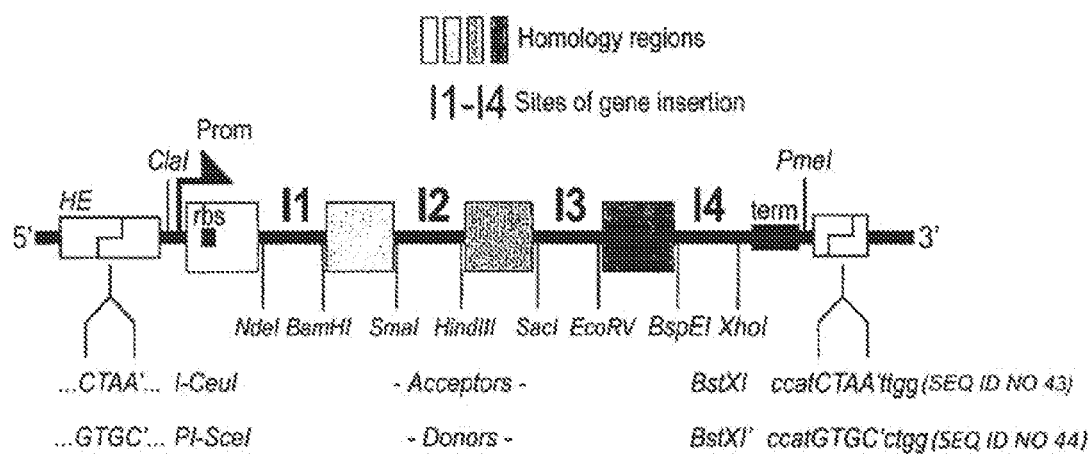
FIG. 2 is a graphic representation of a preferred embodiment of the nucleic acid of the present invention called "multiple integration element" (MIE).

| Adaptor* | Sequence | Description |
|---|---|---|
| (a) Adaptors for cloning into ACEMBL vectors for expression in prokaryotic hosts | | |
| T7InsFor | TCCCGCGAAATTAATA CGACTCACTATAGGG (SEQ ID NO: 20) | Forward primer for insert amplification, if gene of interest (GOI) is present in a T7 system vector (i.e. pET series). No further extension (rbs, insert specific overlap) required. |
| T7InsRev | CCTCAAGACCCGTTTA GAGGCCCCAAGGGGT TATGCTAG (SEQ ID NO: 21) | Reverse primer for insert amplification, if GOI is present in a T7 system vector (i.e. pET series). No further extension (stop codon, insert specific overlap) required. |
| T7VecFor | CTAGCATAACCCCTTG GGGCCTCTAAACGGG TCTTGAGG (SEQ ID NO: 22) | Forward primer for vector amplification, reverse complement of T7InsRev. No further extension required. |
| T7VecRev | CCCTATAGTGAGTCGT ATTAATTTCGCGGGA (SEQ ID NO: 23) | Reverse primer for vector amplification, reverse complement of T7InsFor. No further extension required. |
| NdeInsFor | GTTTAACTTTAAGAAG GAGATATACATATG (SEQ ID NO: 24) | Forward primer for insert amplification for insertion into MIE site I1 (FIG. 2). Further extension at 3' (insert specific overlap) required. Can be used with adaptor XhoInsRev in case of single fragment SLIC (FIG. 3). |
| XhoInsRev | GGGTTTAAACGGAACT AGTCTCGAG (SEQ ID NO: 25) | Reverse primer for insert amplification for insertion into MIE site I4 (FIG. 2). Further extension at 3' (stop codon, insert specific overlap) required. Can be used with adaptor NdeInsFor in case of single fragment SLIC (FIG. 3). |
| XhoVecFor | CTCGAGACTAGTTCCG TTTAAACCC (SEQ ID NO: 26) | Forward primer for vector amplification, reverse complement of XhoInsRev. No further extension required. |
| NdeVecRev | CATATGTATATCTCCTT CTTAAAGTTAAAC (SEQ ID NO: 27) | Reverse primer for vector amplification, reverse complement of NdeInsFor. No further extension required. |
| SmaBam | GAATTCACTGGCCGTC GTTTTACAGGATCC (SEQ ID NO: 28) | Reverse primer for insert amplification (GOI1) for insertion into MIE site I1 (FIG. 2). Further extension at 3' (stop codon, insert specific overlap) required. Use with adaptor NdeInsFor. |

TABLE I-continued

Adaptor DNA sequences.
For single gene or multigene insertions into ACEMBL vectors by SLIC.

| Adaptor* | Sequence | Description |
|---|---|---|
| BamSma | GGATCCTGTAAAACGACGGCCAGTGAATTC (SEQ ID NO: 29) | Forward primer for insert amplification (GOI2) for insertion into site I2 (FIG. 2, 4). Further extension at 3' (rbs, insert specific over-lap) required. Use with adaptor SacHind. (multifragment SLIC, FIG. 4) |
| SacHind | GCTCGACTGGGAAAACCCTGGCGAAGCTT (SEQ ID NO: 30) | Reverse primer for insert amplification (GOI2) insertion into MIE site I2 (FIG. 2, 4). Further extension at 3' (stop codon, insert specific overlap) required. Use with adaptor BamSma. (multifragment SLIC, FIG. 4) |
| HindSac | AAGCTTCGCCAGGGTTTTCCCAGTCGAGC (SEQ ID NO: 31) | Forward primer for insert amplification (GOI3) for insertion into site I3 (FIG. 2, 4). Further extension at 3' (rbs, insert specific over-lap) required. Use with adaptor BspEco. (multifragment SLIC, FIG. 4) |
| BspEco5 | GATCCGGATGTGAAATTGTTATCCGCTGGTACC (SEQ ID NO: 32) | Reverse primer for insert amplification (GOI3) insertion into MIE site I3 (FIG. 2, 4). Further extension at 3' (stop codon, insert specific overlap) required. Use with adaptor HindSac. (multifragment SLIC, FIG. 4) |
| Eco5Bsp | GGTACCAGCGGATAACAATTTCACATCCGGATC (SEQ ID NO: 33) | Forward primer for insert amplification (GOI3) for insertion into site I4 (FIG. 2, 4). Further extension at 3' (rbs, insert specific over-lap) required. Use with adaptor XhoInsRev. (multi-fragment SLIC, FIG. 4) |
| (b) Adaptors for cloning into ACEMBL vectors for expression in insect cells | | |
| PolhInsFor | CCCACCATCGGGCGCGGATCCG (SEQ ID NO: 34) | Forward primer for insert amplification, needs to be followed by insert specific sequence (ca. 20 bp) |
| PolhInsRev | CGAGACTGCAGGCTCTAGATTCG (SEQ ID NO: 35) | Reverse primer for insert amplification, needs to be followed by insert specific sequence (ca. 20 bp) |
| PolhVecFor | CGGGATCCGCGCCCGATGGTGGG (SEQ ID NO: 36) | Forward primer for vector amplification, reverse complement of PolhInsRev. No further extension required. |
| PolhVecRev | CGAATCTAGAGCCTGCAGTCTCG (SEQ ID NO: 37) | Reverse primer for vector amplification, reverse complement of PolhInsFor. No further extension required. |
| P10hInsFor | CTCCCGGTACCGCATGCTATGCATCAGC (SEQ ID NO: 38) | Forward primer for insert amplification, needs to be followed by insert specific sequence (ca. 20 bp) |
| P10InsRev | AATCACTCGACGAAGACTTGATCACC (SEQ ID NO: 39) | Reverse primer for insert amplification, needs to be followed by insert specific sequence (ca. 20 bp) |
| P10VecFor | GCTGATGCATAGCATGCGGTACCGGGAG (SEQ ID NO: 40) | Forward primer for vector amplification, reverse complement of P10InsRev. No further extension required. |
| P10VecRev | GGTGATCAAGTCTTCGTCGAGTGATT (SEQ ID NO: 41) | Reverse primer for vector amplification, reverse complement of P10InsFor. No further extension required. |

*All Adaptor primers (without extension) can be used as sequencing primers for genes of interest that were inserted into the MIE according to the present embodiment.

C.1.3. Gene Insertion by Restriction/Ligation

The MIEs of the present invention can also be used as a multiple cloning site with a series of unique restriction sites. Preferably, the MIE described herein for expression of proteins in prokaryotic hosts is preceded by a promoter and a ribosome binding site, and followed by a terminator. The MIEs of the preferred embodiments described herein for expression of proteins in insect cells contain a polh expression cassestte or a p10 expression cassette as already mentioned above. Therefore, cloning into the MIE by classical restriction/ligation also yields functional expression cassettes.

Genes of interest (GOI) can be subcloned by using standard cloning procedures into the multiple integration element (MIE) (see, for example, FIG. 13) of ACEMBL vectors.
Protocol 3. Restriction/Ligation Cloning into an MIE.
Reagents Required:
  Phusion Polymerase
  5×HF Buffer for Phusion Polymerase
  dNTP mix (10 mM)
  10 mM BSA
  Restriction endonucleases (and 10× Buffer)
  T4 DNA ligase (and 10× Buffer)
  Calf or Shrimp intestinal alkaline phosphatase
  *E. coli* competent cells
  Antibiotics
Step 1: Primer Design
  For conventional cloning, PCR primers are designed containing chosen restriction sites, preceded by appropriate overhangs for efficient cutting (see, e.g. New England Biolabs catalogue), and followed by ≥20 nucleotides overlapping with the gene of interest that is to be inserted.

In the case of the ACEMBL system for expression in bacteria, the MIE of the present embodiment is identical for all ACEMBL vectors. They contain a ribosome binding preceding the NdeI site. For single gene insertions, therefore, an rbs need not be included in the primer.

If multigene insertions are needed (for example in insertion sites I1-I4 of the MIE), primers should be designed such that an rbs preceding the gene and a stop codon at its 3' end are provided.

In particular for polycistron cloning by restriction/ligation, it is recommended to construct templates by custom gene synthesis. In the process, the restriction sites present in the MIE can be eliminated from the encoding DNAs.

Step 2: Insert Preparation
PCR of Insert(s):
Identical PCR reactions are prepared in 100 μl volume for genes of interest to be inserted into the MIE:

| | |
|---|---|
| ddH$_2$O | 75 μl |
| 5x Phusion HF Reaction buffer | 20 μl |
| dNTPs (10 mM stock) | 2 μl |
| Template DNA (100 ng/μl) | 1 μl |
| 5 primer (100 μM stock) | 1 μl |
| 3 primer (100 μM stock) | 1 μl |
| Phusion polymerase (2 U/μl) | 0.5 μl |

PCR reactions are then carried out with a standard PCR program (unless very long DNAs are amplified, then double extension time):

1×98° C. for 2 min
30×[98° C. for 20 sec.→50° C. for 30 sec.→72° C. for 3 min]
Hold at 10° C.

Analysis of the PCR reactions by agarose gel electrophoresis and ethidium bromide staining is recommended.

Product purification is preferably performed by using commercial PCR Purification Kits or NucleoSpin Kits (available from Qiagen, Macherey-Nagel and other manufacturers). It is recommended to perform elution in the minimal possible volume indicated by the manufacturer.

Restriction Digestion of Insert(s):
Restriction reactions are carried out in 40 μl reaction volumes, using specific restriction enzymes as specified by manufacturer's recommendations (c.f. New England Biolabs catalogue and others).

| | |
|---|---|
| PCR Kit eluate (≥1 μg) | 30 μl |
| 10x Restriction enzyme buffer | 4 μl |
| 10 mM BSA | 2 μl |
| Restriction enzyme for 5' | 2 μl |
| Restriction enzyme for 3' | 2 μl (in case of double digestion, otherwise ddH$_2$O) |

Restriction digestions are performed in a single reaction with both enzymes (double digestion), or, alternatively, sequentially (two single digestions) if the buffer conditions required are incompatible.

Gel Extraction of Insert(s):
Processed insert is then purified by agarose gel extraction using commercial kits (Qiagen, Macherey-Nagel etc). It is recommended to elute the extracted DNA in the minimal volume defined by the respective manufacturer.

Step 3: Vector Preparation
Restriction Digestion of ACEMBL Plasmid(s):
Restriction reactions are carried out in 40 μl reaction volumes, using specific restriction enzymes as specified by manufacturer's recommendations (see, e.g. New England Biolabs catalogue and others).

| | |
|---|---|
| ACEMBL plasmid (≥0.5 μg) in ddH$_2$O | 30 μl |
| 10x Restriction enzyme buffer | 4 μl |
| 10 mM BSA | 2 μl |
| Restriction enzyme for 5' | 2 μl |
| Restriction enzyme for 3' | 2 μl (in case of double digestion, otherwise ddH$_2$O) |

Restriction digestions are performed in a single reaction with two enzymes (double digestion), or, alternatively, sequentially (two single digestions), if the buffer conditions required are incompatible.

Gel Extraction of Vector(s):
The processed vector is then purified by agarose gel extraction using commercial kits (Qiagen, Macherey-Nagel etc.). It is recommended to elute the extracted DNA in the minimal volume defined by the respective manufacturer.

Step 4: Ligation
Ligation reactions are carried out in 20 μl reaction volumes according to the recommendations of the supplier of the T4 DNA ligase:

| | |
|---|---|
| ACEMBL plasmid (gel extracted) | 8 μl |
| Insert (gel extracted) | 10 μl |
| 10x T4 DNA Ligase buffer | 2 μl |
| T4 DNA Ligase | 0.5 μl |

Ligation reactions are performed at 25° C. (sticky end) for 1 h or at 16° C. (blunt end) overnight.

Step 5: Transformation
Mixtures are next transformed into competent cells following standard transformation procedures.

Reactions for Acceptor derivatives are transformed into standard E. coli cells for cloning (such as TOP10, DH5α, HB101) and after recovery plated on agar containing ampicillin (100 μg/ml) or tetracycline (25 μg/ml), respectively. Reactions for Donor derivatives are transformed into E. coli cells expressing the pir gene (such as BW23473, BW23474, or PIR1 and PIR2, Invitrogen) and plated on agar containing chloramphenicol (25 μg/ml, pDC), kanamycin (50 μg/ml, pDK), and spectinomycin (50 μg/ml, pDS).

Step 6: Plasmid Analysis
Plasmids are cultured and correct clones are selected based on specific restriction digestion and DNA sequencing of the inserts.

C.1.4. Multiplication by Using the HE and BstXI Sites
The ACEMBL system vectors according to the present invention contain a homing endonuclease (HE) site and a designed BstXI site that envelop the multiple integration element (MIE). The homing endonuclease site can be used to insert entire expression cassettes, containing single genes or polycistrons, into a vector already containing one gene or several genes of interest. Homing endonucleases have long recognition sites (12 to 40 base pairs or more, preferably 20-30 base pairs). Although not all equally stringent, homing endonuclease sites are most probably unique in the context of even large plasmids, or, in fact, entire genomes.

In the ACEMBL system of the present embodiment, Donor vectors contain a recognition site for homing endonuclease PI-SceI (FIG. 2). This HE site yields upon cleavage a 3' overhang with the sequence -CTGC. Acceptor vectors contain the homing endonuclease site I-CeuI, which upon cleavage will result in a 3' overhang of -CTAA. On Acceptors and Donors, the respective HE site is preceding the MIE. The 3' end of the MIE contains a specifically designed BstXI site, which upon cleavage will generate a matching overhang. The basis of this is the specificity of cleavage by BstXI. The recognition sequence of BstXI is defined as CCANNNNN'NTGG (SEQ ID NO: 42) (apostrophe marks position of phosphodiester link cleavage). The residues denoted as N can be chosen freely. Donor vectors thus contain a BstXI recognition site of the sequence CCATGTGC'CTGG (SEQ ID NO: 43), and Acceptor vectors contain CCATCTAA'TTGG (SEQ ID NO: 44). The overhangs generated by BstXI cleavage in each case will match the overhangs generated by HE cleavage. Note that Acceptors and Donors have different HE sites.

The recognition sites are not symmetric. Therefore, ligation of a HE/BstXI digested fragment into a HE site of an ACEMBL vector will be (1) directional and (2) result in a hybrid DNA sequence where a HE half site is combined with a BstXI half site. This site will be cut by neither HE nor BstXI. Therefore, in a construct that had been digested with a HE, insertion by ligation of HE/BstXI digested DNA fragment containing an expression cassette with one or several genes will result in a construct which contains all heterologous genes of interest, enveloped by an intact HE site in front, and a BstXI site at the end. Therefore, the process of integrating entire expression cassettes by means of HE/BstXI digestion and ligation into a HE site can be repeated iteratively.

Protocol 4. Multiplication by Using Homing Endonuclease/BstXI.

Reagents Required:
Homing endonucleases PI-SceI, I-CeuI
10× Buffers for homing endonucleases
Restriction enzyme BstXI (and 10× Buffer)
T4 DNA ligase (and 10× Buffer)
E. coli competent cells
Antibiotics Step 2: Insert Preparation Restriction reactions are carried out in 40 µl reaction volumes, using homing endonucleases PI-SceI (Donors) or I-CeuI (Acceptors) as recommended by the supplier (e.g. New England Biolabs or others).

| ACEMBL plasmid (≥0.5 µg) in ddH$_2$O | 32 µl |
|---|---|
| 10× Restriction enzyme buffer | 4 µl |
| 10 mM BSA | 2 µl |
| PI-SceI (Donors) or I-CeuI (acceptors) | 2 µl |

Reactions are then purified by PCR extraction kit or acidic ethanol precipitation, and next digested by BstXI according to the recommendations of the supplier.

| HE digested DNA in ddH$_2$O | 32 µl |
|---|---|
| 10× Restriction enzyme buffer | 4 µl |
| 10 mM BSA | 2 µl |
| BstXI | 2 µl |

Gel Extraction of Insert(s):

Processed insert is then purified by agarose gel extraction using commercial kits (Qiagen, Macherey-Nagel etc). It is recommended to elute the extracted DNA in the minimal volume defined by the respective manufacturer.

Step 3: Vector Preparation

Restriction reactions are carried out in 40 µl reaction volumes, using homing endonucleases PI-SceI (Donors) or I-CeuI (Acceptors) as recommended by the supplier (e.g. New England Biolabs catalogue or others).

| ACEMBL plasmid (≥0.5 µg) in ddH$_2$O | 33 µl |
|---|---|
| 10× Restriction enzyme buffer | 4 µl |
| 10 mM BSA | 2 µl |
| PI-SceI (Donors) or I-CeuI (acceptors) | 1 µl |

Reactions are then purified by PCR extraction kit or acidic ethanol precipitation, and next treated with intestinal alkaline phosphatase according to the recommendations of the respective supplier.

| HE digested DNA in ddH$_2$O | 17 µl |
|---|---|
| 10× Alkaline phosphatase buffer | 2 µl |
| Alkaline phosphatase | 1 µl |

Gel Extraction of Vector:

Processed vector is then purified by agarose gel extraction using commercial kits (Qiagen, Macherey-Nagel etc). It is recommended to elute the extracted DNA in the minimal volume defined by the respective manufacturer.

Step 4: Ligation

Ligation reactions are carried out in 20 µl reaction volumes:

| HE/Phosphatase treated vector (gel extracted) | 4 µl |
|---|---|
| HE/BstXI treated insert (gel extracted) | 14 µl |
| 10× T4 DNA Ligase buffer | 2 µl |
| T4 DNA Ligase | 0.5 µl |

Ligation reactions are performed at 25° C. for 1 h or at 16° C. overnight.

Step 5: Transformation

Mixtures are next transformed into competent cells following standard transformation procedures.

Reactions for Acceptor derivatives are transformed into standard E. coli cells for cloning (such as TOP10, DH5α, HB101) and after recovery plated on agar containing ampicillin (100 µg/ml) or tetracycline (25 µg/ml), respectively.

Reactions for Donor derivatives are transformed into E. coli cells expressing the pir gene (such as BW23473, BW23474, or PIR1 and PIR2, Invitrogen) and plated on agar containing chloramphenicol (25 µg/ml, pDC, pIDC), kanamycin (50 µg/ml, pDK, pIDK), and spectinomycin (50 µg/ml, pDS, pIDS).

Step 6: Plasmid Analysis

Plasmids are cultured and correct clones selected based on specific restriction digestion and DNA sequencing of the inserts.

C.2. Cre-LoxP Reaction of Acceptors and Donors

Cre recombinase is a member of the integrase family (Type I topoisomerase from bacteriophage P1). It recombines a 34 bp loxP site (SEQ ID NO: 19; see FIG. 5) in the absence of accessory protein or auxiliary DNA sequence. The loxP site is comprised of two 13 bp recombinase-binding elements arranged as inverted repeats which flank an 8 bp central region where cleavage and ligation reaction occur.

The site-specific recombination mediated by Cre recombinase involves the formation of a Holliday junction (HJ). The recombination events catalyzed by Cre recombinase are dependent on the location and relative orientation of the LoxP sites. Two DNA molecules, for example an Acceptor and a Donor plasmid, containing single LoxP sites will be fused. Furthermore, the Cre recombination is an equilibrium reaction with 15-20% efficiency in recombination. This creates useful options for multigene combinations for multiprotein complex expressions.

In a reaction where several DNA molecules such as Donors and Acceptors are incubated with Cre recombinase, the fusion/excision activity of the enzyme will result in an equilibrium state where single vectors (educt vectors) and all possible fusions coexist. Donor vectors can be used with Acceptors and/or Donors, likewise for Acceptor vectors. Higher order fusions are also generated where more than two vectors are fused. This is shown schematically in FIG. 6.

The fact that Donors of the present example contain a conditional origin of replication that depends on a pir$^+$ (pir positive) background now allows for selecting out from this reaction mix all desired Acceptor-Donor(s) combinations. For this, the reaction mix is used to transform to pir negative strains (TOP10, DH5α, HB101 or other common laboratory cloning strains). Then, Donor vectors will act as suicide vectors when plated out on agar containing the antibiotic corresponding to the Donor encoded resistance marker, unless fused with an Acceptor. By using agar with the appropriate combinations of antibiotics, all desired Acceptor-Donor fusions can be selected for.

In this way, fusion vectors of 25 kb and larger can be generated. In stability tests (serial passaging for more than 60 generations), even such large plasmids are stable as checked by restriction mapping, even if only one of the antibiotics corresponding to the encoded resistance markers was provided in the growth medium.

C.2.1. Cre-LoxP Fusion of Acceptors and Donors

The following protocol is designed for generating multigene fusions from Donors and Acceptors by Cre-LoxP reaction.

Reagents:
Cre recombinase
Standard E. coli competent cells (pir$^-$ strain)
Antibiotics
96 well microtiter plates
12 well tissue-culture plates (or petri dishes) w. agar/antibiotics
LB media 1. For a 20 µl Cre reaction, mix 1~2 µg of each educts in approximate equal amounts (5' DNA termini). Add ddH$_2$O to adjust the total volume to 16~17 µl, then add 2 µl 10×Cre buffer and 1-2 µl Cre recombinase.
2. Incubate the Cre reaction at 37° C. (or 30° C.) for 1 hour.
3. Optional: load 2-5 µl Cre reaction on an analytical agarose gel for examination. Heat inactivation at 70° C. for 10 minutes before the gel loading is strongly recommended.
4. For chemical transformation, mix 10-15 µl Cre reaction with 200 µl chemical competent cells. Incubate the mixture on ice for 15-30 minutes. Then perform heat shock at 42° C. for 45-60 s.
   Up to 20 µl Cre reaction (0.1 volumes of the chemical competent cell suspension) can be directly transformed into 200 µl chemical competent cells.
   For electrotransformation, up to 2 µl Cre reaction could be directly mixed with 100 µl electrocompetent cells, and transformed by using an electroporator (e.g. BIORAD E. coli Pulser) at 1.8-2.0 kV.
   Larger volumes of Cre reactions should be desalted by ethanol precipitation or PCR purification column before electrotransformation. The desalted Cre reaction mix does preferably not exceed 0.1 volumes of the electrocompetent cell suspension.
   The cell/DNA mixture could be immediately used for electrotransformation without prolonged incubation on ice.
5. Add up to 400 µl of LB media (or SOC media) per 100 µl of cell/DNA suspension immediately after the transformation (heat shock or electroporation).
6. Incubate the suspension in a 37° C. shaking incubator overnight or for at least 4 hours.
   For recovering multifusion plasmid containing more than 2 resistance markers, it is strongly recommended to incubate the suspension at 37° C. overnight.
7. Plate out the recovered cell suspension on agar containing desired combination of antibiotics. Incubate at 37° C. overnight.
8. Emerged colonies after overnight incubation might be verified directly by restriction digestion at this stage, by referring to steps 12-16, supra. Especially in the case that only one multifusion plasmid is desired.
   For further selection by single antibiotic challenges on a 96 well microtiter plate, continue to step 9.
   Several various multifusion plasmids can be processed and selected on one 96 well microtiter plate in parallel.
9. For 96 well antibiotic tests, inoculate four colonies from each antibiotic agar plate into ~500 µl LB media without antibiotics. Incubate the cell cultures in a 37° C. shaking incubator for 1-2 hours.
10. During the incubation of colonies, fill a 96 well microtiter plate with 150 µl antibiotic-containing LB media or colourful dye (positional marker) in corresponding wells.
    A typical arrangement of the solutions, which is used for parallel selections of multifusion plasmids, is shown in FIG. 7. The basic principle underlying this aspect of the present invention is that every cell suspension from single colonies needs to be challenged by all four single antibiotics.
11. Add 1 µl aliquots of pre-incubated cell cultures to the corresponding wells. Then incubate the inoculated 96 well microtiter plate in a 37° C. shaking incubator overnight at 180-200 rpm.
    It is recommendable to use parafilm to wrap the plate.
    The rest pre-incubated cell cultures could be kept in 4° C. fridge for further inoculations.
12. Select transformants containing desired multifusion plasmids according to the combination of dense and clear cell cultures from each colony. Inoculate 10-20 µl cell cultures into 10 ml LB media with corresponding antibiotics. Incubate in a 37° C. shaking incubator overnight.
13. Centrifuge the overnight cell cultures at 4000 g for 5-10 minutes. Purify cell pellets with plasmid miniprep kit according to manufacturers' information.
14. Determine the concentrations of purified plasmid solutions by using UV absorption (e.g. NanoDrop™ 1000).
15. Digest 0.5~1 µg of the purified plasmid solution in a 20 µl restriction digestion (with 5-10 unit endonuclease). Incubate under recommended reaction condition for ~2 hours.
16. Use 5-10 µl of the digestion for analytical agarose gel (0.8-1.2%) electrophoresis. Verify the plasmid integrity by comparing the actual restriction pattern to the predicted restriction pattern in silico (e.g. by using VectorNTI).

C.2.2. Deconstruction of Fusion Vectors by Cre

The following protocol can be used, for instance for the recovery of four single ACEMBL vectors (pACE, pDC, pDK, pDS) by deconstructing tetra-fused pACKS plasmid (pACE-pDC-pDK-pDS) which preferably forms part of the ACEMBL System kit (see below Section E of the present embodiment). Likewise, the protocol is suitable for releasing single educts from multifusion constructs. This is achieved by Cre-LoxP reaction, transformation and plating on agar with appropriately reduced antibiotic resistance level (FIG. 6). For the liberated educt, encoding genes can be modified and diversified. Then, the diversified construct is resupplied by Cre-LoxP reaction.

Reagents:
Cre recombinase (and 10× Buffer)
E. coli competent cells
(pir$^+$ strains, pir$^-$ strains could be used only when partially deconstructed Acceptor-Donor fusions are desired).
Antibiotics 1. For a 20 μl De-Cre reaction, Incubate ~1 μg multifusion plasmid with 2 μl 10×Cre buffer, 1~2 μl Cre recombinase, add ddH$_2$O to adjust the total reaction volume to 20 μl.
2. Incubate the De-Cre reaction at 30° C. for 1-4 hour.
3. Optional: load 2-5 μl De-Cre reaction on an analytical agarose gel for examination.
   Heat inactivation at 70° C. for 10 minutes before the gel loading is recommended.
4. For chemical transformation, mix 10-15 μl De-Cre reaction with 200 μl chemical competent cells. Incubate the mixture on ice for 15-30 minutes. Then perform heat shock at 42° C. for 45-60 s.
   Up to 20 μl De-Cre reaction (0.1 volumes of the chemical competent cell suspension) can be directly transformed into 200 μl chemical competent cells.
   For electrotransformation, up to 2 μl De-Cre reaction could be directly mixed with 100 μl electrocompetent cells, and transformed by using an electroporator (e.g. BIO-RAD E. coli Pulser) at 1.8-2.0 kV.
   Larger volumes of De-Cre reaction should be desalted by ethanol precipitation or PCR purification column before electrotransformation. The desalted De-Cre reaction mix does preferably not exceed 0.1 volumes of the electrocompetent cell suspension.
   The cell/DNA mixture could be immediately used for electrotransformation without prolonged incubation on ice.
5. Add up to 400 μl of LB media (or SOC media) per 100 μl of cell/DNA suspension immediately after the transformation (heat shock or electroporation).
6. Incubate the suspension in a 37° C. shaking incubator.
   For recovery of partially deconstructed double/triple fusions, incubate the suspension in a 37° C. shaking incubator overnight or for at least 4 hours.
   For recovery of individual educts such as single ACEMBL vectors from pACKS plasmid, incubate the suspension in a 37° C. incubator for 1-2 hours.
7. Plate out the recovered cell suspension on agar containing desired combination of antibiotics. Incubate at 37° C. overnight.
8. Colonies after overnight incubation can be verified directly by restriction digestion at this stage, by referring to steps 12-16.
   This is especially recommended if only one single educt or partially deconstructed multifusion plasmid is desired.
   For further selection by single antibiotic challenges on a 96 well microtiter plate, continue to step 9.
   Several various single educts/partially deconstructed multifusion plasmids can be processed and selected on one 96 well microtiter plate in parallel.
9. For 96 well antibiotic tests, inoculate four colonies from each antibiotic agar plate into ~500 μl LB media without antibiotics. Incubate the cell cultures in a 37° C. shaking incubator for 1-2 hours.
10. During the incubation of colonies, fill a 96 well microtiter plate with 150 μl antibiotic-containing LB media or colourful dye (positional marker) in corresponding wells.
    Referring to FIG. 7 it is possible to provide a similar arrangement of the solutions, which is used for parallel selections of four various single educts/partially deconstructed multifusion plasmids. The underlying principle of the present aspect of the invention is that every cell suspension from single colonies is to be challenged by all four antibiotics separately.
11. Add 1 μl aliquots of pre-incubated cell cultures to the corresponding wells. Then incubate the inoculated 96 well microtiter plate in a 37° C. shaking incubator overnight at 180-200 rpm.
    It is recommendable to use parafilm to wrap the plate.
    The remaining pre-incubated cell cultures could be kept in 4° C. fridge for further inoculations.
12. Select transformants containing desired single educts/partially deconstructed multifusion plasmids according to the combination of dense and clear cell cultures from each colony. Inoculate 10-20 μl cell cultures into 10 ml LB media with corresponding antibiotic(s). Incubate in a 37° C. shaking incubator overnight.
13. Centrifuge the overnight cell cultures at 4000 g for 5-10 minutes. Purify cell pellets with plasmid miniprep kit according to manufacturers' information.
14. Determine the concentrations of purified plasmid solutions by using UV absorption (e.g. NanoDrop™ 1000).
15. Digest 0.5-1 μg of the purified plasmid solution in a 20 μl restriction digestion (with 5-10 unit endonuclease). Incubate under recommended reaction condition for ~2 hours.
16. Use 5-10 μl of the digestion for analytical agarose gel (0.8-1.2%) electrophoresis. Verify the plasmid integrity by comparing the actual restriction pattern to predicted restriction pattern in silico (e.g. by using VectorNTI).
17. Optional: during recovery of all four single ACEMBL vectors from pACKS plasmid, in case one or more single ACEMBL vectors fail to be liberated from one De-Cre reaction. One can just pick partially deconstructed double/triple fusions containing desired single ACEMBL vector(s), and perform a second De-Cre reaction (repeat steps 1-8).
    Typically, up to 2 sequential De-Cre reactions are sufficient to recover all four single ACEMBL vectors from pACKS plasmid, and the liberation of single educts from double/triple fusions could be much more efficient than from pACKS plasmid (quadruple fusion). The same principle also applies to the deconstruction of any other multifusion plasmid based on the ACEMBL system according to the present invention.

C.3. Coexpression in Bacteria by Cotransformation

Protein complexes can be expressed also from two separate vectors that were cotransformed in expression strains. The cotransformed vectors can have the same or different origins of replication, however, they must encode for different resistance markers. Plasmids pACE (ampicillin resistance marker) and pACE2 (tetracycline resistance marker) have both a ColE1 derived replicon and can therefore be used with all common expression strains. pACE and pACE2 derivatives (also including fused Donors if needed) can be cotransformed into expression strains, and double transformants selected for by plating on agar plates containing both ampicillin and tetracycline antibiotics.

Transformations are carried out using standard transformation protocols (see, e.g. the latest edition of Ausubel et al. (ed.), supra.

D. Automation

As already outlined above, cloning and expression of multiple protein complexes using the nucleic acids, vectors and methods of the present invention is highly suited for automation equipment employing current robotic techniques.

In the following general protocols as exemplified for a Tecan Freedom EvoII 200 pipetting device are provided. The pipeting device is typically equipped with liquid handling arm1 (LiHa1), 4 fixed tips (steel needles), 4 disposable tips coni (Diti's), 250 µl syringes, liquid handling arm2 (LiHa2), 8 fixed tips (steel needles), 2.5 ml syringes, robotic manipulator arm (RoMa/transportation of plates), version long. The work station usually contains the following integrated devices: thermocycler PTC-200 (Biorad), Te-Shake, heatable plate shaker (Tecan), Variomag Thermoshaker, heat- and coolable plate shaker (Inheco), Te-Vacs, dual vacuum station for filter plates (Tecan), Safirell, UV VIS plate reader (Tecan) and cooling unit 400W (FRYKA multistar).

D.1. Automated SLIC Process

A schematic representation of a workflow for automated SLIC is shown in FIG. 22.

Step 1: Initial PCR

Source plate: 96 well standard microtiter plate containing the PCR templates (cDNA approx. 0.2 µg/µl)

Reaction plate: 96 well PCR plate (Eppendorf)

Material: Sample mix plate (96 well PCR plate; Eppendorf), 1% agarose E-Gel® (Invitrogen), Phusion® DNA Polymerase master mix, oligonucleotide primers at 20 µM, 2×DNA loading dye (2×DLD) (Fermentas), E-Gel® Low Range quantitative DNA Ladder (Invitrogen), 10× Buffer Tango® with BSA (Fermentas), DpnI (Fermentas)

PCR Program:
    11×[98° C. for 20 sec.→60-50° C. for 30 sec. (step down every 2$^{nd}$ cycle 1° C.)→72° C. for 3 min.]
    19×[98° C. for 20 sec.→50° C. for 30 sec.→72° C. for 3 min.]
    72° C. for 3 min.
    Hold at 10° C.

DpnI Digest Program:
    37° C. for 3 h
    10° C. for 1 min

Procedure:
    Wash tips→Pipet 89 µl PCR master-mix into reaction plate
    Wash tips→Pipet 1 µl template DNA according to worklist
    Wash tips→Pipet 5 µl primer each to reaction plate
    Wash tips→Run PCR program
    Wash tips→Pipet 10 µl 10× Buffer Tango® with BSA to reaction plate
    Wash tips→Pipet 5 µl DpnI to reaction plate
    Wash tips→Run DpnI digest program
    Wash tips→Pipet 10 µl 2×DLD to each well of sample mix plate
    Wash tips→Pipet 15 µl DNA marker each to the E-gel marker slots
    Wash tips→Pipet 10 µl PCR product to 2×DLD on sample mix plate
    Wash tips→Pipet 15 µl sample mix to the E-Gel sample slots
    Wash tips→Run E-Gel® for 25 min.
    Assess results Step 2: PCR Purification Source plate: 96 well PCR plate (Eppendorf) with PCR samples Target plate: 96 well microtiter elution plate (Macherey-Nagel)

Material: PCR purification kit, NucleoSpin 96 Extract II Kit (Macherey-Nagel)

Procedure: According to manufacturer's information (http://www.macherey-nagel.com/tabid/10887/default.aspx)

Step 3: T4 DNA Polymerase Reaction

Source plate: 96 well microtiter elution plate (Macherey-Nagel)

Reaction plate: 96 well PCR plate (Eppendorf)

Material: bidest. water, 10×T4 DNA polymerase reaction buffer (Novagen), 100 mM DTT, 2M Urea, T4 DNA polymerase (Novagen LIC qualified), 500 mM EDTA Incubation program: 23° C. for 10 min. (program 1)
    75° C. for 20 min. (program 2)

Procedure:
    Wash tips→Pipet 6 µl water in to reaction plate
    Wash tips→Pipet 2 µl 10× reaction buffer into reaction plate
    Wash tips→Pipet 1 µl 100 mM DTT into reaction plate
    Wash tips→Pipet 2 µl 2M Urea into reaction plate
    Wash tips→Pipet 8 µl DNA sample from prey. PCR into reaction plate
    Wash tips→Pipet 0.5 µl T4 DNA polymerase into reaction plate
    Wash tips→Run incubation program 1
    Wash tips→Pipet 1 µl 500 mM EDTA into reaction plate
    Wash tips→Run incubation program 2

Step 4: Annealing

Source plate: Reaction plate from T4 DNA polymerase reaction

Reaction plate: 96 well PCR plate (Eppendorf)

Material: bidest. water, 10×DNA Ligase Reaction Buffer (NEB), linearised vector

Incubation program: 65° C. for 8 min.→ramp down 0.4° C./min. to 35° C.→10° C. for 1 min.

Procedure:
    Wash tips→Pipet 150 ng T4 DNA polymerase treated insert DNA according to worklist into reaction plate
    Wash tips→Pipet 150 ng linearised vector DNA according to worklist into reaction plate
    Wash tips→Run incubation program Step 5: Transformation in *E. coli*

Source plate: Reaction plate from the annealing step

Reaction plate: 96 well PCR plate (Eppendorf)

Culture plate: 2 ml 96 well plate (Nunc)

Target plates: 12 well cell culture plates containing 2 ml of LB-agar with appropriate antibiotics (standard concentrations used: Ampicillin 100 µg/ml, Kanamycin 50 µg/ml, Spectinomycin 50 µg/ml, Chloramphenicol 30 µg/ml)

Material: *E. coli* cells (XI1 blue) that are chemically competent for transformation, SOC-medium Transformation program: Heat thermocycler to 42° C.
    Incubate at 42° C. for 30 sec.
    Transfer immediately to cooled (0° C.) pipetting carrier Procedure:
    Wash tips→Pipet 100 µl competent *E. coli* cells into reaction plate
    Wash tips→Pipet 10 µl DNA sample from annealing step into reaction plate
    Wash tips→Incubate at 0° C. for 30 min.
    Run transformation program
    Incubate at 0° C. for 5 min.

Wash tips→Pipet 250 µl SOC-medium into culture plate
Wash tips→Transfer transformation mix into culture plate
Incubate at 37° C. and 720 rpm. (Te-Shake Shaker) for 2 h
Wash tips→Pipet 50 µl culture into target plate (agar plate)
Wash tips→Shake target plate at 12 Hz for 1 min. (plating out)
Incubate target plates over night at 37° C.

Step 6: Picking Clones and Setting Up Over Night Cultures (Manual Step)
Source plate: 12 well cell culture plates containing E. coli colonies
Target plate: 24 well culture plate
Material: 2×TY culture medium, incubator which carries culture plates
Procedure: Pick 4 colonies per reaction and transfer to 3 ml 2×TY medium in a 24 well culture plate. Incubate at 37° C. and approx. 220 rpm over night.

Step 7: Plasmid Extraction (Miniprep)
Source plate: 24 well culture plate (usually 3 ml culture)
Target plate: 96 well microtiter elution plate (Macherey-Nagel)
Material: Plasmid extraction kit, NucleoSpin Robot 96 Plasmid Kit (Macherey-Nagel)
Procedure: According to manufacturer (see http://www.machereynagel.com/tabid/10885/default.aspx)

Step 8: Assessment
Plasmid yield is quantified by measuring UV absorbance with a Thermo Scientific NanoDrop™ 1000 Spectrophotometer according to manufacturer. Plasmid integrity was assessed by E-gel (Invitrogen)

The efficacy of the SLIC protocol is assessed in manual and robotics mode. The results of the comparison are shown in Table II. Results are based on a set of 25 different Donor/Acceptor constructions prepared.

TABLE II

Comparison Manual versus Robotic SLIC procedure (based on 25 constructs each)

|  | Manual | Evoll |
|---|---|---|
| DNA used for T4 reaction: | 200-400 ng insert<br>200-400 ng vector | 400-800 ng insert<br>400-800 ng vector |
| T4 reaction volume for transformation: | 5 µl: 2.5 µl (insert)<br>+2.5 µl (vector) | 5ul: 2.5 µl (insert)<br>+2.5 µl (vector) |
| Volume comp. cells (XI1Blue, chem. comp): | 100 µl (+300 µl SOC) | 100 µl (+300 µl SOC) |
| Volume plated | 200 µl (Petri dish) | 50 µl/well (12 well plate)<br>200 µl (petri dish) |
| Clones obtained: | 200->2000 (Petri dish) | 25-250 (12 well plate)<br>70-5300 (petri dish) |

D.2 Automated Cre Fusion Process

A schematic representation of a workflow for automated Cre fusion is shown in FIG. 23.

Step 1: Cre-LoxP Plasmid Fusion Reaction
Source plate: 96 well microtiter elution plate from the plasmid extraction process containing plasmids suitable for Cre-Lox fusion
Reaction plate: 96 well PCR plate (Eppendorf)
Material: bidest. water, 10×Cre reaction buffer (NEB), Cre recombinase (NEB)
Incubation program: 37° C. for 1 h→10° C. for 1 min.
Procedure:
Wash tips→Pipet 6 µl bidest. water into reaction plate
Wash tips→Pipet 2 µl 10×cre reaction buffer into reaction plate
Wash tips→Pipet plasmid DNA suitable for Cre recombination according to worklist into reaction plate
Wash tips→Pipet 2 µl Cre recombinase into reaction plate
Wash tips→Run incubation program
Total reaction volume: 20 µl Step 2, 3 and 4: Transformation in E. coli and Plasmid Extraction:
Identical to the method described in above Section D.1., with the exception that reaction plate from Cre recombination step is used as source plate and recovery time in SOC-medium is prolonged to a total of 4 h. Chemically competent Mach1 cells are used for transformation. For Cre reaction with 3 and 4 vectors agar-plates with half of the antibiotic concentration (standard concentrations used: Ampicillin 100 µg/ml, Kanamycin 50 µg/ml, Spectinomycin 50 µg/ml, Chloramphenicol 30 g/ml) are used.

Step 5: Assessment
Plasmid fusion yield is quantified by measuring UV absorbance with a Thermo Scientific NanoDrop™ 1000 Spectrophotometer according to the manufacturer's instructions. Plasmid integrity is assessed by E-gel (Invitrogen) of undigested and digested samples. Suitable restriction sites that yield a digestion pattern characteristic for the respective fusions are identified by using Vector NTI (Invitrogen) and used for restriction mapping.

The efficacy of the Cre reaction is tested by performing a series of fusion reactions, each in triplicate, by using the Evoll liquid handling workstation. The results are summarized in Table III.

TABLE III

Efficiency of Cre-LoxP Reactions on Evoll (assessed in triplicate for each reaction)

| | |
|---|---|
| Volume Cre-reaction used for transformation (all reactions): | 10 µl |
| Volume chem. comp. cells (XI1Blue, Mach1) per transformation (all reactions): | 100 µl (+300 µl SOC) |
| Volume transformation reaction plated: | 50 µl/well (12 well plate)<br>200 µl (petri dish) |
| Clones obtained:<br>(a) Double vector fusion reaction (AD, one Acceptor, one Donor)<br>    >1000 fused functional AD plasmids<br>    plated on a standard petri dish containing the respective two antibiotics<br>(b) Triple vector fusion reaction (ADD, one Acceptor, two Donors)<br>    12-80 fused functional ADD plasmids<br>    plated on a standard petri dish containing the respective three antibiotics<br>(c) Quadruple vector fusion reaction (ADDD, one Acceptor, three Donors)<br>    For quadruple vector fusions (ADDD, one Acceptor and three Donors), two possibilities exist.<br>    (1) Single reaction ADDD (four vector Cre-Lox fusion, low efficiency)<br>    (2) Two step reaction ADD + D: Triple fusion as in (b), then addition of a further Donor.<br>Option 2 (ADD + D) is preferred for routine robot use as it represents a more robust approach, resulting in example experiments in 20-100 fused functional ADDD plasmids when plated on a standard petri dish containing all four antibiotics. | |

D.3. High-Throughput Micro Batch I.MAC
Source plate: 2 ml deepwell plate (Eppendorf)
Filter plate: Glas filter plate (Novagen)
Target plate: standard microtiter plate (Greiner)
Material: Ni-NTA bulk beads 50% in 20% ethanol (GeHealthcare), freezer at −20° C., tabletop centrifuge suitable for microtiter plates, sonication device with microtip, IMAC binding and elution buffer suitable for the specific protein (Berrow et al., Acta Cryst. (2006). D62, 1218-1226).

Procedure:
Sample Preparation (Off Line)
  Harvest *E. coli* cells expressing the desired protein by centrifugation at 3000 g (4° C.) directly in the source plate
  Freeze cell pellets for 30 min. at −20° C.
  Thaw cell pellets 15 min. at room temperature
Preparation of the Filter Plate
  Wash tips→Resuspend Ni-NTA bead suspension by pipetting up and down
  20 times 200 μl→Transfer 200 μl bead suspension to filter plate
  Wash tips→Apply vacuum 550 mbar for 30 sec. (remove 20% ethanol)
  Wash tips→Pipet 1 ml equilibration buffer (e.g. binding buffer) to resin
  Wash tips→Apply vacuum 300 mbar for 60 sec. (equilibration)
IMAC Purification, Preparation
  Wash tips→Pipet 1 ml binding buffer to the samples in the source plate
  Wash tips→Resuspend cell pellets by pipetting up and down 10 times 750 μl
  Wash tips
Sonication of Samples (Off Line)
  Sonication of the samples to insure complete lysis of the cells
IMAC Purification, Loading and Elution
  Wash tips→Transfer whole lysate to filter plate
  Wash tips→Apply vacuum 300 mbar for 90 sec. (binding step)
  Wash tips→Pipet 1 ml wash buffer to the samples
  Wash tips→Apply vacuum 300 mbar for 90 sec. (wash step)
  Repeat wash step 3 times
  Wash tips→Pipet 100 μl elution buffer to the samples
  Wash tips→Incubate 3 min. at room temperature
  Apply vacuum 650 mbar for 90 sec. (elution step)
Assessment
  Eluted samples (10 μl-12 μl) are loaded manually on 12% denaturing gels using a Biorad Minigel System, pre-run at 135 V for 25 min, and then run for 65-70 min. at 185V. Gels arre stained with Coomassie Brilliant Blue according to standard procedures.

E. ACEMBL Kit for Expression of Proteins in Prokaryotic Hosts

A kit according to a preferred embodiment for expression in prokaryotic hosts contains:
  BW23473, BW23474 cells[1] and/or Cre recombinase
  pACKS quadruple fusion vector[2]
  made of pACE (Acceptor), and pDC, pDK, pDS (Donors)
  pACE2 vector
  pACE-[VHLbc/BFP/mGFP] control plasmid
  triple fusion vector made of pACE-VHLbc, pDK-BFP, pDS-mGFP[3]

[1] *E. coli* strains expressing the pir gene for propagation of Donor derivatives (any other strain with pir+ background can be used).
  [2] This fusion vector was created by Cre-LoxP reaction of pACE, pDC, pDK and pDS. It is resistant to ampicillin, kanamycin, chloramphenicol and spectinomycin. Individual ACEMBL vectors can be liberated from this quadruple fusion by Cre-LoxP mediated deconstruction as described above in protocol C.2.2. Sequences for single ACEMBL vectors according to the present embodiment and pACKS quadruple fusion are provided in SEQ ID NO: 2 to 7.
  [3] pDS-mGFP contains a coiled-coil fused to the N-terminus of eGFP (see Berger et al. (2003) *Proc. Natl. Acad. Sci. USA* 100, 12177-82.

Optional Components:
  Antibiotics: ampicillin, chloramphenicol, kanamycin, spectinomycin, tetracycline Enzymes:
  T4 DNA polymerase (for recombination insertion of genes)
  Phusion polymerase (for PCR amplification of DNA)
  Restriction enzymes and T4 DNA ligase (for conventional cloning, if desired)

The present invention is further illustrated by the following non-limiting examples.

EXAMPLES

Examples of multiprotein expressions by using the above-described ACEMBL system are shown in the following illustrating the gene combination procedures outlined above. Reactions presented were either carried out manually following the protocols provided in above Section C. or on a Tecan Freedom EvoII 200 robot with adapted protocols according above Section D.

Example 1

SLIC Cloning into ACEMBL Vectors: Human TFIIF

Genes coding for full-length human RAP74 with a C-terminal oligo-histidine tag and full-length human RAP30 were amplified from pET-based plasmid template (Gaiser et al. (2000) *J. Mol. Biol.* 302, 1119-1127) by using the primer pair T7InsFor (5'-TCCCGCGAAATTAATACGACTCACTAT-AGGG-3'; SEQ ID NO: 20) and T7Insrev (5'-CCTCAAGAC-CCGTTTAGAGGCCCCAAGGGGTTATGCTAG-3'; SEQ ID NO: 21) following the protocols described above. Linearized vector backbones were generated by PCR amplification from pACE and pDC by using primer pair T7VecFor (5'CTAGCATAACCCCTTGGGGC-CTCTAAACGGGTCTTGAGG-3'; SEQ ID NO: 22) and T7VecRev (5'-CCCTATAGTGAGTCGTAT-TAATTTCGCGGGA-3'; SEQ ID NO: 23) in both cases. Above Protocol 1 (Section C) was followed, resulting in pACE-RAP30 and pDC-RAP74his (FIG. 8). These plasmids were fused by Cre-LoxP reaction (see above Section C). Results from restriction mapping by BstZ17I/BamHI double digestion of 11 double resistant (Cm, Ap) colonies is shown by a gel section from 1% E-gel electrophoresis (M: NEB 1 kb DNA marker) in FIG. 8. All clones tested showed the expected pattern (5.0+2.8 kb). One clone was transformed in BI21(DE3) cells. Expression and purification by $Ni^{2+}$-capture and S200 chromatography resulted in human TFIIF complex (FIG. 21A).

The high-level soluble expression of full-length human TFIIF (FIG. 21A) is noteworthy, as individual expression of the subunits invariably leads to insoluble material. In the past, crystal structure analysis of human TFIIF dimerization domain had necessitated many iterative cycles of limited proteolysis, recloning, insoluble expression of the designed fragments and co-refolding (Gaiser et al. (2000), supra). Similar laborious situations are commonplace in prior art protein complex research. It is conceivable that the large investment of labor involved can now be significantly reduced using the nucleic acids and vectors of the present invention, in particular the ACEMBL system.

Example 2

Polycistron Insertion by SLIC: Human VHL/Elongin b/Elongin c Complex

The gene encoding for Von Hippel Lindau protein (amino acids 54-213), fused at its N-terminus to a six-histidinethioredoxin fusion tag, was PCR amplified from plasmid pET3-HisTrxVHL by using primers T7InsFor (see above Table I) and SmaBamVHL (5'-GAATTCACTGGC-CGTCGTTTTACAGGATCCTTAATCTC-CCATCCGTTGATG TGCAATG-3'; SEQ ID NO: 45). SmaBamVHL primer is a derivative of the SmaBam adaptor sequence (Table I; SEQ ID NO: 17) elongated at its 3' by the insert specific sequence at the 3' end of the VHL gene (including a stop codon). The gene encoding for full-length elongin b was PCR amplified from pET3-ElonginB by using primers BamSmaEB (5'-GGATCCTGTAAAACGACGGCCAGT-GAATTCG CTAGCTCTAGAAATAATTTTGTTTAAC-3'; SEQ ID NO: 46) and SacHindEB (5'-GAGCTCGACTGG-GAAAACCCTGGCGAAGCTTAGATCTG-GATCCTTACTGCACG GCTTGTTCATTGG-3'; SEQ ID NO: 47), which are derivatives of the corresponding adaptors (Table I). The gene for elongin c (amino acids 17-112) was amplified from pET3-ElonginC by using primers HindSacEC (5'-AAGCTTCGCCAGGGTTTTCCCA GTCGAGCTC-CAATTGGAATTCGCTAGCTCTAG-3'; SEQ ID NO: 48) and BspEco5EC (5'-GATCCGGA TGTGAAATTGTTATC-CGCTGGTACCAAGCTTAGAT CTGGATCCTTAA-CAATCTAAGAAG-3'; SEQ ID NO: 49), which are derivatives of the corresponding adaptors (Table I). Vector backbone was PCR amplified by using primers Tn7VecRev and Eco5Bsp, and pACE as a template (FIG. 9). Multifragment SLIC was carried out according to above Protocol 2 (Section C) resulting in pACE-VHLbc which contains a tricistron. Clones were plated on agar plates containing ampicillin. A positive clone, verified by sequencing, was used in the coexpression experiment described below (Example 5).

Example 3

The Homing Endonuclease/BstXI module: Yeast RES Complex

Plasmids pCDFDuet-Pml1p, pRSFDuet-Snu17p-NHis and pETDuet-Bud13p, coding for yeast proteins (all full-length) Pml1p, Snu17p and Bud13p, respectively, were provided by Dr. Simon Trowitzsch and Dr. Markus Wahl (Max-Planck-Institute for Biophysical Chemistry, Göttingen, Germany). Snu17p contains a six-histidine tag fused to its N-terminus. The gene encoding for His6-tagged Snu17p was excised from pRSFDuet-Snu17p-NHis by using restriction enzymes NcoI and XhoI, and ligated into a NcoI/XhoI digested pACE construct (containing an unrelated gene between NcoI and XhoI sites) resulting in pACE-Snu17. The gene encoding for Bud13p was liberated from pETDuet-Bud13p by restriction digestion with XbaI and EcoRV, and placed into XbaI/PmeI digested pDC resulting in pDC-Bud13. The gene encoding for Pml1p was liberated from pCDFDuet-Pml1p by restriction digestion with NdeI and XhoI, and placed into NdeI/XhoI digested pDC resulting in pDC-Pml1. Next, the expression cassette for Bud13p was liberated from pDC-Bud13 by digestion with PI-SceI and BstXI. The liberated fragment was inserted into PI-SceI digested and alkaline phosphatase treated pDC-Pml1p resulting in pDC-Bud13p-Pml1p.

pACE-Snu17 and pDC-BudPml were fused by Cre-LoxP reaction and selected for by plating on agar plates containing ampicillin and chloramphenicol. Fusion plasmids were transformed into BI21(DE3) cells. Expression and purification by Ni$^{2+}$-capture and S200 size exclusion chromatography resulted in the trimeric RES complex.

The strategy for cloning the yeast RES complex according to the method of the present invention is schematically illustrated in FIG. 10.

Example 4

Coexpression by Cotransformation: Human NYB/NYC

Genes encoding for protein NYB (amino acids 49-141) and NYC (amino acids 27-12) were excised from vectors pACYC18411-NYB and pET15-NYC, respectively (Romier et al. (2003 J. Biol. Chem. 278, 1336-1345). NdeI and BamHI where used for NFYB. XbaI and BamHI where used for NYC, thus importing a six-histidine tag at the N-terminus of the protein. The NYB insert was ligated into pACE digested with NdeI and BamHI. The NYC insert was ligated into pACE2 digested by XbaI and BamHI. pACE-NFYB and pACE2-NFYC were transformed into BL21(DE3) cells containing the pLysS plasmid. Selection on agar plates containing ampicillin, tetracycline and chloramphenicol resulted in triple resistant colonies. The complex was expressed and purified by Ni2+ capture (IMAC) and S75HR (Pharmacia) size exclusion chromatography.

Example 5

Coexpression from Acceptor-Donor Fusions

Six heterologous genes coding for a trimeric protein complex (VHLbc: VonHippel-Lindau protein amino acids 54-213/full-length elonginB/elonginC amino acids 17-112) (Stebbins et al. (1999) Science 284, 455-61), a gene encoding for the AAA ATPase FtsH (amino acids 147-610), and two genes encoding for fluorescent markers (BFP and GFP) were assembled as illustrated in FIG. 20. In a single Cre reaction, all combinations of one Acceptor (pACE-VHLbc) and three Donors (pDC-FtsH, pDK-BFP, pDS-mGFP) were obtained and selected, including a quadruple fusion containing all six heterologous genes; see FIG. 20). Clones were verified by 96 well microtiter assay as described above for the ACEMBL system, Section C. Expression and Ni$^{2+}$ affinity capture, combined with immunostaining of the untagged fluorescent markers, confirmed successful multiprotein expression (FIGS. 16 and 17B). Proteins were expressed overnight in BL21(DE3) cells in 24 well deep-well plates in small scale using autoinduction media (Studier (2005) Protein Expr. Purif. 41, 207-34). Restriction mapping revealed that even large fusion plasmids were stable over many (more than 60) generations, even if challenged by a single antibiotic in the medium only.

Example 6

Expression of the YidC-SecYEGDF Holotranslocon

As illustrated in FIG. 21C, the ACEMBL system was used to produce a large multiprotein complex, the YidC-SecYEGDF holotranslocon that contains in total 33 transmembrane helices. This machinery is used to transport unfolded polypeptides into the cell membrane or for translocation into the periplasm of bacteria (Duong et al. (1997) EMBO J. 16, 2757-68.

Example 7

Expression of Human IKK Complex in Insect Cells

Following the protocols for single gene insertion into ACEMBL vectors as outlined above in Section C.1., the genes for IKK1 (also called IKKalpha), IKK2 (also called IKKbeta) and IKK3 (also called Nemo) were cloned into pACEBac1, pIDC and pIDS respectively (maps of the resulting plasmids pACEBac1-HisIKK1, pIDC-CSIKK2 and pIDS-IKK3 are shown in FIGS. 46, 47 and 48, respectively). IKK1-2 double fusion (pACEBac1-HisIKK1 with pIDC-CSIKK2) and IKK1-2-3 triple fusions (all three vectors) were created by Cre-LoxP fusions as outlined above in Section C.2. The fusions were introduced into suitable host cells carrying a baculovirus genome (EMBac) as a bacterial artificial chromosome. The vector fusions were integrated into the baculoviral genome via Tn7 transposition. Productive integration was assessed by blue/white screening. DNA of composite virus was prepared from white clones and transfected into Sf21 cells.

Example 8

Expression of a H1N1-Influenza Virus-Like Particle

A virus-like particle (VLP) of the swine-flu virus (influenza virus of type H1N1) comprising the proteins HA, NA, M1 and M2 was expressed in insect cells (Sf21) by the following strategy: genes coding for HA and NA were cloned into pACEBac1 by single gene insertion as outlined above in Section C.1. The same procedure was followed for cloning the genes coding for M1 and M2 into pIDC. Double expression cassettes for HA-NA and M1-M2, respectively, were generated by using the HE-BstXI sites in the respective MIE (see above Section C.1.4.) resulting in plasmids pACEBac-HA-NA (plasmid map see FIG. 49) and pIDC-M1-M2 (plasmid map see FIG. 50). The vector for coding the complete H1N1-influenza-VLP was generated by CreLoxP fusion of pACEBac-HA-NA with pIDC-M1-M2 following the protocol in above Section C.2. The fusion vector was introduced into suitable host cells carrying a baculovirus genome (EMBac) as a bacterial artificial chromosome. The vector fusions were integrated into the baculoviral genome via Tn7 transposition. Productive integration was assessed by blue/white screening. DNA of composite virus was prepared from white clones and transfected into Sf21 cells.

The invention claimed is:

1. A nucleic acid containing at least one homing endonuclease (HE) site and at least one restriction enzyme (X) site wherein the HE and X sites are selected such that a ligation product having compatible cohesive ends results when the nucleic acid is cut by a homing endonuclease and a restriction enzyme, respectively, and the ligation product having compatible cohesive ends can neither be cleaved by the homing endonuclease nor the restriction enzyme, the nucleic acid comprising a nucleotide sequence selected from the group consisting of SEQ ID NO: 1, SEQ ID NO: 50, SEQ ID NO: 51, SEQ ID NO: 52 and SEQ ID NO: 53.

2. The nucleic acid of claim 1 having the sequence elements
HE-Prom-MCS-Term-X or HE-Prom-MCS-X
wherein
Prom: represents a promoter;
MCS: represent a multiple cloning site; and
Term: represents a terminator.

3. The nucleic acid of claim 2 wherein the MCS contains one or more homology regions.

4. The nucleic acid of claim 1 wherein the HE site is a recognition sequence that results in a 4 nucleotide overhang when cut by the homing endonuclease.

5. The nucleic acid of claim 1 wherein the HE site is a recognition sequence of a homing endonuclease selected from the group consisting of the group consisting of PI-SceI, I-CeuI, I-PpoI, I-HmuI I-CreI, I-DmoI, PI-PfuI, I-MsoI, PI-PspI, I-SceI, SegH, Hef, I-ApeII, I-AniI, Cytochrome b mRNA maturase bl3, PI-TliI, PI-TfuII and PI-ThyI.

6. The nucleic acid of claim 1 wherein the X site is a BstXI site.

7. The nucleic acid of claim 1 additionally comprising at least one site for integration of the nucleic acid into a vector or host cell.

8. A vector comprising a nucleic acid containing at least one homing endonuclease (HE) site and at least one restriction enzyme (X) site wherein the HE and X sites are selected such that a ligation product having compatible cohesive ends results when the nucleic acid is cut by a homing endonuclease and a restriction enzyme, respectively, and the ligation product having compatible cohesive ends can neither be cleaved by the homing endonuclease nor the restriction enzyme, the vector having a sequence element selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 and SEQ ID NO: 17.

9. The vector of claim 8 further containing at least one recognition sequence for a site-specific recombinase, preferably a loxP imperfect inverted repeat or a Tn7 attachment site.

10. The vector of claim 8 containing more than one of the sequence elements of the nucleic acid and containing more than one recognition sequence for a site-specific recombinase.

11. The vector of claim 10 further comprising a sequence of SEQ ID NO: 18.

12. The vector of claim 8 wherein the vector is a virus.

13. The vector of claim 12 wherein the virus comprises a baculovirus.

14. A method for producing a vector containing multiple expression cassettes comprising the steps of:
(a) providing a first vector comprising a nucleic acid containing at least one homing endonuclease (HE) site and at least one restriction enzyme (X) site wherein the HE and X sites are selected such that a first ligation product having compatible cohesive ends results when the first vector is cut by a homing endonuclease and a restriction enzyme, respectively, and the first ligation product having compatible cohesive ends can neither be cleaved by the homing endonuclease nor the restriction enzyme;
(b) inserting one or more genes between the HE site and the X site of the first vector;
(c) providing a second vector comprising a second nucleic acid containing at least one homing endonuclease (HE) site and at least one restriction enzyme (X) site wherein the HE and X sites are selected such that a second ligation product having compatible cohesive ends results when the second vector is cut by a homing endonuclease and a restriction enzyme, respectively, and the second ligation product of HE and X cohesive ends can neither be cleaved by the homing endonuclease nor the restriction enzyme;

(d) inserting one or more genes between the HE site and the X site of the second vector;

(e) cleaving the first vector with the homing endonuclease specific for site HE and with the restriction enzyme specific for site X yielding a fragment containing the at least one gene flanked by the cleaved HE and X site;

(f) cleaving the second vector with the homing endonuclease specific for site HE;

(g) ligating the fragment obtained in step (e) into the cleaved second vector obtained in step (f); and optionally (h) repeating steps (a) to (g) with one or more vector(s) generating the vector containing multiple expression cassettes.

15. The method of claim 14, wherein the first or second nucleic acid has a sequence element comprising:
HE-Prom-MCS-Term-X or HE-Prom-MCS-X
wherein
Prom: represents a promoter;
MCS: represent a multiple cloning site; and
Term: represents a terminator.

16. The method of claim 15, wherein the MCS contains one or more homology regions.

17. The method of claim 14, wherein the HE site is a recognition sequence that results in a 4 nucleotide overhang when cut by the homing endonuclease.

18. The method of claim 14, wherein the HE site is a recognition sequence of a homing endonuclease selected from the group consisting of the group consisting of PI-SceI, I-CeuI, I-PpoI, I-HmuI I-CreI, I-DmoI, PI-PfuI, I-MsoI, PI-PspI, I-SceI, SegH, Hef, I-ApeII, I-AniI, Cytochrome b mRNA maturase bl3, PI-TliI, PI-TfuII and PI-ThyI.

19. The method of claim 14, wherein the X site is a BstXI site.

20. A method for producing multiprotein complexes comprising the steps of:

(i) producing a vector containing multiple expression cassettes by the method of claim 14;

(ii) introducing the vector obtained in step (i) into a host cell; and (iii) incubating the host cell under conditions allowing the simultaneous expression of the genes present in the vector.

* * * * *

```
                        SEQUENCE LISTING

<160> NUMBER OF SEQ ID NOS: 54

<210> SEQ ID NO 1
<211> LENGTH: 210
<212> TYPE: DNA
<213> ORGANISM: Artificial
<220> FEATURE:
<223> OTHER INFORMATION: Multiple integration element

<400> SEQUENCE: 1
gggaattgtg agcggataac aattcccctc tagaaataat tttgtttaac tttaagaagg    60
agatatacat atgaggcctc ggatcctgta aaacgacggc cagtgaattc cccgggaagc   120
ttcgccaggg ttttcccagt cgagctcgat atcggtacca gcggataaca atttcacatc   180
cggatcgcga acgcgtctcg agagatccgg                                    210

<210> SEQ ID NO 2
<211> LENGTH: 2652
<212> TYPE: DNA
<213> ORGANISM: Artificial
<220> FEATURE:
<223> OTHER INFORMATION: pACE

<400> SEQUENCE: 2
ggtaccgcgg ccgcgtagag gatctgttga tcagcagttc aacctgttga tagtacttcg    60
ttaatacaga tgtaggtgtt ggcaccatgc ataactataa cggtcctaag gtagcgacct   120
aggtatcgat aatacgactc actataggga aattgtgagc ggataacaat tcccctctag   180
aaataatttt gtttaacttt aagaaggaga tatacatatg aggcctcgga tcctgtaaaa   240
cgacggccag tgaattcccc gggaagcttc gccagggttt tcccagtcga gctcgatatc   300
ggtaccagcg gataacaatt tcacatccgg atcgcgaacg cgtctcgaga gatccggctg   360
ctaacaaagc ccgaaaggaa gctgagttgg ctgctgccac cgctgagcaa taactagcat   420
aaccccttgg ggcctctaaa cgggtcttga gggttttttt ggtttaaacc catctaattg   480
gactagtagc ccgcctaatg agcgggcttt ttttaattc ccctatttgt ttatttttct   540
aaatacattc aaatatgtat ccgctcatga gacaataacc ctgataaatg cttcaataat   600
attgaaaaag gaagagtatg agtattcaac atttccgtgt cgcccttatt ccctttttg    660
```

```
cggcattttg ccttcctgtt tttgctcacc cagaaacgct cgtgaaagta aaagacgcag    720
aggaccaatt gggggcacga gtgggataca tagaactgga cttgaatagc ggtaaaatcc    780
ttgagagttt tcgccctgaa gagcgttttc caatgatgag cactttcaaa gttctgctat    840
gtggagcagt attatcccgt gtagatgcgg ggcaagagca actcggacga cgaatacact    900
attcgcagaa tgacttggtt gaatactccc cagtgacaga aaagcacctt acggacggaa    960
tgacggtaag agaattatgt agtgccgcca taacgatgag tgataacact gcggcgaact   1020
tacttctgac aaccatcggt ggaccgaagg aattaaccgc ttttttgcac aatatgggag   1080
accatgtaac tcgccttgac cgttgggaac cagaactgaa tgaagccata ccaaacgacg   1140
agcgagacac cacaatgcct gcggcaatgg caacaacatt acgcaaacta ttaactggcg   1200
aactacttac tctggcttca cggcaacaat taatagactg gcttgaagcg gataaagttg   1260
caggaccact actgcgttcg gcacttcctg ctggctggtt tattgctgat aaatctgggg   1320
caggagagcg tggttcacgg ggtatcattg ccgcacttgg accagatggt aagccttccc   1380
gtatcgtagt tatctacacg acgggtagtc aggcaactat ggacgaacga aatagacaga   1440
ttgctgaaat aggggcttca ctgattaagc attggtaaac cgatacaatt aaaggctcct   1500
tttggagcct ttttttttgg acggaccggt agaaaagatc aaaggatctt cttgagatcc   1560 ttttttttctg cgcgtaatct gctgcttgca acaaaaaaaa ccaccgctac cagcggtggt   1620
ttgtttgccg gatcaagagc taccaactct ttttccgaag gtaactggct tcagcagagc   1680
gcagatacca aatactgtcc ttctagtgta gccgtagtta ggccaccact tcaagaactc   1740
tgtagcaccg cctacatacc tcgctctgct aatcctgtta ccagtggctg ctgccagtgg   1800
cgataagtcg tgtcttaccg ggttggactc aagacgatag ttaccggata aggcgcagcg   1860
gtcgggctga acggggggtt cgtgcacaca gcccagcttg gagcgaacga cctacaccga   1920
actgagatac ctacagcgtg agctatgaga aagcgccacg cttcccgaag ggagaaaggc   1980
ggacaggtat ccggtaagcg gcagggtcgg aacaggagag cgcacgaggg agcttccagg   2040
gggaaacgcc tggtatcttt atagtcctgt cgggtttcgc cacctctgac ttgagcgtcg   2100
atttttgtga tgctcgtcag ggggcggag cctatggaaa aacgccagca acgcggcctt   2160
tttacggttc ctggcctttt gctggccttt tgctcacatg ttctttcctg cgttatcccc   2220
tgattctgtg gataaccgta ttaccgcctt tgagtgagct gataccgctc gccgcagccg   2280
aacgaccgag cgcagcgagt cagtgagcga ggaagcggaa gagcgcctga tgcggtattt   2340
tctccttacg catctgtgcg gtatttcaca ccgcaatggt gcactctcag tacaatctgc   2400
tctgatgccg catagttaag ccagtataca ctccgctatc gctacgtgac tgggtcatgg   2460
ctgcgccccg acacccgcca cacccgctg acgcgccctg acgggcttgt ctgctcccgg   2520
catccgctta cagacaagct gtgaccgtct ccgggagctg catgtgtcag aggttttcac   2580
cgtcatcacc gaaacgcgcg aggcaggggg aattccagat aacttcgtat aatgtatgct   2640
atacgaagtt at                                                      2652
```

<210> SEQ ID NO 3
<211> LENGTH: 2982
<212> TYPE: DNA
<213> ORGANISM: Artificial
<220> FEATURE:
<223> OTHER INFORMATION: pACE2

<400> SEQUENCE: 3

```
atgaaatcta acaatgcgct catcgtcatc ctcggcaccg tcaccctgga tgctgtaggc    60
```

```
ataggcttgg ttatgccggt actgccgggc ctcttgcggg atatcgtcca ttccgacagc    120
atcgccagtc actatggcgt gctgctagcg ctatatgcgt tgatgcaatt tctatgcgca    180
cccgttctcg gagcactgtc cgaccgcttt ggccgccgcc cagtcctgct cgcttcgcta    240
cttggagcca ctatcgacta cgcgatcatg gcgaccacac ccgtcctgtg gattctctac    300 gccgacgca tcgtggccgg catcaccggc gccacaggtg cggttgctgg cgcctatatc    360
gccgacatca ccgatgggga agatcgggct cgccacttcg ggctcatgag cgcttgtttc    420
ggcgtgggta tggtggcagg ccccgtggcc ggggactgt tgggcgccat ctccttacat    480
gcaccattcc ttgcggcggc ggtgctcaac ggcctcaacc tactactggg ctgcttccta    540
atgcaggagt cgcataaggg agagcgccga cccatgccct tgagagcctt caacccagtc    600
agctccttcc ggtgggcgcg gggcatgact atcgtcgccg cacttatgac tgtcttcttt    660
atcatgcaac tcgtaggaca ggtgccggca gcgctctggg tcattttcgg cgaggaccgc    720
tttcgctgga gcgcgacgat gatcggcctg tcgcttgcgg tattcggaat cttgcacgcc    780
ctcgctcaag ccttcgtcac tggtcccgcc accaaacgtt tcggcgagaa gcaggccatt    840
atcgccggca tggcggccga cgcgctgggc tacgtcttgc tggcgttcgc gacgcgaggc    900
tggatggcct tccccattat gattcttctc gcttccggcg gcatcgggat gcccgcgttg    960
caggccatgc tgtccaggca ggtagatgac gaccatcagg acagcttca aggatcgctc    1020 gcggctctta ccagcctaac ttcgatcatt ggaccgctga tcgtcacggc gatttatgcc    1080
gcctcggcga gcacatggaa cgggttggca tggattgtag gcgccgccct ataccttgtc    1140
tgcctccccg cgttgcgtcg cggtgcatgg agccgggcca cctcgacctg aaccgataca    1200
attaaaggct ccttttggag ccttttttt tggacggacc ggtagaaaag atcaaaggat    1260
cttcttgaga tccttttttt ctgcgcgtaa tctgctgctt gcaaacaaaa aaaccaccgc    1320
taccagcggt ggtttgtttg ccggatcaag agctaccaac tcttttccg aaggtaactg    1380 gcttcagcag agcgcagata ccaaatactg tccttctagt gtagccgtag ttaggccacc    1440
acttcaagaa ctctgtagca ccgcctacat acctcgctct gctaatcctg ttaccagtgg    1500
ctgctgccag tggcgataag tcgtgtctta ccgggttgga ctcaagacga tagttaccgg    1560
ataaggcgca gcggtcgggc tgaacggggg gttcgtgcac acagcccagc ttggagcgaa    1620
cgacctacac cgaactgaga tacctacagc gtgagctatg agaaagcgcc acgcttcccg    1680
aagggagaaa ggcggacagg tatccggtaa gcggcagggt cggaacagga gagcgcacga    1740
gggagcttcc aggggggaaac gcctggtatc tttatagtcc tgtcgggttt cgccacctct    1800
gacttgagcg tcgatttttg tgatgctcgt caggggggcg gagcctatgg aaaaacgcca    1860
gcaacgcggc cttttttacgg ttcctggcct tttgctggcc ttttgctcac atgttctttc    1920
ctgcgttatc ccctgattct gtggataacc gtattaccgc ctttgagtga gctgataccg    1980
ctcgccgcag ccgaacgacc gagcgcagcg agtcagtgag cgaggaagcg gaagagcgcc    2040
tgatgcggta ttttctcctt acgcatctgt gcggtatttc acaccgcaat ggtgcactct    2100
cagtacaatc tgctctgatg ccgcatagtt aagccagtat acactccgct atcgctacgt    2160
gactgggtca tggctgcgcc ccgacacccg ccaacacccg ctgacgcgcc ctgacgggct    2220
tgtctgctcc cggcatccgc ttacagacaa gctgtgaccg tctccgggag ctgcatgtgt    2280
cagaggtttt caccgtcatc accgaaacgc gcgaggcagg gggaattcca gataacttcg    2340
tataatgtat gctatacgaa gttatggtac cgcggccgcg tagaggatct gttgatcagc    2400
agttcaacct gttgatagta cttcgttaat acagatgtag gtgttggcac catgcataac    2460
```

```
tataacggtc ctaaggtagc gacctaggta tcgataatac gactcactat agggqaattg    2520 tgagcggata acaattcccc tctagaaata attttgttta actttaagaa ggagatatac    2580
atatgaggcc tcggatcctg taaaacgacg gccagtgaat tccccgggaa gcttcgccag    2640
ggttttccca gtcgagctcg atatcggtac cagcggataa caatttcaca tccggatcgc    2700
gaacgcgtct cgagagatcc ggctgctaac aaagcccgaa aggaagctga gttggctgct    2760
gccaccgctg agcaataact agcataaccc cttggggcct ctaaacgggt cttgaggggt    2820
tttttggttt aaacccatct aattggacta gtagcccgcc taatgagcgg gcttttttt     2880 aattcccta tttgttttatt tttctaaata cattcaaata tgtatccgct catgagacaa    2940
taaccctgat aaatgcttca ataatattga aaaggaaga gt                         2982
```

<210> SEQ ID NO 4
<211> LENGTH: 2067
<212> TYPE: DNA
<213> ORGANISM: Artificial
<220> FEATURE:
<223> OTHER INFORMATION: pDC

<400> SEQUENCE: 4

```
atcaacgtct cattttcgcc aaaagttggc ccagatctat gtcgggtgcg gagaaagagg      60
taatgaaatg gcacctaggt atcgataata cgactcacta gggggaatt gtgagcggat      120 aacaattccc ctctagaaat aattttgttt aactttaaga aggagatata catatgaggc     180
ctcggatcct gtaaaacgac ggccagtgaa ttccccggga agcttcgcca gggttttccc     240
agtcgagctc gatatcggta ccagcggata acaatttcac atccggatcg cgaacgcgtc     300
tcgagagatc cggctgctaa caaagcccga aggaagctg agttggctgc tgccaccgct     360
gagcaataac tagcataacc ccttggggcc tctaaacggg tcttgagggg ttttttggtt    420
taaacccatg tgcctggcag ataacttcgt ataatgtatg ctatacgaag ttatggtacc     480
gcggccgcgt agaggatctg ttgatcagca gttcaacctg ttgatagtac gtactaagct     540
ctcatgtttc acgtactaag ctctcatgtt taacgtacta agctctcatg tttaacgaac     600
taaaccctca tggctaacgt actaagctct catggctaac gtactaagct ctcatgtttc     660
acgtactaag ctctcatgtt tgaacaataa aattaatata aatcagcaac ttaaatagcc     720
tctaaggttt aagttttat aagaaaaaaa agaatatata aggcttttaa agcttttaag     780
gtttaacggt tgtggacaac aagccaggga tgtaacgcac tgagaagccc ttagagcctc     840
tcaaagcaat tttgagtgac acaggaacac ttaacggctg acagaattag cttcacgctg     900
ccgcaagcac tcagggcgca agggctgcta aggaagcgg aacacgtaga agccagtcc     960 gcagaaacgg tgctgacccc ggatgaatgt cagctgggag gcagaataaa tgatcatatc    1020
gtcaattatt acctccacgg ggagagcctg agcaaactgg cctcaggcat ttgagaagca    1080
cacggtcaca ctgcttccgg tagtcaataa accggtaaac cagcaataga cataagcggc    1140
tatttaacga ccctgccctg aaccgacgac cgggtcgaat ttgctttcga atttctgcca    1200
ttcatccgct tattatcact tattcaggcg tagcaaccag gcgtttaagg gcaccaataa    1260
ctgccttaaa aaaattacgc cccgccctgc cactcatcgc agtactgttg taattcatta    1320
agcattctgc cgacatggaa gccatcacaa acggcatgat gaacctgaat cgccagcggc    1380
atcagcacct tgtcgccttg cgtataatat ttgcccatgg tgaaacgggg gcgaagaag    1440 ttgtccatat tggccacgtt taaatcaaaa ctggtgaaac tcacccaggg attggctgag    1500
acgaaaaaca tattctcaat aaaccccttta gggaaatagg ccaggttttc accgtaacac    1560
```

| | |
|---|---:|
| gccacatctt gcgaatatat gtgtagaaac tgccggaaat cgtcgtggta ttcactccag | 1620 |
| agcgatgaaa acgtttcagt tgctcatgg aaaacggtgt aacaagggtg aacactatcc | 1680 |
| catatcacca gctcaccgtc tttcattgcc atacggaatt ccggatgagc attcatcagg | 1740 |
| cgggcaagaa tgtgaataaa ggccggataa aacttgtgct tattttttctt tacggtcttt | 1800 |
| aaaaaggccg taatatccag ctgaacggtc tggttatagg tacattgagc aactgactga | 1860 |
| aatgcctcaa aatgttcttt acgatgccat gggatatat caacggtggt atatccagtg | 1920 |
| atttttttct ccatttttagc ttccttagct cctgaaaatc tcgataactc aaaaaatacg | 1980 |
| cccggtagtg atcttatttc attatggtga agttggacc ctcttacgtg ccgatcaacg | 2040 |
| tctcattttc gccaaaagtt ggcccag | 2067 |

<210> SEQ ID NO 5
<211> LENGTH: 2077
<212> TYPE: DNA
<213> ORGANISM: Artificial
<220> FEATURE:
<223> OTHER INFORMATION: pDK

<400> SEQUENCE: 5

| | |
|---|---:|
| ctatgtcggg tgcggagaaa gaggtaatga aatggcacct aggtatcgat ggctttacac | 60 |
| tttatgcttc cggctcgtat gttgtgtgga attgtgagcg ataacaatt tcacacagga | 120 |
| aacagctatg accatgatta cgaatttcta gaaataattt tgtttaactt taagaaggag | 180 |
| atatacatat gaggcctcgg atcctgtaaa acgacggcca gtgaattccc cgggaagctt | 240 |
| cgccagggtt ttcccagtcg agctcgatat cggtaccagc ggataacaat tcacatccg | 300 |
| gatcgcgaac gcgtctcgag actagttccg tttaaaccca tgtgcctggc agataacttc | 360 |
| gtataatgta tgctatacga agttatggta cgtactaagc tctcatgttt cacgtactaa | 420 |
| gctctcatgt ttaacgtact aagctctcat gtttaacgaa ctaaaccctc atggctaacg | 480 |
| tactaagctc tcatggctaa cgtactaagc tctcatgttt cacgtactaa gctctcatgt | 540 |
| ttgaacaata aaattaatat aaatcagcaa cttaaatagc ctctaaggtt ttaagttta | 600 |
| taagaaaaaa aagaatatat aaggctttta agcttttaa ggtttaacgg ttgtggacaa | 660 |
| caagccaggg atgtaacgca ctgagaagcc cttagagcct ctcaaagcaa ttttcagtga | 720 |
| cacaggaaca cttaacggct gacagaatta gcttcacgct gccgcaagca ctcagggcgc | 780 |
| aagggctgct aaaggaagcg gaacacgtag aaagccagtc gcagaaacg gtgctgaccc | 840 |
| cggatgaatg tcagctactg ggctatctgg acaagggaaa acgcaagcgc aaagagaaag | 900 |
| caggtagctt gcagtgggct tacatggcga tagctagact gggcggtttt atggacagca | 960 |
| agcgaaccgg aattgccagc tggggcgccc tctggtaagg ttgggaagcc ctgcaaagta | 1020 |
| aactggatgg cttttcttgcc gccaaggatc tgatggcgca ggggatcaag atctgatcaa | 1080 |
| gagacaggat gaggatcgtt tcgcatgatt gaacaagatg gattgcacgc aggttctccg | 1140 |
| gccgcttggg tggagaggct attcggctat gactgggcac aacagacaat cggctgctct | 1200 |
| gatgccgccg tgttccggct gtcagcgcag gggcgcccgg ttcttttttgt caagaccgac | 1260 |
| ctgtccggtg ccctgaatga actgcaggac gaggcagcgc ggctatcgtg gctggccacg | 1320 |
| acgggcgttc cttgcgcagc tgtgctcgac gttgtcactg aagcgggaag ggactggctg | 1380 |
| ctattgggcg aagtgccggg gcaggatctc ctgtcatctc accttgctcc tgccgagaaa | 1440 |
| gtatccatca tggctgatgc aatgcggcgg ctgcatacgc ttgatccggc tacctgccca | 1500 |
| ttcgaccacc aagcgaaaca tcgcatcgag cgagcacgta ctcggatgga agccggtctt | 1560 |

```
gtcgatcagg atgatctgga cgaagagcat caggggctcg cgccagccga actgttcgcc    1620
aggctcaagg cgcgcatgcc cgacggcgag gatctcgtcg tgacacatgg cgatgcctgc    1680
ttgccgaata tcatggtgga aaatggccgc ttttctggat tcatcgactg tggccggctg    1740
ggtgtggcgg accgctatca ggacatagcg ttggctaccc gtgatattgc tgaagagctt    1800
ggcggcgaat gggctgaccg cttcctcgtg ctttacggta tcgccgctcc cgattcgcag    1860
cgcatcgcct tctatcgcct tcttgacgag ttcttctgag cgggactctg gggttcgaaa    1920
tgaccgacca agcgacgccc aacctgccat cacgagattt cgattccacc gccgccttct    1980
atgaaaggtt gggcttcgga atcgttttcc gggacgccgg ctggatgatc ctccagcgcg    2040
gggatctcat gctggagttc ttcgcccacc ccgggat                              2077

<210> SEQ ID NO 6
<211> LENGTH: 2027
<212> TYPE: DNA
<213> ORGANISM: Artificial
<220> FEATURE:
<223> OTHER INFORMATION: pDS

<400> SEQUENCE: 6
ctatgtcggg tgcggagaaa gaggtaatga atggcacct aggtatcgat ggctttacac      60
tttatgcttc cggctcgtat gttgtgtgga attgtgagcg gataacaatt tcacacagga    120
aacagctatg accatgatta cgaatttcta gaaataattt tgtttaactt taagaaggag    180
atatacatat gaggcctcgg atcctgtaaa acgacggcca gtgaattccc cgggaagctt    240
cgccagggtt ttcccagtcg agctcgatat cggtaccagc ggataacaat ttcacatccg    300
gatcgcgaac gcgtctcgag actagttccg tttaaaccca tgtgcctggc agataacttc    360
gtataatgta tgctatacga agttatggta cgtactaagc tctcatgttt cacgtactaa    420
gctctcatgt ttaacgtact aagctctcat gtttaacgaa ctaaaccctc atggctaacg    480
tactaagctc tcatggctaa cgtactaagc tctcatgttt cacgtactaa gctctcatgt    540
ttgaacaata aaattaatat aaatcagcaa cttaaatagc ctctaaggtt ttaagtttta    600
taagaaaaaa aagaatatat aaggctttta agcttttaa ggtttaacgg ttgtggacaa    660
caagccaggg atgtaacgca ctgagaagcc cttagagcct ctcaaagcaa ttttgagtga    720
cacaggaaca cttaacggct gacataattc agcttcacgc tgccgcaagc actcagggcg    780
caagggctgc taaaggaagc ggaacacgta gaaagccagt ccgcagaaac ggtgctgacc    840
ccggatgaat gtcagctggg aggcagaata aatgatcata tcgtcaatta ttacctccac    900
ggggagagcc tgagcaaact ggcctcaggc atttgagaag cacacggtca cactgcttcc    960
ggtagtcaat aaaccggtaa gtagcgtatg cgctcacgca actggtccag aaccttgacc   1020
gaacgcagcg gtggtaacgg cgcagtggcg gttttcatgg cttgttatga ctgtttttt    1080 ggggtacagt ctatgcctcg ggcatccaag cagcaagcgc gttacgccgt gggtcgatgt   1140
ttgatgttat ggagcagcaa cgatgttacg cagcagggca gtcgccctaa acaaagttaa   1200
aacatcatga gggaagcggt gatcgccgaa gtatcgactc aactatcaga ggtagttggc   1260
gtcatcgagc gccatctcga accgacgttg ctggccgtac atttgtacgg ctccgcagtg   1320
gatggcggcc tgaagccaca cagtgatatt gatttgctgg ttacggtgac cgtaaggctt   1380
gatgaaacaa cgcggcgagc tttgatcaac gaccttttgg aaacttcggc ttcccctgga   1440
gagagcgaga ttctccgcgc tgtagaagtc accattgttg tgcacgacga catcattccg   1500
tggcgttatc cagctaagcg cgaactgcaa tttggagaat ggcagcgcaa tgacattctt   1560
```

| | | | |
|---|---|---|---|
| gcaggtatct | tcgagccagc | cacgatcgac | attgatctgg ctatcttgct gacaaaagca | 1620 |
| agagaacata | gcgttgcctt | ggtaggtcca | gcggcggagg aactctttga tccggttcct | 1680 |
| gaacaggatc | tatttgaggc | gctaaatgaa | accttaacgc tatggaactc gccgcccgac | 1740 |
| tgggctggcg | atgagcgaaa | tgtagtgctt | acgttgtccc gcatttggta cagcgcagta | 1800 |
| accggcaaaa | tcgcgccgaa | ggatgtcgct | gccgactggg caatgagcg cctgccggcc | 1860 |
| cagtatcagc | ccgtcatact | tgaagctaga | caggcttatc ttggacaaga agaagatcgc | 1920 |
| ttggcctcgc | gcgcagatca | gttggaagaa | tttgtccact acgtgaaagg cgagatcacc | 1980 |
| aaggtagtcg | gcaaataatg | tctaacaatt | cgttcaagcc gacggat | 2027 |

<210> SEQ ID NO 7
<211> LENGTH: 2346
<212> TYPE: DNA
<213> ORGANISM: Artificial
<220> FEATURE:
<223> OTHER INFORMATION: pIDC

<400> SEQUENCE: 7

| | | | |
|---|---|---|---|
| aaacccatgt | gcctggcaga | taacttcgta | taatgtatgc tatacgaagt tatggtaccg | 60 |
| cggccgcgta | gaggatctgt | tgatcagcag | ttcaacctgt tgatagtacg tactaagctc | 120 |
| tcatgtttca | cgtactaagc | tctcatgttt | aacgtactaa gctctcatgt ttaacgaact | 180 |
| aaaccctcat | ggctaacgta | ctaagctctc | atggctaacg tactaagctc tcatgtttca | 240 |
| cgtactaagc | tctcatgttt | gaacaataaa | attaatataa atcagcaact taaatagcct | 300 |
| ctaaggtttt | aagttttata | agaaaaaaaa | gaatatataa ggcttttaaa gcttttaagg | 360 |
| tttaacggtt | gtggacaaca | agccaggat | gtaacgcact gagaagccct tagagcctct | 420 |
| caaagcaatt | ttgagtgaca | caggaacact | taacggctga cagaattagc ttcacgctgc | 480 |
| cgcaagcact | cagggcgcaa | gggctgctaa | aggaagcgga acacgtagaa agccagtccg | 540 |
| cagaaacggt | gctgaccccg | gatgaatgtc | agctgggagg cagaataaat gatcatatcg | 600 |
| tcaattatta | cctccacggg | gagagcctga | gcaaactggc ctcaggcatt tgagaagcac | 660 |
| acggtcacac | tgcttccggt | agtcaataaa | ccggtaaacc agcaatagac ataagcggct | 720 |
| atttaacgac | cctgccctga | accgacgacc | gggtcgaatt tgctttcgaa tttctgccat | 780 |
| tcatccgctt | attatcactt | attcaggcgt | agcaaccagg cgtttaaggg caccaataac | 840 |
| tgccttaaaa | aaattacgcc | ccgccctgcc | actcatcgca gtactgttgt aattcattaa | 900 |
| gcattctgcc | gacatggaag | ccatcacaaa | cggcatgatg aacctgaatc gccagcggca | 960 |
| tcagcacctt | gtcgccttgc | gtataatatt | tgcccatggt gaaaacgggg gcgaagaagt | 1020 |
| tgtccatatt | ggccacgttt | aaatcaaaac | tggtgaaact cacccaggga ttggctgaga | 1080 |
| cgaaaaacat | attctcaata | aaccctttag | ggaaataggc caggttttca ccgtaacacg | 1140 |
| ccacatcttg | cgaatatatg | tgtagaaact | gccggaaatc gtcgtggtat tcactccaga | 1200 |
| gcgatgaaaa | cgtttcagtt | tgctcatgga | aaacggtgta acaagggtga acactatccc | 1260 |
| atatcaccag | ctcaccgtct | ttcattgcca | tacgaattc cggatgagca ttcatcaggc | 1320 |
| gggcaagaat | gtgaataaag | gccggataaa | acttgtgctt atttttcttt acggtcttta | 1380 |
| aaaaggccgt | aatatccagc | tgaacggtct | ggttataggt acattgagca actgactgaa | 1440 |
| atgcctcaaa | atgttcttta | cgatgccatt | gggatatatc aacggtggta tatccagtga | 1500 |
| tttttttctc | cattttagct | tccttagctc | ctgaaaatct cgataactca aaaaatacgc | 1560 |
| ccggtagtga | tcttatttca | ttatggtgaa | agttggaccc tcttacgtgc cgatcaacgt | 1620 |

-continued

```
ctcattttcg ccaaaagttg gcccagatca acgtctcatt ttcgccaaaa gttggcccag      1680
atctatgtcg ggtgcggaga aagaggtaat gaaatggcac ctaggggtta tgatagttat      1740
tgctcagcgg tggcagcagc caactcagct tcctttcggg ctttgttagc agccggatct      1800
tctaggctca agcagtgatc agatccagac atgataagat acattgatga gtttggacaa      1860
accacaacta gaatgcagtg aaaaaaatgc tttatttgtg aaatttgtga tgctattgct      1920
ttatttgtaa ccattataag ctgcaataaa caagttaaca acaacaattg cattcatttt      1980
atgtttcagg ttcagggga ggtgtgggag gttttttaaa gcaagtaaaa cctctacaaa       2040
tgtggtatgg ctgattatga tcctctagta cttctcgaca gcttgtcga gactgcaggc       2100 tctagattcg aaagcggccg cgactagtga gctcgtcgac gtaggccttt gaattccgcg      2160
cgcttcggac cgggatccgc gcccgatggt gggacggtat gaataatccg gaatatttat      2220
aggttttttt attacaaaac tgttacgaaa acagtaaaat acttatttat ttgcgagatg      2280
gttatcattt taattatctc catgatctat taatattccg gagtaggtcg cgaatcgata      2340
ctagta                                                                  2346
```

<210> SEQ ID NO 8
<211> LENGTH: 2281
<212> TYPE: DNA
<213> ORGANISM: Artificial
<220> FEATURE:
<223> OTHER INFORMATION: pIDK

<400> SEQUENCE: 8

```
gatactagta tacggacctt taattcaacc caacacaata tattatagtt aaataagaat        60
tattatcaaa tcatttgtat attaattaaa atactatact gtaaattaca ttttatttac       120
aatcactcga cgaagacttg atcacccggg atctcgagcc atggtgctag cagctgatgc       180
atagcatgcg gtaccgggag atgggggagg ctaactgaaa cacggaagga acaataccg        240 gaaggaaccc gcgctatgac ggcaataaaa agacagaata aaacgcacgg gtgttgggtc       300
gtttgttcat aaacgcgggg ttcggtccca gggctggcac tctgtcgata ccccaccgag       360
accccattgg gaccaatacg cccgcgtttc ttccttttcc ccaccccaac cccaagttc        420 gggtgaaggc ccagggctcg cagccaacgt cggggcggca agccctgcca tagccactac       480
gggtacgttt aaacccatgt gcctggcaga taacttcgta taatgtatgc tatacgaagt      540
tatggtacgt actaagctct catgtttcac gtactaagct ctcatgttta acgtactaag       600
ctctcatgtt taacgaacta aaccctcatg gctaacgtac taagctctca tggctaacgt      660
actaagctct catgtttcac gtactaagct ctcatgtttg aacaataaaa ttaatataaa      720
tcagcaactt aaatagcctc taaggtttta agttttataa gaaaaaaaag aatatataag       780
gcttttaaag cttttaaggt ttaacggttg tggacaacaa gccagggatg taacgcactg       840
agaagccctt agagcctctc aaagcaattt tcagtgacac aggaacactt aacggctgac       900
agaattagct tcacgctgcc gcaagcactc agggcgcaag gctgctaaa ggaagcggaa        960 cacgtagaaa gccagtccgc agaaacggtg ctgaccccgg atgaatgtca gctactgggc      1020
tatctggaca agggaaaacg caagcgcaaa gagaaagcag gtagcttgca gtgggcttac      1080
atggcgatag ctagactggg cggttttatg gacagcaagc gaaccggaat tgccagctgg      1140
ggcgccctct ggtaaggttg ggaagccctg caaagtaaac tggatggctt tcttgccgcc      1200
aaggatctga tggcgcaggg gatcaagatc tgatcaagag acaggatgag gatcgtttcg      1260
catgattgaa caagatggat tgcacgcagg ttctccggcc gcttgggtgg agaggctatt      1320
```

```
cggctatgac tgggcacaac agacaatcgg ctgctctgat gccgccgtgt tccggctgtc    1380
agcgcagggg cgcccggttc tttttgtcaa gaccgacctg tccggtgccc tgaatgaact    1440
gcaggacgag gcagcgcggc tatcgtggct ggccacgacg ggcgttcctt gcgcagctgt    1500
gctcgacgtt gtcactgaag cgggaaggga ctggctgcta ttgggcgaag tgccggggca    1560
ggatctcctg tcatctcacc ttgctcctgc cgagaaagta tccatcatgg ctgatgcaat    1620
gcggcggctg catacgcttg atccggctac ctgcccattc gaccaccaag cgaaacatcg    1680
catcgagcga gcacgtactc ggatggaagc cggtcttgtc gatcaggatg atctggacga    1740
agagcatcag gggctcgcgc cagccgaact gttcgccagg ctcaaggcgc gcatgcccga    1800
cggcgaggat ctcgtcgtga cacatggcga tgcctgcttg ccgaatatca tggtggaaaa    1860
tggccgcttt tctggattca tcgactgtgg ccggctgggt gtggcggacc gctatcagga    1920
catagcgttg gctacccgtg atattgctga agagcttggc ggcgaatggg ctgaccgctt    1980
cctcgtgctt tacggtatcg ccgctcccga ttcgcagcgc atcgccttct atcgccttct    2040
tgacgagttc ttctgagcgg gactctgggg ttcgaaatga ccgaccaagc gacgcccaac    2100
ctgccatcac gagatttcga ttccaccgcc gccttctatg aaaggttggg cttcggaatc    2160
gttttccggg acgccggctg gatgatcctc cagcgcgggg atctcatgct ggagttcttc    2220
gcccaccccg ggatctatgt cgggtgcgga gaaagaggta atgaaatggc acctaggtat    2280
c                                                                   2281

<210> SEQ ID NO 9
<211> LENGTH: 2231
<212> TYPE: DNA
<213> ORGANISM: Artificial
<220> FEATURE:
<223> OTHER INFORMATION: pIDS

<400> SEQUENCE: 9
cgatactagt atacggacct ttaattcaac ccaacacaat atattatagt taaataagaa      60
ttattatcaa atcatttgta tattaattaa aatactatac tgtaaattac attttattta     120
caatcactcg acgaagactt gatcacccgg gatctcgagc catggtgcta gcagctgatg     180
catagcatgc ggtaccggga gatgggggag gctaactgaa acacggaagg agacaatacc     240
ggaaggaacc cgcgctatga cggcaataaa aagacagaat aaaacgcacg ggtgtttggt     300
cgtttgttca taaacgcggg gttcggtccc agggctggca ctctgtcgat accccaccga     360 gacccccattg ggaccaatac gcccgcgttt cttccttttc cccaccccaa ccccaagtt    420 cgggtgaagg cccagggctc gcagccaacg tcgggcggc aagccctgcc atagccacta     480
cgggtacgtt taaacccatg tgcctggcag ataacttcgt ataatgtatg ctatacgaag     540
ttatggtacg tactaagctc tcatgtttca cgtactaagc tctcatgttt aacgtactaa     600
gctctcatgt ttaacgaact aaaccctcat ggctaacgta ctaagctctc atggctaacg     660
tactaagctc tcatgtttca cgtactaagc tctcatgttt gaacaataaa attaatataa     720
atcagcaact taaatagcct ctaaggtttt aagttttata agaaaaaaaa gaatatataa     780
ggcttttaaa gcttttaagg tttaacggtt gtggacaaca agccagggat gtaacgcact     840
gagaagccct tagagcctct caaagcaatt ttgagtgaca caggaacact taacggctga     900
cataattcag cttcacgctg ccgcaagcac tcagggcgca agggctgcta aggaagcgg     960 aacacgtaga aagccagtcc gcagaaacgg tgctgacccc ggatgaatgt cagctgggag    1020
gcagaataaa tgatcatatc gtcaattatt acctccacgg ggagagcctg agcaaactgg    1080
```

-continued

| | |
|---|---|
| cctcaggcat tgagaagca cacggtcaca ctgcttccgg tagtcaataa accggtaagt | 1140 |
| agcgtatgcg ctcacgcaac tggtccagaa ccttgaccga acgcagcggt ggtaacggcg | 1200 |
| cagtggcggt tttcatggct tgttatgact gttttttttgg ggtacagtct atgcctcggg | 1260 |
| catccaagca gcaagcgcgt tacgccgtgg gtcgatgttt gatgttatgg agcagcaacg | 1320 |
| atgttacgca gcagggcagt cgccctaaaa caaagttaaa catcatgagg gaagcggtga | 1380 |
| tcgccgaagt atcgactcaa ctatcagagg tagttggcgt catcgagcgc catctcgaac | 1440 |
| cgacgttgct ggccgtacat ttgtacggct ccgcagtgga tggcggcctg aagcccacaca | 1500 |
| gtgatattga tttgctggtt acggtgacgg taaggcttga tgaaacaacg cggcgagctt | 1560 |
| tgatcaacga ccttttggaa acttcggctt ccctggaga gagcgagatt ctccgcgctg | 1620 |
| tagaagtcac cattgttgtg cacgacgaca tcattccgtg gcgttatcca gctaagcgcg | 1680 |
| aactgcaatt tggagaatgg cagcgcaatg acattcttgc aggtatcttc gagccagcca | 1740 |
| cgatcgacat tgatctggct atcttgctga caaaagcaag agaacatagc gttgccttgg | 1800 |
| taggtccagc ggcggaggaa ctcttttgatc cggttcctga acaggatcta tttgaggcgc | 1860 |
| taaatgaaac cttaacgcta tggaactcgc cgcccgactg gctggcgat gagcgaaatg | 1920 |
| tagtgcttac gttgtcccgc atttggtaca gcgcagtaac cggcaaaatc gcgccgaagg | 1980 |
| atgtcgctgc cgactgggca atggagcgcc tgccggccca gtatcagccc gtcatacttg | 2040 |
| aagctagaca ggcttatctt ggacaagaag aagatcgctt ggcctcgcgc gcagatcagt | 2100 |
| tggaagaatt tgtccactac gtgaaaggcg agatcaccaa ggtagtcggc aaataatgtc | 2160 |
| taacaattcg ttcaagccga cggatctatg tcgggtgcgg agaaagaggt aatgaaatgg | 2220 |
| cacctaggta t | 2231 |

<210> SEQ ID NO 10
<211> LENGTH: 2904
<212> TYPE: DNA
<213> ORGANISM: Artificial
<220> FEATURE:
<223> OTHER INFORMATION: pACEBac1

<400> SEQUENCE: 10

| | |
|---|---|
| accggttgac ttgggtcaac tgtcagacca agtttactca tatatacttt agattgattt | 60 |
| aaaacttcat ttttaatttta aaaggatcta ggtgaagatc cttttttgata atctcatgac | 120 |
| caaaatccct taacgtgagt tttcgttcca ctgagcgtca gaccccgtag aaaagatcaa | 180 |
| aggatcttct tgagatcctt tttttctgcg cgtaatctgc tgcttgcaaa caaaaaaacc | 240 |
| accgctacca gcggtggttt gtttgccgga tcaagagcta ccaactcttt ttccgaaggt | 300 |
| aactggcttc agcagagcgc agataccaaa tactgttctt ctagtgtagc cgtagttagg | 360 |
| ccaccacttc aagaactctg tagcaccgcc tacatacctc gctctgctaa tcctgttacc | 420 |
| agtggctgct gccagtggcg ataagtcgtg tcttaccggg ttggactcaa gacgatagtt | 480 |
| accggataag gcgcagcggt cgggctgaac ggggggttcg tgcacacagc ccagcttgga | 540 |
| gcgaacgacc tacaccgaac tgagatacct acagcgtgag ctatgagaaa gcgccacgct | 600 |
| tcccgaaggg agaaaggcgg acaggtatcc ggtaagcggc agggtcggaa caggagagcg | 660 |
| cacgagggag cttccagggg gaaacgcctg gtatctttat agtcctgtcg ggtttcgcca | 720 |
| cctctgactt gagcgtcgat ttttgtgatg ctcgtcaggg gggcggagcc tatggaaaaa | 780 |
| cgccagcaac gcggccttttt tacggttcct ggccttttgc tggccttttg ctcacatgtt | 840 |
| ctttcctgcg ttatcccctg attgacttgg gtcgctcttc ctgtggatgc gcagatgccc | 900 |

| | |
|---|---|
| tgcgtaagcg ggtgtgggcg gacaataaag tcttaaactg aacaaaatag atctaaacta | 960 |
| tgacaataaa gtcttaaact agacagaata gttgtaaact gaaatcagtc cagttatgct | 1020 |
| gtgaaaaagc atactggact tttgttatgg ctaaagcaaa ctcttcattt tctgaagtgc | 1080 |
| aaattgcccg tcgtattaaa gagggggcgtg gccaagggca tgtaaagact atattcgcgg | 1140 |
| cgttgtgaca atttaccgaa caactccgcg gccgggaagc cgatctcggc ttgaacgaat | 1200 |
| tgttaggtgg cggtacttgg gtcgatatca aagtgcatca cttcttcccg tatgcccaac | 1260 |
| tttgtataga gagccactgc gggatcgtca ccgtaatctg cttgcacgta gatcacataa | 1320 |
| gcaccaagcg cgttggcctc atgcttgagg agattgatga gcgcggtggc aatgccctgc | 1380 |
| ctccggtgct cgccggagac tgcgagatca tagatataga tctcactacg cggctgctca | 1440 |
| aacttgggca gaacgtaagc cgcgagagcg ccaacaaccg cttcttggtc gaaggcagca | 1500 |
| agcgcgatga atgtcttact acggagcaag ttcccgaggt aatcggagtc cggctgatgt | 1560 |
| tgggagtagg tggctacgtc tccgaactca cgaccgaaaa gatcaagagc agcccgcatg | 1620 |
| gatttgactt ggtcagggcc gagcctacat gtgcgaatga tgcccatact tgagccacct | 1680 |
| aactttgttt tagggcgact gccctgctgc gtaacatcgt tgctgctgcg taacatcgtt | 1740 |
| gctgctccat aacatcaaac atcgacccac ggcgtaacgc gcttgctgct tggatgcccg | 1800 |
| aggcatagac tgtacaaaaa aacagtcata acaagccatg aaaaccgcca ctgcgccgtt | 1860 |
| accaccgctg cgttcggtca aggttctgga ccagttgcgt gagcgcatac gctacttgca | 1920 |
| ttacagttta cgaaccgaac aggcttatgt caactgggtt cgtgccttca tccgtttcca | 1980 |
| cggtgtgcgt cacccggcaa ccttgggcag cagcgaagtc gccataactt cgtatagcat | 2040 |
| acattatacg aagttatctg taactataac ggtcctaagg tagcgagttt aaacactagt | 2100 |
| atcgattcgc gacctactcc ggaatattaa tagatcatgg agataattaa aatgataacc | 2160 |
| atctcgcaaa taataagta ttttactgtt ttcgtaacag ttttgtaata aaaaaccta | 2220 |
| taaatattcc ggattattca taccgtccca ccatcgggcg cggatcccgg tccgaagcgc | 2280 |
| gcggaattca aaggcctacg tcgacgagct cacttgtcgc ggccgctttc gaatctagag | 2340 |
| cctgcagtct cgacaagctt gtcgagaagt actagaggat cataatcagc cataccacat | 2400 |
| ttgtagaggt tttacttgct ttaaaaaacc tcccacacct cccccctgaac ctgaaacata | 2460 |
| aaatgaatgc aattgttgtt gttaacttgt ttattgcagc ttataatggt tacaaataaa | 2520 |
| gcaatagcat cacaaatttc acaaataaag catttttttc actgcattct agttgtggtt | 2580 |
| tgtccaaact catcaatgta tcttatcatg tctggatctg atcactgctt gagcctagaa | 2640 |
| gatccggctg ctaacaaagc ccgaaaggaa gctgagttgg ctgctgccac cgctgagcaa | 2700 |
| taactatcat aacccctagg gtatacccat ctaattggaa ccagataagt gaaatctagt | 2760 |
| tccaaactat tttgtcattt ttaattttcg tattagctta cgacgctaca cccagttccc | 2820 |
| atctatttg tcactcttcc ctaaataatc cttaaaaact ccatttccac ccctcccagt | 2880 |
| tcccaactat tttgtccgcc caca | 2904 |

<210> SEQ ID NO 11
<211> LENGTH: 2761
<212> TYPE: DNA
<213> ORGANISM: Artificial
<220> FEATURE:
<223> OTHER INFORMATION: pACEBac2

<400> SEQUENCE: 11

| | |
|---|---|
| accggttgac ttgggtcaac tgtcagacca agtttactca tatatacttt agattgattt | 60 |

```
aaaacttcat ttttaattta aaaggatcta ggtgaagatc cttttttgata atctcatgac    120 caaaatccct taacgtgagt tttcgttcca ctgagcgtca gaccccgtag aaaagatcaa    180
aggatcttct tgagatcctt ttttttctgcg cgtaatctgc tgcttgcaaa caaaaaaacc    240
accgctacca gcggtggttt gtttgccgga tcaagagcta ccaactcttt ttccgaaggt    300
aactggcttc agcagagcgc agataccaaa tactgttctt ctagtgtagc cgtagttagg    360
ccaccacttc aagaactctg tagcaccgcc tacatacctc gctctgctaa tcctgttacc    420
agtggctgct gccagtggcg ataagtcgtg tcttaccggg ttggactcaa gacgatagtt    480
accggataag gcgcagcggt cgggctgaac ggggggttcg tgcacacagc ccagcttgga    540
gcgaacgacc tacaccgaac tgagatacct acagcgtgag ctatgagaaa gcgccacgct    600
tcccgaaggg agaaaggcgg acaggtatcc ggtaagcggc agggtcggaa caggagagcg    660
cacgagggag cttccagggg gaaacgcctg gtatctttat agtcctgtcg ggtttcgcca    720
cctctgactt gagcgtcgat ttttgtgatg ctcgtcaggg gggcggagcc tatggaaaaa    780
cgccagcaac gcggccttttt tacggttcct ggccttttgc tggccttttg ctcacatgtt    840
ctttcctgcg ttatcccctg attgacttgg gtcgctcttc ctgtggatgc gcagatgccc    900
tgcgtaagcg ggtgtgggcg gacaataaag tcttaaactg aacaaaatag atctaaacta    960
tgacaataaa gtcttaaact agacagaata gttgtaaact gaaatcagtc cagttatgct   1020
gtgaaaaagc atactggact tttgttatgg ctaaagcaaa ctcttcattt tctgaagtgc   1080
aaattgcccg tcgtattaaa gagggcgtg gccaagggca tgtaaagact atattcgcgg   1140
cgttgtgaca atttaccgaa caactccgcg gccgggaagc cgatctcggc ttgaacgaat   1200
tgttaggtgg cggtacttgg gtcgatatca aagtgcatca cttcttcccg tatgcccaac   1260
tttgtataga gagccactgc gggatcgtca ccgtaatctg cttgcacgta gatcacataa   1320
gcaccaagcg cgttggcctc atgcttgagg agattgatga gcgcggtggc aatgccctgc   1380
ctccggtgct cgccggagac tgcgagatca tagatataga tctcactacg cggctgctca   1440
aacttgggca gaacgtaagc cgcgagagcg ccaacaaccg cttcttggtc gaaggcagca   1500
agcgcgatga atgtcttact acggagcaag ttcccgaggt aatcggagtc cggctgatgt   1560
tgggagtagg tggctacgtc tccgaactca cgaccgaaaa gatcaagagc agcccgcatg   1620
gatttgactt ggtcagggcc gagcctacat gtgcgaatga tgcccatact tgagccacct   1680
aactttgttt tagggcgact gccctgctgc gtaacatcgt tgctgctgcg taacatcgtt   1740
gctgctccat aacatcaaac atcgacccac ggcgtaacgc gcttgctgct tggatgcccg   1800
aggcatagac tgtacaaaaa aacagtcata acaagccatg aaaaccgcca ctgcgccgtt   1860
accaccgctg cgttcggtca aggttctgga ccagttgcgt gagcgcatac gctacttgca   1920 ttacagtttta cgaaccgaac aggcttatgt caactgggtt cgtgccttca tccgtttcca   1980
cggtgtgcgt caccccggcaa ccttgggcag cagcgaagtc gccataactt cgtatagcat   2040
acattatacg aagttatctg taactataac ggtcctaagg tagcgagttt aaacgtaccc   2100
gtagtggcta tggcagggct tgccgccccg acgttggctg cgagccctgg gccttcaccc   2160
gaacttgggg gttggggtgg ggaaaaggaa gaaacgcggg cgtattggtc ccaatggggt   2220
ctcggtgggg tatcgacaga gtgccagccc tgggaccgaa ccccgcgttt atgaacaaac   2280
gacccaacac ccgtgcgttt tattctgtct ttttattgcc gtcatagcgc gggttccttc   2340
cggtattgtc tccttccgtg tttcagttag cctcccccat ctcccggtac cgcatgctat   2400
gcatcagctg ctagcaccat ggctcgagat cccgggtgat caagtcttcg tcgagtgatt   2460
```

```
gtaaataaaa tgtaatttac agtatagtat tttaattaat atacaaatga tttgataata    2520
attcttattt aactataata tattgtgttg ggttgaatta aaggtccgta tactagggta    2580
tacccatcta attggaacca gataagtgaa atctagttcc aaactatttt gtcatttta     2640 attttcgtat tagcttacga cgctacaccc agttcccatc tattttgtca ctcttcccta    2700
aataatcctt aaaaactcca tttccacccc tcccagttcc caactatttt gtccgcccac    2760
a                                                                     2761
```

<210> SEQ ID NO 12
<211> LENGTH: 2940
<212> TYPE: DNA
<213> ORGANISM: Artificial
<220> FEATURE:
<223> OTHER INFORMATION: pACEBac3

<400> SEQUENCE: 12

```
gcaacgcggc cttttacgg ttcctggcct tttgctggcc ttttgctcac atgttctttc      60
ctgcgttatc ccctgattga cttgggtcgc tcttcctgtg gatgcgcaga tgccctgcgt    120
aagcgggtgt gggcggacaa taaagtctta aactgaacaa aatagatcta aactatgaca    180
ataaagtctt aaactagaca gaatagttgt aaactgaaat cagtccagtt atgctgtgaa    240
aaagcatact ggactttgt tatggctaaa gcaaactctt cattctga agtgcaaatt       300 gcccgtcgta ttaagaggg gcgtggccaa gggcatgtaa agactatatt cgcggcgttg    360
tgacaattta ccgaacaact ccgcggccgg gaagccgatc tcggcttgaa cgaattgtta    420
ggtggcggta cttgggtcga tatcaaagtg catcacttct tcccgtatgc ccaactttgt    480
atagagagcc actgcgggat cgtcaccgta atctgcttgc acgtagatca cataagcacc    540
aagcgcgttg gcctcatgct tgaggagatt gatgagcgcg gtggcaatgc cctgcctccg    600
gtgctcgccg gagactgcga gatcatagat atagatctca ctacgcggct gctcaaactt    660
gggcagaacg taagccgcga gagcgccaac aaccgcttct tggtcgaagg cagcaagcgc    720
gatgaatgtc ttactacgga gcaagttccc gaggtaatcg gagtccggct gatgttggga    780
gtaggtggct acgtctccga actcacgacc gaaaagatca agagcagccc gcatggattt    840
gacttggtca gggccgagcc tacatgtgcg aatgatgccc atacttgagc cacctaactt    900
tgttttaggg cgactgccct gctgcgtaac atcgttgctg ctgcgtaaca tcgttgctgc    960
tccataacat caaacatcga cccacggcgt aacgcgcttg ctgcttggat gcccgaggca    1020
tagactgtac aaaaaaacag tcataacaag ccatgaaaac cgccactgcg ccgttaccac    1080
cgctgcgttc ggtcaaggtt ctggaccagt tgcgtgagcg catacgctac ttgcattaca    1140
gtttacgaac cgaacaggct tatgtcaact gggttcgtgc cttcatccgt ttccacggtg    1200
tgcgtcaccc ggcaaccttg gcagcagcg aagtcgccat aacttcgtat agcatacatt     1260
atacgaagtt atctgtaact ataacggtcc taaggtagcg agtttaaaca ctagtatcga    1320
ttcgcgacct actccggaat attaatagat catggagata attaaaatga taaccatctc    1380
gcaaataaat aagtatttta ctgttttcgt aacagttttg taataaaaaa acctataaat    1440
attccggatt attcataccg tcccaccatc gggcgcggat cccggtccga agcgcgcgga    1500
attcaaaggc ctacgtcgac gagctcactt gtcgcggccg ctttcgaatc tagagcctgc    1560
agtctcgaca agcttgtcga gaagtactag aggatcataa tcagccatac cacatttgta    1620
gaggttttac ttgctttaaa aaacctccca cacctcccccc tgaacctgaa acataaaatg    1680
aatgcaattg ttgttgttaa cttgtttatt gcagcttata atggttacaa ataaagcaat    1740
```

```
agcatcacaa atttcacaaa taaagcattt ttttcactgc attctagttg tggtttgtcc   1800
aaactcatca atgtatctta tcatgtctgg atctgatcac tgcttgagcc tagaagatcc   1860
ggctgctaac aaagcccgaa aggaagctga gttggctgct gccaccgctg agcaataact   1920
atcataaccc ctagggtata cccatctaat tggaaccaga taagtgaaat ctagttccaa   1980
actattttgt catttttaat tttcgtatta gcttacgacg ctacacccag ttcccatcta   2040
ttttgtcact cttccctaaa taatccttaa aaactccatt tccacccctc ccagttccca   2100
actattttgt ccgcccacaa ccggttgact tgggtcaact gtcagaccaa gtttactcat   2160
atatacttta gattgattta aaacttcatt tttaatttaa aaggatctag gtgaagatcc   2220
tttttgataa tctcatgacc acaggcattg gcggccttgc tgttcttcta cggcaaggtg   2280
ctgtgcacgc ccagctgcca ttttgggt gaggtcgttc gcggccgagg ggcgcagccc   2340 ctgggggat ggggtgccgc gttagcgggc cgggagggtt cgagaagggg gggcaccccc    2400
cttcggcgtg cgcggtcacg cgccagggcg cagccctggt aaaaacaag gtttataaat    2460 attggtttaa aagcaggtta aaagacaggt tagcggtggc cgaaaaacgg gcggaaaccc   2520
ttgcaaatgc tggattttct gcctgtggac agcccctcaa atgtcaatag gtgcgccct    2580 catctgtcat cactctgccc ctcaagtgtc aaggatcgcg cccctcatct gtcagtagtc   2640
gcgcccctca gtgtcaata ccgcaggca cttatcccca ggcttgtcca catcatctgt     2700
gggaaactcg cgtaaaatca ggcgttttcg ccgatttgcg aggctggcca gctccacgtc   2760
gccggccgaa atcgagcctg cccctcatct gtcaacgccg cgccgggtga gtcggccct    2820 caagtgtcaa cgtccgcccc tcatctgtca gtgagggcca gttttccgc gtggtatcca   2880 caacgccggc ggccaaaaga gagctttca caccgcatag accagccgcg taacctggca   2940

<210> SEQ ID NO 13
<211> LENGTH: 2805
<212> TYPE: DNA
<213> ORGANISM: Artificial
<220> FEATURE:
<223> OTHER INFORMATION: pACEBac4

<400> SEQUENCE: 13
gcaacgcggc cttttacgg ttcctggcct tttgctggcc ttttgctcac atgttctttc     60
ctgcgttatc ccctgattga cttgggtcgc tcttcctgtg gatgcgcaga tgccctgcgt   120
aagcgggtgt gggcggacaa taaagtctta aactgaacaa atagatcta aactatgaca    180 ataaagtctt aaactagaca gaatagttgt aaactgaaat cagtccagtt atgctgtgaa   240
aaagcatact ggacttttgt tatggctaaa gcaaactctt cattttctga agtgcaaatt   300
gcccgtcgta ttaaagaggg gcgtggccaa gggcatgtaa agactatatt cgcggcgttg   360
tgacaattta ccgaacaact ccgcggccgg aagccgatc tcggcttgaa cgaattgtta   420
ggtggcggta cttgggtcga tatcaaagtg catcacttct tcccgtatgc ccaactttgt   480
atagagagcc actgcgggat cgtcaccgta atctgcttgc acgtagatca cataagcacc   540
aagcgcgttg gcctcatgct tgaggagatt gatgagcgcg gtggcaatgc cctgcctccg   600
gtgctcgccg gagactgcga gatcatagat atagatctca ctacgcggct gctcaaactt   660
gggcagaacg taagccgcga gagcgccaac aaccgcttct tggtcgaagg cagcaagcgc   720
gatgaatgtc ttactacgga gcaagttccc gaggtaatcg gagtccggct gatgttggga   780
gtaggtggct acgtctccga actcacgacc gaaaagatca gagcagccc gcatggattt     840 gacttggtca gggccgagcc tacatgtgcg aatgatgccc atacttgagc cacctaactt   900
```

```
tgttttaggg cgactgccct gctgcgtaac atcgttgctg ctgcgtaaca tcgttgctgc    960
tccataacat caaacatcga cccacggcgt aacgcgcttg ctgcttggat gcccgaggca   1020
tagactgtac aaaaaaacag tcataacaag ccatgaaaac cgccactgcg ccgttaccac   1080
cgctgcgttc ggtcaaggtt ctggaccagt tgcgtgagcg catacgctac ttgcattaca   1140
gtttacgaac cgaacaggct tatgtcaact gggttcgtgc cttcatccgt ttccacggtg   1200
tgcgtcaccc ggcaaccttg ggcagcagcg aagtcgccat aacttcgtat agcatacatt   1260
atacgaagtt atctgtaact ataacggtcc taagtagcg agtttaaacg tacccgtagt   1320
ggctatggca gggcttgccg ccccgacgtt ggctgcgagc cctgggcctt cacccgaact   1380
tgggggttgg ggtggggaaa aggaagaaac gcggcgtat tggtcccaat ggggtctcgg   1440
tggggtatcg acagagtgcc agccctggga ccgaaccccg cgtttatgaa caaacgaccc   1500
aacacccgtg cgttttattc tgtcttttta ttgccgtcat agcgcgggtt ccttccggta   1560
ttgtctcctt ccgtgtttca gttagcctcc cccatctccc ggtaccgcat gctatgcatc   1620
agctgctagc accatggctc gagatcccgg gtgatcaagt cttcgtcgag tgattgtaaa   1680
taaaatgtaa tttacagtat agtattttaa ttaatataca aatgatttga taataattct   1740
tatttaacta taatatattg tgttgggttg aattaaaggt ccgtatacta gtatcctagg   1800
gtatacccat ctaattggaa ccagataagt gaaatctagt tccaaactat tttgtcattt   1860
ttaattttcg tattagctta cgacgctaca cccagttccc atctattttg tcactcttcc   1920
ctaaataatc cttaaaaact ccatttccac ccctcccagt tcccaactat tttgtccgcc   1980
cacaaccggt tgacttgggt caactgtcag accaagttta ctcatatata ctttagattg   2040
atttaaaact tcattttaa tttaaaagga tctaggtgaa gatcctttt gataatctca   2100 tgaccacagg cattggcggc cttgctgttc ttctacggca aggtgctgtg cacgcccagc   2160
tgccattttt ggggtgaggt cgttcgcggc cgaggggcgc agcccctggg gggatggggt   2220
gccgcgttag cgggccggga gggttcgaga agggggggca cccccttcg gcgtgcgcgg   2280 tcacgcgcca gggcgcagcc ctggttaaaa acaaggttta taatattgg tttaaaagca   2340 ggttaaaaga caggttagcg gtggccgaaa acgggcgga aacccttgca aatgctggat   2400
tttctgcctg tggacagccc ctcaaatgtc aataggtgcg cccctcatct gtcatcactc   2460
tgcccctcaa gtgtcaagga tcgcgcccct catctgtcag tagtcgcgcc cctcaagtgt   2520
caataccgca gggcacttat ccccaggctt gtccacatca tctgtgggaa actcgcgtaa   2580
aatcaggcgt tttcgccgat ttgcgaggct ggccagctcc acgtcgccgg ccgaaatcga   2640
gcctgcccct catctgtcaa cgccgcgccg ggtgagtcgg cccctcaagt gtcaacgtcc   2700 gccctcatc tgtcagtgag ggccaagttt tccgcgtggt atccacaacg ccggcggcca   2760
aaagaagagc tttcacaccg catagaccag ccgcgtaacc tggca                  2805
```

<210> SEQ ID NO 14
<211> LENGTH: 4589
<212> TYPE: DNA
<213> ORGANISM: Artificial
<220> FEATURE:
<223> OTHER INFORMATION: pOmniBac1

<400> SEQUENCE: 14

```
accggtggag gaaattctcc ttgaagtttc cctggtgttc aaagtaaagg agtttgcacc     60
agacgcacct ctgttcactg gtccggcgta ttaaaacacg atacattgtt attagtacat    120
ttattaagcg ctagattctg tgcgttgttg atttacagac aattgttgta cgtattttaa    180
```

```
taattcatta aatttataat ctttagggtg gtatgttaga gcgaaaatca aatgattttc      240
agcgtcttta tatctgaatt taaatattaa atcctcaata gatttgtaaa ataggtttcg      300
attagtttca aacaagggtt gttttttccga accgatggct ggactatcta atggattttc     360
gctcaacgcc acaaaacttg ccaaatcttg tagcagcaat ctagctttgt cgatattcgt      420
ttgtgttttg ttttgtaata aaggttcgac gtcgttcaaa atattatgcg cttttgtatt      480
tctttcatca ctgtcgttag tgtacaattg actcgacgta aacacgttaa atagagcttg      540
gacatattta acatcgggcg tgttagcttt attaggccga ttatcgtcgt cgtcccaacc      600
ctcgtcgtta gaagttgctt ccgaagacga ttttgccata gccacacgac gcctattaat      660
tgtgtcggct aacacgtccg cgatcaaatt tgtagttgag cttttttggaa ttaccggttg     720 acttgggtca actgtcagac caagtttact catatatact ttagattgat ttaaaacttc      780 attttttaatt taaaaggatc taggtgaaga tccttttttga taatctcatg accaaaatcc    840
cttaacgtga gttttcgttc cactgagcgt cagaccccgt agaaaagatc aaaggatctt      900
cttgagatcc ttttttttctg cgcgtaatct gctgcttgca aacaaaaaaa ccaccgctac     960
cagcggtggt ttgtttgccg gatcaagagc taccaactct ttttccgaag gtaactggct     1020
tcagcagagc gcagatacca aatactgttc ttctagtgta gccgtagtta ggccaccact     1080
tcaagaactc tgtagcaccg cctacatacc tcgctctgct aatcctgtta ccagtggctg     1140
ctgccagtgg cgataagtcg tgtcttaccg ggttggactc aagacgatag ttaccggata     1200
aggcgcagcg gtcgggctga acggggggtt cgtgcacaca gcccagcttg gagcgaacga    1260
cctacaccga actgagatac ctacagcgtg agctatgaga aagcgccacg cttcccgaag     1320
ggagaaaggc ggacaggtat ccggtaagcg gcagggtcgg aacaggagag cgcacgaggg     1380
agcttccagg gggaaacgcc tggtatcttt atagtcctgt cgggtttcgc cacctctgac     1440
ttgagcgtcg atttttgtga tgctcgtcag ggggggcggag cctatggaaa aacgccagca     1500
acgcggcctt tttacggttc ctggccttttt gctggccttt tgctcacatg ttctttcctg     1560
cgttatcccc tgattgactt gggtcgctct tcctgtggat gcgcaggtat gtacaggaag     1620
aggtttatac taaactgtta cattgcaaac gtggtttcgt gtgccaagtg tgaaaaccga     1680
tgtttaatca aggctctgac gcatttctac aaccacgact ctaagtgtgt gggtgaagtc     1740
atgcatcttt taatcaaatc ccaagatgtg tataaaccac caaactgcca aaaaatgaaa     1800
actgtcgaca agctctgtcc gtttgctggc aactgcaagg gtctcaatcc tatttgtaat     1860
tattgaataa taaaacaatt ataaatgtca aatttgtttt ttattaacga tacaaaccaa     1920
acgcaacaag aacatttgta gtattatcta taattgaaaa cgcgtagtta taatcgctga     1980
ggtaatattt aaaatcattt tcaaatgatt cacagttaat ttgcgacaat ataatttat     2040 tttcacataa actagacgcc ttgtcgtctt cttcttcgta ttccttctct ttttcattt      2100 tctcttcata aaaattaaca tagttattat cgtatccata tatgtatcta tcgtatagag     2160
taaatttttt gttgtcataa atatatatgt ctttttttaat ggggtgtata gtaccgctgc    2220
gcatagtttt tctgtaatttt acaacagtgc tattttctgg tagttcttcg gagtgtgttg    2280
ctttaattat taaatttata taatcaatga atttgggatc gtcggttttg tacaatatgt     2340
tgccggcata gtacgcagct tcttctagtt caattcacc attttttagc agcaccggat     2400
taacataact ttccaaaatg ttgtacgaac cgttaaacaa aaacagttca cctccctttt     2460
ctatactatt gtctgcgagc agttgttgt tgttaaaaat aacagccatt gtaatgagac     2520
gcacaaacta atatcacaaa ctggaaatgt ctatcaatat atagttgctg attgcgcaga     2580
```

```
tgccctgcgt aagcgggtgt gggcggacaa taaagtctta aactgaacaa aatagatcta   2640
aactatgaca ataaagtctt aaactagaca gaatagttgt aaactgaaat cagtccagtt   2700
atgctgtgaa aaagcatact ggacttttgt tatggctaaa gcaaactctt cattttctga   2760
agtgcaaatt gcccgtcgta ttaaagaggg gcgtggccaa gggcatgtaa agactatatt   2820
cgcggcgttg tgacaattta ccgaacaact ccgcggccgg gaagccgatc tcggcttgaa   2880
cgaattgtta ggtggcggta cttgggtcga tatcaaagtg catcacttct tcccgtatgc   2940
ccaactttgt atagagagcc actgcgggat cgtcaccgta atctgcttgc acgtagatca   3000
cataagcacc aagcgcgttg gcctcatgct tgaggagatt gatgagcgcg gtggcaatgc   3060
cctgcctccg gtgctcgccg gagactgcga gatcatagat atagatctca ctacgcggct   3120
gctcaaactt gggcagaacg taagccgcga gagcgccaac aaccgcttct tggtcgaagg   3180
cagcaagcgc gatgaatgtc ttactacgga gcaagttccc gaggtaatcg gagtccggct   3240
gatgttggga gtaggtggct acgtctccga actcacgacc gaaaagatca agagcagccc   3300
gcatggattt gacttggtca gggccgagcc tacatgtgcg aatgatgccc atacttgagc   3360
cacctaactt tgttttaggg cgactgccct gctgcgtaac atcgttgctg ctgcgtaaca   3420
tcgttgctgc tccataacat caaacatcga cccacggcgt aacgcgcttg ctgcttggat   3480
gcccgaggca tagactgtac aaaaaaacag tcataacaag ccatgaaaac cgccactgcg   3540
ccgttaccac cgctgcgttc ggtcaaggtt ctggaccagt tgcgtgagcg catacgctac   3600
ttgcattaca gtttacgaac cgaacaggct tatgtcaact gggttcgtgc cttcatccgt   3660
ttccacggtg tgcgtcaccc ggcaaccttg ggcagcagcg aagtcgccat aacttcgtat   3720
agcatacatt atacgaagtt atctgtaact ataacggtcc taaggtagcg agtttaaaca   3780
ctagtatcga ttcgcgacct actccggaat attaatagat catggagata attaaaatga   3840
taaccatctc gcaaataaat aagtatttta ctgttttcgt aacagttttg taataaaaaa   3900
acctataaat attccggatt attcataccg tcccaccatc gggcgcggat cccggtccga   3960
agcgcgcgga attcaaaggc ctacgtcgac gagctcactt gtcgcggccg ctttcgaatc   4020
tagagcctgc agtctcgaca agcttgtcga gaagtactag aggatcataa tcagccatac   4080
cacatttgta gaggttttac ttgctttaaa aaacctccca cacctccccc tgaacctgaa   4140
acataaaatg aatgcaattg ttgttgttaa cttgtttatt gcagcttata atggttacaa   4200
ataaagcaat agcatcacaa atttcacaaa taaagcattt ttttcactgc attctagttg   4260
tggtttgtcc aaactcatca atgtatctta tcatgtctgg atctgatcac tgcttgagcc   4320
tagaagatcc ggctgctaac aaagcccgaa aggaagctga gttggctgct gccaccgctg   4380
agcaataact atcataaccc ctagggtata cccatctaat tggaaccaga taagtgaaat   4440
ctagttccaa actattttgt cattttaat tttcgtatta gcttacgacg ctacacccag   4500
ttcccatcta ttttgtcact cttccctaaa taatccttaa aaactccatt tccacccctc   4560
ccagttccca actattttgt ccgcccaca                                      4589
```

<210> SEQ ID NO 15
<211> LENGTH: 4446
<212> TYPE: DNA
<213> ORGANISM: Artificial
<220> FEATURE:
<223> OTHER INFORMATION: pOmniBac2

<400> SEQUENCE: 15

```
ccggtggagg aaattctcct tgaagtttcc ctggtgttca agtaaaggag gtttgcacca     60
```

```
gacgcacctc tgttcactgg tccggcgtat taaaacacga tacattgtta ttagtacatt    120
tattaagcgc tagattctgt gcgttgttga tttacagaca attgttgtac gtattttaat    180
aattcattaa atttataatc tttagggtgg tatgttagag cgaaaatcaa atgattttca    240
gcgtctttat atctgaattt aaatattaaa tcctcaatag atttgtaaaa taggtttcga    300
ttagtttcaa acaagggttg ttttttccgaa ccgatggctg gactatctaa tggattttcg    360
ctcaacgcca caaaacttgc caaatcttgt agcagcaatc tagctttgtc gatattcgtt    420
tgtgttttgt tttgtaataa aggttcgacg tcgttcaaaa tattatgcgc ttttgtattt    480
ctttcatcac tgtcgttagt gtacaattga ctcgacgtaa acacgttaaa tagagcttgg    540
acatatttaa catcgggcgt gttagcttta ttaggccgat tatcgtcgtc gtcccaaccc    600
tcgtcgttag aagttgcttc cgaagacgat tttgccatag ccacacgacg cctattaatt    660
gtgtcggcta acacgtccgc gatcaaattt gtagttgagc ttttggaat taccggttga    720
cttgggtcaa ctgtcagacc aagtttactc atatatactt tagattgatt taaaacttca    780
tttttaattt aaaaggatct aggtgaagat cctttttgat aatctcatga ccaaaatccc    840
ttaacgtgag ttttcgttcc actgagcgtc agacccgta gaaaagatca aaggatcttc    900
ttgagatcct ttttttctgc gcgtaatctg ctgcttgcaa acaaaaaaac caccgctacc    960
agcggtggtt tgtttgccgg atcaagagct accaactctt tttccgaagg taactggctt   1020
cagcagagcg cagataccaa atactgttct tctagtgtag ccgtagttag gccaccactt   1080
caagaactct gtagcaccgc ctacatacct cgctctgcta atcctgttac cagtggctgc   1140
tgccagtggc gataagtcgt gtcttaccgg gttggactca agacgatagt taccggataa   1200
ggcgcagcgg tcgggctgaa cggggggttc gtgcacacag cccagcttgg agcgaacgac   1260
ctacaccgaa ctgagatacc tacagcgtga gctatgagaa agcgccacgc ttcccgaagg   1320
gagaaaggcg gacaggtatc cggtaagcgg cagggtcgga acaggagagc gcacgaggga   1380
gcttccaggg ggaaacgcct ggtatcttta tagtcctgtc gggtttcgcc acctctgact   1440
tgagcgtcga ttttttgtgat gctcgtcagg ggggcggagc ctatggaaaa acgccagcaa   1500
cgcggccttt ttacggttcc tggccttttg ctggcctttt gctcacatgt tctttcctgc   1560
gttatcccct gattgacttg gtcgctctct cctgtggatg cgcaggtatg tacaggaaga   1620
ggtttatact aaactgttac attgcaaacg tggtttcgtg tgccaagtgt gaaaaccgat   1680
gtttaatcaa ggctctgacg catttctaca accacgactc taagtgtgtg ggtgaagtca   1740
tgcatctttt aatcaaatcc caagatgtgt ataaaccacc aaactgccaa aaaatgaaaa   1800
ctgtcgacaa gctctgtccg tttgctggca actgcaaggg tctcaatcct atttgtaatt   1860
attgaataat aaaacaatta taaatgtcaa atttgttttt tattaacgat acaaaccaaa   1920
cgcaacaaga acatttgtag tattatctat aattgaaaac gcgtagttat aatcgctgag   1980
gtaatatttta aaatcatttt caaatgattc acagttaatt tgcgacaata taattttatt   2040
ttcacataaa ctagacgcct tgtcgtcttc ttcttcgtat tccttctctt tttcatttt    2100
ctcttcataa aaattaacat agttattatc gtatccatat atgtatctat cgtatagagt   2160
aaatttttg ttgtcataaa tatatatgtc tttttaatg gggtgtatag taccgctgcg    2220
catagttttt ctgtaattta caacagtgct attttctgg agttcttcgg agtgtgttgc    2280
tttaattatt aaatttatat aatcaatgaa tttgggatcg tcggttttgt acaatatgtt   2340
gccggcatag tacgcagctt cttctagttc aattacacca tttttagca gcaccggatt    2400
aacataactt tccaaaatgt tgtacgaacc gttaaacaaa aacagttcac ctccctttc    2460
```

```
tatactattg tctgcgagca gttgtttgtt gttaaaaata acagccattg taatgagacg    2520
cacaaactaa tatcacaaac tggaaatgtc tatcaatata tagttgctga ttgcgcagat    2580
gccctgcgta agcgggtgtg ggcggacaat aaagtcttaa actgaacaaa atagatctaa    2640
actatgacaa taaagtctta aactagacag aatagttgta aactgaaatc agtccagtta    2700
tgctgtgaaa aagcatactg gacttttgtt atggctaaag caaactcttc attttctgaa    2760
gtgcaaattg cccgtcgtat taagaggggg cgtggccaag ggcatgtaaa gactatattc    2820
gcggcgttgt gacaatttac cgaacaactc cgcggccggg aagccgatct cggcttgaac    2880
gaattgttag gtggcggtac ttgggtcgat atcaaagtgc atcacttctt cccgtatgcc    2940
caactttgta tagagagcca ctgcgggatc gtcaccgtaa tctgcttgca cgtagatcac    3000
ataagcacca agcgcgttgg cctcatgctt gaggagattg atgagcgcgg tggcaatgcc    3060
ctgcctccgg tgctcgccgg agactgcgag atcatagata tagatctcac tacgcggctg    3120
ctcaaacttg ggcagaacgt aagccgcgag agcgccaaca accgcttctt ggtcgaaggc    3180
agcaagcgcg atgaatgtct tactacggag caagttcccg aggtaatcgg agtccggctg    3240
atgttgggag taggtggcta cgtctccgaa ctcacgaccg aaaagatcaa gagcagcccg    3300
catggatttg acttggtcag ggccgagcct acatgtgcga atgatgccca tacttgagcc    3360
acctaacttt gttttagggc gactgccctg ctgcgtaaca tcgttgctgc tgcgtaacat    3420
cgttgctgct ccataacatc aaacatcgac ccacggcgta acgcgcttgc tgcttggatg    3480
cccgaggcat agactgtaca aaaaaacagt cataacaagc catgaaaacc gccactgcgc    3540
cgttaccacc gctgcgttcg gtcaaggttc tggaccagtt gcgtgagcgc atacgctact    3600
tgcattacag tttacgaacc gaacaggctt atgtcaactg ggttcgtgcc ttcatccgtt    3660
tccacggtgt gcgtcacccg gcaaccttgg gcagcagcga agtcgccata acttcgtata    3720
gcatacatta tacgaagtta tctgtaacta taacggtcct aaggtagcga gtttaaacgt    3780
acccgtagtg gctatggcag ggcttgccgc cccgacgttg gctgcgagcc ctgggccttc    3840
acccgaactt gggggttggg gtggggaaaa ggaagaaacg cgggcgtatt ggtcccaatg    3900
gggtctcggt ggggtatcga cagagtgcca gccctgggac cgaacccgc gtttatgaac    3960
aaacgaccca acaccgtgc gttttattct gtcttttat tgccgtcata gcgcgggttc    4020
cttccggtat tgtctccttc cgtgtttcag ttagcctccc ccatctcccg gtaccgcatg    4080
ctatgcatca gctgctagca ccatggctcg agatcccggg tgatcaagtc ttcgtcgagt    4140
gattgtaaat aaaatgtaat ttacagtata gtattttaat taatatacaa atgatttgat    4200
aataattctt atttaactat aatatattgt gttgggttga attaaaggtc cgtatactag    4260
ggtatacccca tctaattgga accagataag tgaaatctag ttccaaacta ttttgtcatt    4320
tttaattttc gtattagctt acgacgctac acccagttcc catctatttt gtcactcttc    4380
cctaaataat ccttaaaaac tccatttcca cccctcccag ttcccaacta ttttgtccgc    4440
ccacaa                                                               4446
```

<210> SEQ ID NO 16
<211> LENGTH: 4625
<212> TYPE: DNA
<213> ORGANISM: Artificial
<220> FEATURE:
<223> OTHER INFORMATION: pOmniBac3

<400> SEQUENCE: 16

```
gcaacgcggc cttttacgg ttcctggcct tttgctggcc ttttgctcac atgttctttc      60
```

```
ctgcgttatc ccctgattga cttgggtcgc tcttcctgtg gatgcgcagg tatgtacagg    120
aagaggttta tactaaactg ttacattgca aacgtggttt cgtgtgccaa gtgtgaaaac    180
cgatgtttaa tcaaggctct gacgcatttc tacaaccacg actctaagtg tgtgggtgaa    240
gtcatgcatc ttttaatcaa atcccaagat gtgtataaac caccaaactg ccaaaaaatg    300
aaaactgtcg acaagctctg tccgtttgct ggcaactgca agggtctcaa tcctatttgt    360
aattattgaa taataaaaca attataaatg tcaaatttgt tttttattaa cgatacaaac    420
caaacgcaac aagaacattt gtagtattat ctataattga aaacgcgtag ttataatcgc    480
tgaggtaata tttaaaatca ttttcaaatg attcacagtt aatttgcgac aatataattt    540
tattttcaca taaactagac gccttgtcgt cttcttcttc gtattccttc tcttttcat    600 ttttctcttc ataaaaatta acatagttat tatcgtatcc atatatgtat ctatcgtata    660
gagtaaattt tttgttgtca taaatatata tgtcttttt aatggggtgt atagtaccgc    720
tgcgcatagt ttttctgtaa tttacaacag tgctattttc tggtagttct tcggagtgtg    780
ttgctttaat tattaaattt atataatcaa tgaatttggg atcgtcggtt ttgtacaata    840
tgttgccggc atagtacgca gcttcttcta gttcaattac accatttttt agcagcaccg    900
gattaacata actttccaaa atgttgtacg aaccgttaaa caaaaacagt tcacctccct    960
tttctatact attgtctgcg agcagttgtt tgttgttaaa ataacagcc attgtaatga    1020 gacgcacaaa ctaatatcac aaactggaaa tgtctatcaa tatatagttg ctgattgcgc    1080
agatgccctg cgtaagcggg tgtgggcgga caataaagtc ttaaactgaa caaaatagat    1140
ctaaactatg acaataaagt cttaaactag acagaatagt tgtaaactga aatcagtcca    1200
gttatgctgt gaaaaagcat actggacttt tgttatggct aaagcaaact cttcattttc    1260
tgaagtgcaa attgcccgtc gtattaaaga ggggcgtggc caagggcatg taaagactat    1320
attcgcggcg ttgtgacaat ttaccgaaca actccgcggc cgggaagccg atctcggctt    1380
gaacgaattg ttaggtggcg gtacttgggt cgatatcaaa gtgcatcact tcttcccgta    1440
tgcccaactt tgtatagaga gccactgcgg gatcgtcacc gtaatctgct tgcacgtaga    1500
tcacataagc accaagcgcg ttggcctcat gcttgaggag attgatgagc gcggtggcaa    1560
tgccctgcct ccggtgctcg ccggagactg cgagatcata gatatagatc tcactacgcg    1620
gctgctcaaa cttgggcaga acgtaagccg cgagagcgcc aacaaccgct tcttggtcga    1680
aggcagcaag cgcgatgaat gtcttactac ggagcaagtt cccgaggtaa tcggagtccg    1740
gctgatgttg ggagtaggtg gctacgtctc cgaactcacg accgaaaaga tcaagagcag    1800
cccgcatgga tttgacttgg tcagggccga gcctacatgt gcgaatgatg cccatacttg    1860
agccacctaa cttttgtttta gggcgactgc cctgctgcgt aacatcgttg ctgctgcgta    1920
acatcgttgc tgctccataa catcaaacat cgacccacgg cgtaacgcgc ttgctgcttg    1980
gatgcccgag gcatagactg tacaaaaaaa cagtcataac aagccatgaa aaccgccact    2040
gcgccgttac caccgctgcg ttcggtcaag gttctggacc agttgcgtga gcgcatacgc    2100
tacttgcatt acagtttacg aaccgaacag gcttatgtca actgggttcg tgccttcatc    2160
cgtttccacg gtgtgcgtca cccggcaacc ttgggcagca gcgaagtcgc cataacttcg    2220
tatagcatac attatacgaa gttatctgta actataacgg tcctaaggta gcgagtttaa    2280
acactagtat cgattcgcga cctactccgg aatattaata gatcatggag ataattaaaa    2340
tgataaccat ctcgcaaata aataagtatt ttactgtttt cgtaacagtt ttgtaataaa    2400
aaaacctata aatattccgg attattcata ccgtcccacc atcgggcgcg gatcccggtc    2460
```

```
cgaagcgcgc ggaattcaaa ggcctacgtc gacgagctca cttgtcgcgg ccgctttcga    2520
atctagagcc tgcagtctcg acaagcttgt cgagaagtac tagaggatca taatcagcca    2580
taccacattt gtagaggttt tacttgcttt aaaaaacctc ccacacctcc ccctgaacct    2640
gaaacataaa atgaatgcaa ttgttgttgt taacttgttt attgcagctt ataatggtta    2700
caaataaagc aatagcatca caaatttcac aaataaagca ttttttttcac tgcattctag    2760 ttgtggtttg tccaaactca tcaatgtatc ttatcatgtc tggatctgat cactgcttga    2820
gcctagaaga tccggctgct aacaaagccc gaaaggaagc tgagttggct gctgccaccg    2880
ctgagcaata actatcataa cccctagggt atacccatct aattggaacc agataagtga    2940
aatctagttc caaactattt tgtcattttt aattttcgta ttagcttacg acgctacacc    3000
cagttcccat ctattttgtc actcttccct aaataatcct taaaaactcc atttccaccc    3060
ctcccagttc ccaactattt tgtccgccca caaccgtgg aggaaattct ccttgaagtt    3120
tccctggtgt tcaaagtaaa ggagtttgca ccagacgcac ctctgttcac tggtccggcg    3180
tattaaaaca cgatacattg ttattagtac atttattaag cgctagattc tgtgcgttgt    3240
tgatttacag acaattgttg tacgtatttt aataattcat taaatttata atctttaggg    3300
tggtatgtta gagcgaaaat caaatgattt tcagcgtctt tatatctgaa tttaaatatt    3360
aaatcctcaa tagatttgta aaataggttt cgattagttt caaacaaggg ttgttttttcc    3420 gaaccgatgg ctggactatc taatggattt tcgctcaacg ccacaaaact tgccaaatct    3480
tgtagcagca atctagcttt gtcgatattc gtttgtgttt tgttttgtaa taaaggttcg    3540
acgtcgttca aaatattatg cgcttttgta tttctttcat cactgtcgtt agtgtacaat    3600
tgactcgacg taaacacgtt aaatagagct tggacatatt taacatcggg cgtgttagct    3660
ttattaggcc gattatcgtc gtcgtcccaa ccctcgtcgt tagaagttgc ttccgaagac    3720
gattttgcca tagccacacg acgcctatta attgtgtcgg ctaacacgtc cgcgatcaaa    3780
tttgtagttg agcttttttgg aattaccggt tgacttgggt caactgtcag accaagttta    3840
ctcatatata ctttagattg atttaaaact tcattttttaa tttaaaagga tctaggtgaa    3900
gatccttttt gataatctca tgaccacagg cattggcggc cttgctgttc ttctacggca    3960
aggtgctgtg cacgcccagc tgccattttt ggggtgaggt cgttcgcggc cgaggggcgc    4020 agccccctggg gggatggggt gccgcgttag cgggccggga gggttcgaga agggggggca    4080
ccccccttcg gcgtgcgcgg tcacgcgcca gggcgcagcc ctggttaaaa acaaggttta    4140
taaatattgg tttaaaagca ggttaaaaga caggttagcg gtggccgaaa acgggcgga    4200 aacccttgca aatgctggat tttctgcctg tggacagccc ctcaaatgtc aataggtgcg    4260
cccctcatct gtcatcactc tgccccctcaa gtgtcaagga tcgcgcccct catctgtcag    4320
tagtcgcgcc cctcaagtgt caataccgca gggcacttat ccccaggctt gtccacatca    4380
tctgtgggaa actcgcgtaa aatcaggcgt tttcgccgat ttgcgaggct ggccagctcc    4440
acgtcgccgg ccgaaatcga gcctgcccct catctgtcaa cgccgcgccg ggtgagtcgg    4500
cccctcaagt gtcaacgtcc gccctcatc tgtcagtgag ggccaagttt tccgcgtggt    4560
atccacaacg ccggcggcca aaagaagagc tttcacaccg catagaccag ccgcgtaacc    4620
tggca                                                                4625
```

<210> SEQ ID NO 17  
<211> LENGTH: 4490  
<212> TYPE: DNA  
<213> ORGANISM: Artificial
<220> FEATURE:
<223> OTHER INFORMATION: pOmniBac4

<400> SEQUENCE: 17

| | | | | | |
|---|---|---|---|---|---|
| gcaacgcggc | cttttttacgg | ttcctggcct | tttgctggcc | ttttgctcac | atgttctttc | 60 |
| ctgcgttatc | ccctgattga | cttgggtcgc | tcttcctgtg | gatgcgcagg | tatgtacagg | 120 |
| aagaggttta | tactaaactg | ttacattgca | aacgtggttt | cgtgtgccaa | gtgtgaaaac | 180 |
| cgatgtttaa | tcaaggctct | gacgcatttc | tacaaccacg | actctaagtg | tgtgggtgaa | 240 |
| gtcatgcatc | ttttaatcaa | atcccaagat | gtgtataaac | caccaaactg | ccaaaaaatg | 300 |
| aaaactgtcg | acaagctctg | tccgtttgct | ggcaactgca | agggtctcaa | tcctatttgt | 360 |
| aattattgaa | taataaaaca | attataaatg | tcaaatttgt | ttttattaa | cgatacaaac | 420 |
| caaacgcaac | aagaacattt | gtagtattat | ctataattga | aaacgcgtag | ttataatcgc | 480 |
| tgaggtaata | tttaaaatca | ttttcaaatg | attcacagtt | aatttgcgac | aatataattt | 540 |
| tattttcaca | taaactagac | gccttgtcgt | cttcttcttc | gtattccttc | tcttttttcat | 600 |
| ttttctcttc | ataaaaatta | acatagttat | tatcgtatcc | atatatgtat | ctatcgtata | 660 |
| gagtaaattt | tttgttgtca | taaatatata | tgtcttttttt | aatggggtgt | atagtaccgc | 720 |
| tgcgcatagt | ttttctgtaa | tttacaacag | tgctattttc | tggtagttct | tcggagtgtg | 780 |
| ttgctttaat | tattaaattt | atataatcaa | tgaatttggg | atcgtcggtt | ttgtacaata | 840 |
| tgttgccggc | atagtacgca | gcttcttcta | gttcaattac | accatttttt | agcagcaccg | 900 |
| gattaacata | actttccaaa | atgttgtacg | aaccgttaaa | caaaaacagt | tcacctccct | 960 |
| tttctatact | attgtctgcg | agcagttgtt | tgttgttaaa | aataacagcc | attgtaatga | 1020 |
| gacgcacaaa | ctaatatcac | aaactggaaa | tgtctatcaa | tatatagttg | ctgattgcgc | 1080 |
| agatgccctg | cgtaagcggg | tgtgggcgga | caataaagtc | ttaaactgaa | caaaatagat | 1140 |
| ctaaactatg | acaataaagt | cttaaactag | acagaatagt | tgtaaactga | aatcagtcca | 1200 |
| gttatgctgt | gaaaaagcat | actggacttt | tgttatggct | aaagcaaact | cttcattttc | 1260 |
| tgaagtgcaa | attgcccgtc | gtattaaaga | ggggcgtggc | caagggcatg | taaagactat | 1320 |
| attcgcggcg | ttgtgacaat | ttaccgaaca | actccgcggc | cgggaagccg | atctcggctt | 1380 |
| gaacgaattg | ttaggtggcg | gtacttgggt | cgatatcaaa | gtgcatcact | tcttcccgta | 1440 |
| tgcccaactt | tgtatagaga | gccactgcgg | gatcgtcacc | gtaatctgct | tgcacgtaga | 1500 |
| tcacataagc | accaagcgcg | ttggcctcat | gcttgaggag | attgatgagc | gcggtggcaa | 1560 |
| tgccctgcct | ccggtgctcg | ccggagactg | cgagatcata | gatatagatc | tcactacgcg | 1620 |
| gctgctcaaa | cttgggcaga | acgtaagccg | cgagagcgcc | aacaaccgct | tcttggtcga | 1680 |
| aggcagcaag | cgcgatgaat | gtcttactac | ggagcaagtt | cccgaggtaa | tcggagtccg | 1740 |
| gctgatgttg | ggagtaggtg | gctacgtctc | cgaactcacg | accgaaaaga | tcaagagcag | 1800 |
| cccgcatgga | tttgacttgg | tcaggccga | gcctacatgt | gcgaatgatg | cccatacttg | 1860 |
| agccacctaa | ctttgtttta | gggcgactgc | cctgctgcgt | aacatcgttg | ctgctgcgta | 1920 |
| acatcgttgc | tgctccataa | catcaaacat | cgacccacgg | cgtaacgcgc | ttgctgcttg | 1980 |
| gatgcccgag | gcatagactg | tacaaaaaaa | cagtcataac | aagccatgaa | aaccgccact | 2040 |
| gcgccgttac | caccgctgcg | ttcggtcaag | gttctggacc | agttgcgtga | gcgcatacgc | 2100 |
| tacttgcatt | acagtttacg | aaccgaacag | gcttatgtca | actgggttcg | tgccttcatc | 2160 |
| cgtttccacg | gtgtgcgtca | cccggcaacc | ttgggcagca | gcgaagtcgc | cataacttcg | 2220 |
| tatagcatac | attatacgaa | gttatctgta | actataacgg | tcctaaggta | gcgagtttaa | 2280 |

```
acgtacccgt agtggctatg cagggcttg ccgccccgac gttggctgcg agccctgggc    2340
cttcacccga acttgggggt tggggtgggg aaaaggaaga aacgcgggcg tattggtccc    2400 aatgggtct cggtgggta tcgacagagt gccagccctg ggaccgaacc ccgcgtttat     2460
gaacaaacga cccaacaccc gtgcgtttta ttctgtcttt ttattgccgt catagcgcgg   2520
gttccttccg gtattgtctc cttccgtgtt tcagttagcc tcccccatct cccggtaccg   2580
catgctatgc atcagctgct agcaccatgg ctcgagatcc cgggtgatca agtcttcgtc   2640
gagtgattgt aaataaaatg taatttacag tatagtattt taattaatat acaaatgatt   2700
tgataataat tcttatttaa ctataatata ttgtgttggg ttgaattaaa ggtccgtata   2760
ctagtatcct agggtatacc catctaattg gaaccagata agtgaaatct agttccaaac   2820
tattttgtca tttttaattt tcgtattagc ttacgacgct acacccagtt cccatctatt   2880
ttgtcactct tccctaaata atccttaaaa actccatttc cacccctccc agttcccaac   2940
tattttgtcc gcccacaacc ggtggaggaa attctccttg aagtttccct ggtgttcaaa   3000
gtaaaggagt ttgcaccaga cgcacctctg ttcactggtc cggcgtatta aaacacgata   3060
cattgttatt agtacattta ttaagcgcta gattctgtgc gttgttgatt tacagacaat   3120
tgttgtacgt atttttaataa ttcattaaat ttataatctt tagggtggta tgttagagcg   3180
aaaatcaaat gattttcagc gtctttatat ctgaatttaa atattaaatc ctcaatagat   3240
ttgtaaaata ggtttcgatt agtttcaaac aagggttgtt tttccgaacc gatggctgga   3300
ctatctaatg gattttcgct caacgccaca aaacttgcca aatcttgtag cagcaatcta   3360
gctttgtcga tattcgtttg tgttttgttt tgtaataaag gttcgacgtc gttcaaaata   3420
ttatgcgctt ttgtatttct ttcatcactg tcgttagtgt acaattgact cgacgtaaac   3480
acgttaaata gagcttggac atatttaaca tcgggcgtgt tagctttatt aggccgatta   3540
tcgtcgtcgt cccaaccctc gtcgttagaa gttgcttccg aagacgattt tgccatagcc   3600
acacgacgcc tattaattgt gtcggctaac acgtccgcga tcaaatttgt agttgagctt   3660
tttggaatta ccggttgact tgggtcaact gtcagaccaa gtttactcat atatacttta   3720
gattgattta aaacttcatt tttaatttaa aaggatctag gtgaagatcc tttttgataa   3780
tctcatgacc acaggcattg gcggccttgc tgttcttcta cggcaaggtg ctgtgcacgc   3840
ccagctgcca tttttggggt gaggtcgttc gcggccgagg ggcgcagccc ctgggggat    3900 ggggtgccgc gttagcgggc cgggagggtt cgagaagggg gggcaccccc cttcggcgtg   3960
cgcggtcacg cgccagggcg cagccctggt taaaaacaag gtttataaat attggtttaa   4020
aagcaggtta aaagacaggt tagcggtggc cgaaaaacgg gcggaaaccc ttgcaaatgc   4080 tggatttct gcctgtggac agcccctcaa atgtcaatag gtgcgcccct catctgtcat    4140
cactctgccc ctcaagtgtc aaggatcgcg ccctcatct gtcagtagtc gcgcccctca    4200
agtgtcaata ccgcagggca cttatcccca ggcttgtcca catcatctgt gggaaactcg   4260
cgtaaaatca ggcgttttcg ccgatttgcg aggctggcca gctccacgtc gccggccgaa   4320
atcgagcctg cccctcatct gtcaacgccg cgccgggtga gtcggcccct caagtgtcaa   4380
cgtccgcccc tcatctgtca gtgagggcca gttttccgc gtggtatcca caacgccggc    4440
ggccaaaaga agagctttca caccgcatag accagccgcg taacctggca                4490
```

<210> SEQ ID NO 18
<211> LENGTH: 8823
<212> TYPE: DNA
<213> ORGANISM: Artificial
<220> FEATURE:
<223> OTHER INFORMATION: pACKS

<400> SEQUENCE: 18

| | | | | | |
|---|---|---|---|---|---|
| ggtaccgcgg | ccgcgtagag | gatctgttga | tcagcagttc | aacctgttga | tagtacttcg | 60 |
| ttaatacaga | tgtaggtgtt | ggcaccatgc | ataactataa | cggtcctaag | gtagcgacct | 120 |
| aggtatcgat | aatacgactc | actatagggg | aattgtgagc | ggataacaat | tcccctctag | 180 |
| aaataatttt | gtttaacttt | aagaaggaga | tatacatatg | aggcctcgga | tcctgtaaaa | 240 |
| cgacggccag | tgaattcccc | gggaagcttc | gccagggttt | tcccagtcga | gctcgatatc | 300 |
| ggtaccagcg | gataacaatt | tcacatccgg | atcgcgaacg | cgtctcgaga | gatccggctg | 360 |
| ctaacaaagc | ccgaaaggaa | gctgagttgg | ctgctgccac | cgctgagcaa | taactagcat | 420 |
| aaccccttgg | ggcctctaaa | cgggtcttga | ggggttttttt | ggtttaaacc | catctaattg | 480 |
| gactagtagc | ccgcctaatg | agcgggcttt | tttttaattc | ccctatttgt | ttatttttct | 540 |
| aaatacattc | aaatatgtat | ccgctcatga | gacaataacc | ctgataaatg | cttcaataat | 600 |
| attgaaaaag | gaagagtatg | agtattcaac | atttccgtgt | cgcccttatt | ccctttttttg | 660 |
| cggcattttg | ccttcctgtt | tttgctcacc | cagaaacgct | cgtgaaagta | aaagacgcag | 720 |
| aggaccaatt | gggggcacga | gtgggataca | tagaactgga | cttgaatagc | ggtaaaatcc | 780 |
| ttgagagttt | tcgccctgaa | gagcgttttc | caatgatgag | cactttcaaa | gttctgctat | 840 |
| gtggagcagt | attatcccgt | gtagatgcgg | ggcaagagca | actcggacga | cgaatacact | 900 |
| attcgcagaa | tgacttggtt | gaatactccc | cagtgacaga | aaagcacctt | acggacggaa | 960 |
| tgacggtaag | agaattatgt | agtgccgcca | taacgatgag | tgataacact | gcggcgaact | 1020 |
| tacttctgac | aaccatcggt | ggaccgaagg | aattaaccgc | ttttttgcac | aatatgggag | 1080 |
| accatgtaac | tcgccttgac | cgttgggaac | cagaactgaa | tgaagccata | ccaaacgacg | 1140 |
| agcgagacac | cacaatgcct | gcggcaatgg | caacaacatt | acgcaaacta | ttaactggcg | 1200 |
| aactacttac | tctggcttca | cggcaacaat | taatagactg | gcttgaagcg | gataaagttg | 1260 |
| caggaccact | actgcgttcg | gcacttcctg | ctggctggtt | tattgctgat | aaatctgggg | 1320 |
| caggagagcg | tggttcacgg | ggtatcattg | ccgcacttgg | accagatggt | aagccttccc | 1380 |
| gtatcgtagt | tatctacacg | acgggtagtc | aggcaactat | ggacgaacga | atagacaga | 1440 |
| ttgctgaaat | aggggcttca | ctgattaagc | attggtaaac | cgatacaatt | aaaggctcct | 1500 |
| tttggagcct | ttttttttgg | acggaccggt | agaaaagatc | aaaggatctt | cttgagatcc | 1560 |
| ttttttttctg | cgcgtaatct | gctgcttgca | acaaaaaaa | ccaccgctac | cagcggtggt | 1620 |
| ttgtttgccg | gatcaagagc | taccaactct | ttttccgaag | gtaactggct | tcagcagagc | 1680 |
| gcagatacca | aatactgtcc | ttctagtgta | gccgtagtta | ggccaccact | tcaagaactc | 1740 |
| tgtagcaccg | cctacatacc | tcgctctgct | aatcctgtta | ccagtggctg | ctgccagtgg | 1800 |
| cgataagtcg | tgtcttaccg | ggttggactc | aagacgatag | ttaccggata | aggcgcagcg | 1860 |
| gtcgggctga | acgggggggtt | cgtgcacaca | gcccagcttg | gagcgaacga | cctacaccga | 1920 |
| actgagatac | ctacagcgtg | agctatgaga | aagcgccacg | cttcccgaag | ggagaaaggc | 1980 |
| ggacaggtat | ccggtaagcg | gcagggtcgg | aacaggagag | cgcacgaggg | agcttccagg | 2040 |
| gggaaacgcc | tggtatcttt | atagtcctgt | cgggtttcgc | cacctctgac | ttgagcgtcg | 2100 |
| atttttgtga | tgctcgtcag | gggggcggag | cctatggaaa | aacgccagca | acgcggcctt | 2160 |
| tttacggttc | ctggcctttt | gctggccttt | tgctcacatg | ttctttcctg | cgttatcccc | 2220 |
| tgattctgtg | gataaccgta | ttaccgcctt | tgagtgagct | gataccgctc | gccgcagccg | 2280 |

| | |
|---|---|
| aacgaccgag cgcagcgagt cagtgagcga ggaagcggaa gagcgcctga tgcggtattt | 2340 |
| tctccttacg catctgtgcg gtatttcaca ccgcaatggt gcactctcag tacaatctgc | 2400 |
| tctgatgccg catagttaag ccagtataca ctccgctatc gctacgtgac tgggtcatgg | 2460 |
| ctgcgccccg acacccgcca acacccgctg acgcgccctg acgggcttgt ctgctcccgg | 2520 |
| catccgctta cagacaagct gtgaccgtct ccgggagctg catgtgtcag aggttttcac | 2580 |
| cgtcatcacc gaaacgcgcg aggcagggg aattccagat aacttcgtat aatgtatgct | 2640 |
| atacgaagtt atggtaccgc ggccgcgtag aggatctgtt gatcagcagt tcaacctgtt | 2700 |
| gatagtacgt actaagctct catgtttcac gtactaagct ctcatgttta acgtactaag | 2760 |
| ctctcatgtt taacgaacta aaccctcatg gctaacgtac taagctctca tggctaacgt | 2820 |
| actaagctct catgtttcac gtactaagct ctcatgtttg aacaataaaa ttaatataaa | 2880 |
| tcagcaactt aaatagcctc taaggtttta agttttataa gaaaaaaaag aatatataag | 2940 |
| gcttttaaag cttttaaggt ttaacggttg tggacaacaa gccagggatg taacgcactg | 3000 |
| agaagccctt agagcctctc aaagcaattt tgagtgacac aggaacactt aacggctgac | 3060 |
| agaattagct tcacgctgcc gcaagcactc agggcgcaag gctgctaaa ggaagcggaa | 3120 |
| cacgtagaaa gccagtccgc agaaacggtg ctgaccccgg atgaatgtca gctgggaggc | 3180 |
| agaataaatg atcatatcgt caattattac ctccacgggg agagcctgag caaactggcc | 3240 |
| tcaggcattt gagaagcaca cggtcacact gcttccggta gtcaataaac cggtaaacca | 3300 |
| gcaatagaca taagcggcta tttaacgacc ctgccctgaa ccgacgaccg ggtcgaattt | 3360 |
| gctttcgaat ttctgccatt catccgctta ttatcactta ttcaggcgta gcaaccaggc | 3420 |
| gtttaagggc accaataact gccttaaaaa aattacgccc cgccctgcca ctcatcgcag | 3480 |
| tactgttgta attcattaag cattctgccg acatggaagc catcacaaac ggcatgatga | 3540 |
| acctgaatcg ccagcggcat cagcaccttg tcgccttgcg tataatattt gcccatggtg | 3600 |
| aaaacggggg cgaagaagtt gtccatattg gccacgttta aatcaaaact ggtgaaactc | 3660 |
| acccagggat tggctgagac gaaaaacata ttctcaataa acccttaggg gaaataggcc | 3720 |
| aggttttcac cgtaacacgc cacatcttgc gaatatatgt gtagaaactg ccggaaatcg | 3780 |
| tcgtggtatt cactccagag cgatgaaaac gtttcagttt gctcatggaa acggtgtaa | 3840 |
| caagggtgaa cactatccca tatcaccagc tcaccgtctt tcattgccat acggaattcc | 3900 |
| ggatgagcat tcatcaggcg ggcaagaatg tgaataaagg ccggataaaa cttgtgctta | 3960 |
| tttttcttta cggtctttaa aaaggccgta atatccagct gaacggtctg gttataggta | 4020 |
| cattgagcaa ctgactgaaa tgcctcaaaa tgttctttac gatgccattg ggatatatca | 4080 |
| acggtggtat atccagtgat ttttttctcc attttagctt ccttagctcc tgaaaatctc | 4140 |
| gataactcaa aaaatacgcc cggtagtgat cttatttcat tatggtgaaa gttggaccct | 4200 |
| cttacgtgcc gatcaacgtc tcattttcgc caaaagttgg cccagatcaa cgtctcattt | 4260 |
| tcgccaaaag ttggcccaga tctatgtcgg gtgcggagaa agaggtaatg aaatggcacc | 4320 |
| taggtatcga taatacgact cactataggg gaattgtgag cggataacaa ttcccctcta | 4380 |
| gaaataattt tgtttaactt taagaaggag atatacatat gaggcctcgg atcctgtaaa | 4440 |
| acgacggcca gtgaattccc cgggaagctt cgccagggtt tcccagtcg agctcgatat | 4500 |
| cggtaccagc ggataacaat ttcacatccg gatcgcgaac gcgtctcgag agatccggct | 4560 |
| gctaacaaag cccgaaagga agctgagttg gctgctgcca ccgctgagca ataactagca | 4620 |
| taacccctg gggcctctaa acgggtcttg aggggttttt tggtttaaac ccatgtgcct | 4680 |

```
ggcagataac ttcgtataat gtatgctata cgaagttatg gtacgtacta agctctcatg    4740
tttcacgtac taagctctca tgtttaacgt actaagctct catgtttaac gaactaaacc    4800
ctcatggcta acgtactaag ctctcatggc taacgtacta agctctcatg tttcacgtac    4860
taagctctca tgtttgaaca ataaaattaa tataaatcag caacttaaat agcctctaag    4920
gttttaagtt ttataagaaa aaaagaata tataaggctt ttaaagcttt taaggtttaa     4980
cggttgtgga caacaagcca gggatgtaac gcactgagaa gcccttagag cctctcaaag    5040
caattttcag tgacacagga acacttaacg gctgacagaa ttagcttcac gctgccgcaa    5100
gcactcaggg cgcaagggct gctaaaggaa gcggaacacg tagaaagcca gtccgcagaa    5160
acggtgctga ccccggatga atgtcagcta ctgggctatc tggacaaggg aaaacgcaag    5220
cgcaaagaga agcaggtag cttgcagtgg gcttacatgg cgatagctag actgggcggt     5280
tttatggaca gcaagcgaac cggaattgcc agctggggcg ccctctggta aggttgggaa    5340
gccctgcaaa gtaaactgga tggctttctt gccgccaagg atctgatggc gcaggggatc    5400
aagatctgat caagagacag gatgaggatc gtttcgcatg attgaacaag atggattgca    5460
cgcaggttct ccggccgctt gggtggagag gctattcggc tatgactggg cacaacagac    5520
aatcggctgc tctgatgccg ccgtgttccg gctgtcagcg caggggcgcc cggttctttt    5580
tgtcaagacc gacctgtccg gtgccctgaa tgaactgcag gacgaggcag cgcggctatc    5640
gtggctggcc acgacgggcg ttccttgcgc agctgtgctc gacgttgtca ctgaagcggg    5700
aagggactgg ctgctattgg gcgaagtgcc ggggcaggat ctcctgtcat ctcaccttgc    5760
tcctgccgag aaagtatcca tcatggctga tgcaatgcgg cggctgcata cgcttgatcc    5820
ggctacctgc ccattcgacc accaagcgaa acatcgcatc gagcgagcac gtactcggat    5880
ggaagccggt cttgtcgatc aggatgatct ggacgaagag catcaggggc tcgcgccagc    5940
cgaactgttc gccaggctca aggcgcgcat gcccgacggc gaggatctcg tcgtgacaca    6000
tggcgatgcc tgcttgccga atatcatggt ggaaaatggc cgcttttctg gattcatcga    6060
ctgtggccgg ctgggtgtgg cggaccgcta tcaggacata gcgttggcta cccgtgatat    6120
tgctgaagag cttggcggcg aatgggctga ccgcttcctc gtgctttacg gtatcgccgc    6180
tcccgattcg cagcgcatcg ccttctatcg ccttcttgac gagttcttct gagcgggact    6240
ctggggttcg aaatgaccga ccaagcgacg cccaacctgc catcacgaga tttcgattcc    6300
accgccgcct tctatgaaag gttgggcttc ggaatcgttt tccgggacgc cggctggatg    6360
atcctccagc gcggggatct catgctggag ttcttcgccc accccgggat ctatgtcggg    6420
tgcggagaaa gaggtaatga atggcaccct aggtatcgat ggctttacac tttatgcttc    6480
cggctcgtat gttgtgtgga attgtgagcg gataacaatt tcacacagga aacagctatg    6540
accatgatta cgaatttcta gaaataattt tgtttaactt taagaaggag atatacatat    6600
gaggcctcgg atcctgtaaa acgacggcca gtgaattccc cgggaagctt cgccagggtt    6660
ttcccagtcg agctcgatat cggtaccagc ggataacaat ttcacatccg gatcgcgaac    6720
gcgtctcgag actagttccg tttaaaccca tgtgcctggc agataacttc gtataatgta    6780
tgctatacga agttatggta cgtactaagc tctcatgttt cacgtactaa gctctcatgt    6840
ttaacgtact aagctctcat gtttaacgaa ctaaaccctc atggctaacg tactaagctc    6900
tcatggctaa cgtactaagc tctcatgttt cacgtactaa gctctcatgt tgaacaata    6960 aaattaatat aaatcagcaa cttaaatagc ctctaaggtt ttaagtttta taagaaaaa    7020 aagaatatat aaggcttta aagcttttaa ggtttaacgg ttgtggacaa caagccaggg    7080
```

```
atgtaacgca ctgagaagcc cttagagcct ctcaaagcaa ttttgagtga cacaggaaca    7140
cttaacggct gacataattc agcttcacgc tgccgcaagc actcagggcg caagggctgc    7200
taaaggaagc ggaacacgta gaaagccagt ccgcagaaac ggtgctgacc ccggatgaat    7260
gtcagctggg aggcagaata aatgatcata tcgtcaatta ttacctccac ggggagagcc    7320
tgagcaaact ggcctcaggc atttgagaag cacacggtca cactgcttcc ggtagtcaat    7380
aaaccggtaa gtagcgtatg cgctcacgca actggtccag aaccttgacc gaacgcagcg    7440
gtggtaacgg cgcagtggcg gttttcatgg cttgttatga ctgttttttt ggggtacagt    7500
ctatgcctcg ggcatccaag cagcaagcgc gttacgccgt gggtcgatgt ttgatgttat    7560
ggagcagcaa cgatgttacg cagcagggca gtcgccctaa aacaaagtta aacatcatga    7620
gggaagcggt gatcgccgaa gtatcgactc aactatcaga ggtagttggc gtcatcgagc    7680
gccatctcga accgacgttg ctggccgtac atttgtacgg ctccgcagtg gatggcggcc    7740
tgaagccaca cagtgatatt gatttgctgg ttacggtgac cgtaaggctt gatgaaacaa    7800
cgcggcgagc tttgatcaac gaccttttgg aaacttcggc ttcccctgga gagagcgaga    7860
ttctccgcgc tgtagaagtc accattgttg tgcacgacga catcattccg tggcgttatc    7920
cagctaagcg cgaactgcaa tttggagaat ggcagcgcaa tgacattctt gcaggtatct    7980
tcgagccagc cacgatcgac attgatctgg ctatcttgct gacaaaagca agagaacata    8040
gcgttgcctt ggtaggtcca gcggcggagg aactctttga tccggttcct gaacaggatc    8100
tatttgaggc gctaaatgaa accttaacgc tatggaactc gccgcccgac tgggctggcg    8160
atgagcgaaa tgtagtgctt acgttgtccc gcatttggta cagcgcagta accggcaaaa    8220
tcgcgccgaa ggatgtcgct gccgactggg caatggagcg cctgccggcc cagtatcagc    8280
ccgtcatact tgaagctaga caggcttatc ttggacaaga agaagatcgc ttggcctcgc    8340
gcgcagatca gttggaagaa tttgtccact acgtgaaagg cgagatcacc aaggtagtcg    8400
gcaaataatg tctaacaatt cgttcaagcc gacggatcta tgtcgggtgc ggagaaagag    8460
gtaatgaaat ggcacctagg tatcgatggc tttacacttt atgcttccgg ctcgtatgtt    8520
gtgtggaatt gtgagcggat aacaatttca cacaggaaac agctatgacc atgattacga    8580
atttctagaa ataattttgt ttaactttaa gaaggagata tacatatgag gcctcggatc    8640
ctgtaaaacg acggccagtg aattccccgg gaagcttcgc cagggttttc ccagtcgagc    8700
tcgatatcgg taccagcgga taacaatttc acatccggat cgcgaacgcg tctcgagact    8760
agttccgttt aaacccatgt gcctggcaga taacttcgta taatgtatgc tatacgaagt    8820
tat                                                                  8823
```

<210> SEQ ID NO 19
<211> LENGTH: 34
<212> TYPE: DNA
<213> ORGANISM: Artificial
<220> FEATURE:
<223> OTHER INFORMATION: LoxP imperfect repeat

<400> SEQUENCE: 19
ataacttcgt atagcataca ttatacgaag ttat                                 34

<210> SEQ ID NO 20
<211> LENGTH: 31
<212> TYPE: DNA
<213> ORGANISM: Artificial
<220> FEATURE:
<223> OTHER INFORMATION: Adaptor T7InsFor

<400> SEQUENCE: 20
tcccgcgaaa ttaatacgac tcactatagg g                                  31

<210> SEQ ID NO 21
<211> LENGTH: 39
<212> TYPE: DNA
<213> ORGANISM: Artificial
<220> FEATURE:
<223> OTHER INFORMATION: Adaptor T7InsRev

<400> SEQUENCE: 21
cctcaagacc cgtttagagg ccccaagggg ttatgctag                          39

<210> SEQ ID NO 22
<211> LENGTH: 39
<212> TYPE: DNA
<213> ORGANISM: Artificial
<220> FEATURE:
<223> OTHER INFORMATION: Adaptor T7VecFor

<400> SEQUENCE: 22
ctagcataac cccttggggc ctctaaacgg gtcttgagg                           39

<210> SEQ ID NO 23
<211> LENGTH: 31
<212> TYPE: DNA
<213> ORGANISM: Artificial
<220> FEATURE:
<223> OTHER INFORMATION: Adaptor T7VecRev

<400> SEQUENCE: 23
ccctatagtg agtcgtatta atttcgcggg a                                  31

<210> SEQ ID NO 24
<211> LENGTH: 30
<212> TYPE: DNA
<213> ORGANISM: Artificial
<220> FEATURE:
<223> OTHER INFORMATION: Adaptor NdeInsFor

<400> SEQUENCE: 24
gtttaacttt aagaaggaga tatacatatg                                    30

<210> SEQ ID NO 25
<211> LENGTH: 25
<212> TYPE: DNA
<213> ORGANISM: Artificial
<220> FEATURE:
<223> OTHER INFORMATION: Adaptor XhoInsRev

<400> SEQUENCE: 25
gggtttaaac ggaactagtc tcgag                                         25

<210> SEQ ID NO 26
<211> LENGTH: 25
<212> TYPE: DNA
<213> ORGANISM: Artificial
<220> FEATURE:
<223> OTHER INFORMATION: Adaptor XhoVecFor

<400> SEQUENCE: 26
ctcgagacta gttccgttta aaccc                                         25

<210> SEQ ID NO 27
<211> LENGTH: 30

```
<212> TYPE: DNA
<213> ORGANISM: Artificial
<220> FEATURE:
<223> OTHER INFORMATION: Adaptor NdeVecRev

<400> SEQUENCE: 27
catatgtata tctccttctt aaagttaaac                                      30

<210> SEQ ID NO 28
<211> LENGTH: 30
<212> TYPE: DNA
<213> ORGANISM: Artificial
<220> FEATURE:
<223> OTHER INFORMATION: Adaptor SmaBam

<400> SEQUENCE: 28
gaattcactg gccgtcgttt tacaggatcc                                      30

<210> SEQ ID NO 29
<211> LENGTH: 30
<212> TYPE: DNA
<213> ORGANISM: Artificial
<220> FEATURE:
<223> OTHER INFORMATION: Adaptor BamSma

<400> SEQUENCE: 29
ggatcctgta aaacgacggc cagtgaattc                                      30

<210> SEQ ID NO 30
<211> LENGTH: 29
<212> TYPE: DNA
<213> ORGANISM: Artificial
<220> FEATURE:
<223> OTHER INFORMATION: Adaptor SacHind

<400> SEQUENCE: 30
gctcgactgg gaaaaccctg gcgaagctt                                       29

<210> SEQ ID NO 31
<211> LENGTH: 29
<212> TYPE: DNA
<213> ORGANISM: Artificial
<220> FEATURE:
<223> OTHER INFORMATION: Adaptor HindSac

<400> SEQUENCE: 31
aagcttcgcc agggttttcc cagtcgagc                                       29

<210> SEQ ID NO 32
<211> LENGTH: 33
<212> TYPE: DNA
<213> ORGANISM: Artificial
<220> FEATURE:
<223> OTHER INFORMATION: Adaptor BspEco5

<400> SEQUENCE: 32
gatccggatg tgaaattgtt atccgctggt acc                                  33

<210> SEQ ID NO 33
<211> LENGTH: 33
<212> TYPE: DNA
<213> ORGANISM: Artificial
<220> FEATURE:
<223> OTHER INFORMATION: Adaptor Eco5Bsp

<400> SEQUENCE: 33
ggtaccagcg gataacaatt tcacatccgg atc                                  33
```

<210> SEQ ID NO 34
<211> LENGTH: 23
<212> TYPE: DNA
<213> ORGANISM: Artificial
<220> FEATURE:
<223> OTHER INFORMATION: Adaptor PolhInsFor

<400> SEQUENCE: 34
cccaccatcg ggcgcggatc ccg                                              23

<210> SEQ ID NO 35
<211> LENGTH: 23
<212> TYPE: DNA
<213> ORGANISM: Artificial
<220> FEATURE:
<223> OTHER INFORMATION: Adaptor PolhInsRev

<400> SEQUENCE: 35
cgagactgca ggctctagat tcg                                              23

<210> SEQ ID NO 36
<211> LENGTH: 23
<212> TYPE: DNA
<213> ORGANISM: Artificial
<220> FEATURE:
<223> OTHER INFORMATION: Adaptor PolhVecFor

<400> SEQUENCE: 36
cgggatccgc gcccgatggt ggg                                              23

<210> SEQ ID NO 37
<211> LENGTH: 23
<212> TYPE: DNA
<213> ORGANISM: Artificial
<220> FEATURE:
<223> OTHER INFORMATION: Adaptor PolhVecRev

<400> SEQUENCE: 37
cgaatctaga gcctgcagtc tcg                                              23

<210> SEQ ID NO 38
<211> LENGTH: 28
<212> TYPE: DNA
<213> ORGANISM: Artificial
<220> FEATURE:
<223> OTHER INFORMATION: Adaptor P10InsFor

<400> SEQUENCE: 38
ctcccggtac cgcatgctat gcatcagc                                         28

<210> SEQ ID NO 39
<211> LENGTH: 26
<212> TYPE: DNA
<213> ORGANISM: Artificial
<220> FEATURE:
<223> OTHER INFORMATION: Adaptor P10InsRev

<400> SEQUENCE: 39
aatcactcga cgaagacttg atcacc                                           26

<210> SEQ ID NO 40
<211> LENGTH: 28
<212> TYPE: DNA
<213> ORGANISM: Artificial
<220> FEATURE:
<223> OTHER INFORMATION: Adaptor P10VecFor

```
<400> SEQUENCE: 40
gctgatgcat agcatgcggt accgggag                                        28

<210> SEQ ID NO 41
<211> LENGTH: 26
<212> TYPE: DNA
<213> ORGANISM: Artificial
<220> FEATURE:
<223> OTHER INFORMATION: Adaptor P10VecRev

<400> SEQUENCE: 41
ggtgatcaag tcttcgtcga gtgatt                                          26

<210> SEQ ID NO 42
<211> LENGTH: 12
<212> TYPE: DNA
<213> ORGANISM: Artificial
<220> FEATURE:
<223> OTHER INFORMATION: BxtXI recognition sequence general
<220> FEATURE:
<221> NAME/KEY: misc_feature
<222> LOCATION: (4)..(9)
<223> OTHER INFORMATION: any nucleotide

<400> SEQUENCE: 42
ccannnnnnt gg                                                         12

<210> SEQ ID NO 43
<211> LENGTH: 12
<212> TYPE: DNA
<213> ORGANISM: Artificial
<220> FEATURE:
<223> OTHER INFORMATION: BstXI recognition sequence contained in Donor
      vectors

<400> SEQUENCE: 43
ccatgtgcct gg                                                         12

<210> SEQ ID NO 44
<211> LENGTH: 12
<212> TYPE: DNA
<213> ORGANISM: Artificial
<220> FEATURE:
<223> OTHER INFORMATION: BstXI recognition sequence contained in
      Acceptor vectors

<400> SEQUENCE: 44
ccatctaatt gg                                                         12

<210> SEQ ID NO 45
<211> LENGTH: 58
<212> TYPE: DNA
<213> ORGANISM: Artificial
<220> FEATURE:
<223> OTHER INFORMATION: Primer SmaBamVHL

<400> SEQUENCE: 45
gaattcactg gccgtcgttt tacaggatcc ttaatctccc atccgttgat gtgcaatg       58

<210> SEQ ID NO 46
<211> LENGTH: 58
<212> TYPE: DNA
<213> ORGANISM: Artificial
<220> FEATURE:
<223> OTHER INFORMATION: Primer BamSmaEB

<400> SEQUENCE: 46
```

```
ggatcctgta aaacgacggc cagtgaattc gctagctcta gaaataattt tgtttaac      58
```

<210> SEQ ID NO 47
<211> LENGTH: 66
<212> TYPE: DNA
<213> ORGANISM: Artificial
<220> FEATURE:
<223> OTHER INFORMATION: Primer SacHindEB

<400> SEQUENCE: 47

```
gagctcgact gggaaaaccc tggcgaagct tagatctgga tccttactgc acggcttgtt      60
cattgg                                                                66
```

<210> SEQ ID NO 48
<211> LENGTH: 54
<212> TYPE: DNA
<213> ORGANISM: Artificial
<220> FEATURE:
<223> OTHER INFORMATION: Primer HindSacEC

<400> SEQUENCE: 48

```
aagcttcgcc agggttttcc cagtcgagct ccaattggaa ttcgctagct ctag            54
```

<210> SEQ ID NO 49
<211> LENGTH: 67
<212> TYPE: DNA
<213> ORGANISM: Artificial
<220> FEATURE:
<223> OTHER INFORMATION: Primer BspEco5EC

<400> SEQUENCE: 49

```
gatccggatg tgaaattgtt atccgctggt accaagctta gatctggatc cttaacaatc      60
taagaag                                                               67
```

<210> SEQ ID NO 50
<211> LENGTH: 593
<212> TYPE: DNA
<213> ORGANISM: Artificial
<220> FEATURE:
<223> OTHER INFORMATION: Multiple integration element

<400> SEQUENCE: 50

```
tatagcatac attatacgaa gttatctgta actataacgg tcctaaggta gcgagtttaa      60
acactagtat cgattcgcga cctactccgg aatattaata gatcatggag ataattaaaa     120
tgataaccat ctcgcaaata aataagtatt ttactgtttt cgtaacagtt ttgtaataaa     180
aaaacctata aatattccgg attattcata ccgtcccacc atcgggcgcg gatcccggtc     240
cgaagcgcgc ggaattcaaa ggcctacgtc gacgagctca cttgtcgcgg ccgctttcga     300
atctagagcc tgcagtctcg acaagcttgt cgagaagtac tagaggatca taatcagcca     360
taccacattt gtagaggttt tacttgcttt aaaaaacctc ccacacctcc ccctgaacct     420
gaaacataaa atgaatgcaa ttgttgttgt taacttgttt attgcagctt ataatggtta     480
caaataaagc aatagcatca caaatttcac aaataaagca tttttttcac tgcattctag     540
ttgtggtttg tccaaactca tcaatgtatc ttatcatgtc tggatctgat cac            593
```

<210> SEQ ID NO 51
<211> LENGTH: 498
<212> TYPE: DNA
<213> ORGANISM: Artificial
<220> FEATURE:
<223> OTHER INFORMATION: Multiple integration element

<400> SEQUENCE: 51

```
caagccgacg gatctatgtc gggtgcggag aaagaggtaa tgaaatggca cctaggtatc      60
gatactagta tacggacctt taattcaacc caacacaata tattatagtt aaataagaat     120
tattatcaaa tcatttgtat attaattaaa atactatact gtaaattaca ttttatttac     180
aatcactcga cgaagacttg atcacccggg atctcgagcc atggtgctag cagctgatgc     240
atagcatgcg gtaccgggag atggggagg ctaactgaaa cacggaagga gacaataccg      300
gaaggaaccc gcgctatgac ggcaataaaa agacagaata aaacgcacgg gtgttgggtc     360
gtttgttcat aaacgcgggg ttcggtccca gggctggcac tctgtcgata ccccaccgag     420
accccattgg gaccaatacg cccgcgtttc ttccttttcc ccaccccaac ccccaagttc     480
gggtgaaggc ccagggct                                                  498
```

<210> SEQ ID NO 52
<211> LENGTH: 593
<212> TYPE: DNA
<213> ORGANISM: Artificial
<220> FEATURE:
<223> OTHER INFORMATION: Multiple integration element

<400> SEQUENCE: 52

```
tatagcatac attatacgaa gttatctgta actataacgg tcctaaggta gcgagtttaa      60
acactagtat cgattcgcga cctactccgg aatattaata gatcatggag ataattaaaa     120
tgataaccat ctcgcaaata aataagtatt ttactgtttt cgtaacagtt ttgtaataaa     180
aaaacctata aatattccgg attattcata ccgtcccacc atcgggcgcg atcccggtc      240
cgaagcgcgc ggaattcaaa ggcctacgtc gacgagctca cttgtcgcgg ccgctttcga     300
atctagagcc tgcagtctcg acaagcttgt cgagaagtac tagaggatca taatcagcca     360
taccacattt gtagaggttt tacttgcttt aaaaaacctc ccacacctcc ccctgaacct     420
gaaacataaa atgaatgcaa ttgttgttgt taacttgttt attgcagctt ataatggtta     480
caaataaagc aatagcatca caaatttcac aaataaagca ttttttttcac tgcattctag     540
ttgtggtttg tccaaactca tcaatgtatc ttatcatgtc tggatctgat cac            593
```

<210> SEQ ID NO 53
<211> LENGTH: 808
<212> TYPE: DNA
<213> ORGANISM: Artificial
<220> FEATURE:
<223> OTHER INFORMATION: Multiple integration element

<400> SEQUENCE: 53

```
ttagtacgta ctatcaacag gttgaactgc tgatcaacag atcctctacg cggccgcggt      60
accataactt cgtatagcat acattatacg aagttatctg ccaggcacat gggttttact     120
agtatcgatt cgcgacctac tccggaatat taatagatca tggagataat taaaatgata     180
accatctcgc aaataaataa gtatttttact gttttcgtaa cagttttgta ataaaaaaac     240
ctataaatat tccggattat tcataccgtc ccaccatcgg gcgcggatcc cggtccgaag     300
cgcgcggaat tcaaaggcct acgtcgacga gctcactagt gcggccgct ttcgaatcta      360
gagcctgcag tctcgacaag cttgtcgaga agtactagag gatcataatc agccatacca     420
catttgtaga ggttttactt gctttaaaaa acctcccaca cctcccctg aacctgaaac      480
ataaaatgaa tgcaattgtt gttgttaact tgtttattgc agcttataat ggttacaaat     540
aaagcaatag catcacaaat ttcacaaata aagcattttt ttcactgcat tctagttgtg    600
```

```
                                                     -continued gtttgtccaa actcatcaat gtatcttatc atgtctggat ctgatcactg cttgagccta      660
gaagatccgg ctgctaacaa agcccgaaag gaagctgagt tggctgctgc caccgctgag      720
caataactat cataacccct aggtgccatt tcattacctc tttctccgca cccgacataa      780
aaatgagacg ttgatctggg ccaactttt                                        808

<210> SEQ ID NO 54
<211> LENGTH: 211
<212> TYPE: DNA
<213> ORGANISM: Artificial
<220> FEATURE:
<223> OTHER INFORMATION: Antisense sequence to multiple integration
      element of SEQ ID NO: 1

<400> SEQUENCE: 54
ccggatctct cgagacgcgg ttcgcgatcc ggatgtgaaa ttgttatccg ctggtaccga       60
tatcgagctc gactgggaaa accctggcga agcttcccgg ggaattcact ggccgtcgtt     120
ttacaggatc cgaggcctca tatgtatatc tccttcttaa agttaaacaa aattatttct     180
agaggggaat tgttatccgc tcacaattcc c                                    211
```